(12) United States Patent
Muratoglu et al.

(10) Patent No.: US 10,981,302 B2
(45) Date of Patent: Apr. 20, 2021

(54) PEROXIDE CROSS-LINKING AND HIGH TEMPERATURE MELTING

(71) Applicant: THE GENERAL HOSPITAL CORPORATION, Boston, MA (US)

(72) Inventors: Orhun K. Muratoglu, Cambridge, MA (US); Ebru Oral, Newton, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 0 days.

(21) Appl. No.: 16/291,283

(22) Filed: Mar. 4, 2019

(65) Prior Publication Data

US 2019/0255744 A1    Aug. 22, 2019

Related U.S. Application Data

(62) Division of application No. 15/030,206, filed as application No. PCT/US2014/060865 on Oct. 16, 2014, now Pat. No. 10,220,547.

(60) Provisional application No. 61/892,249, filed on Oct. 17, 2013.

(51) Int. Cl.
| | |
|---|---|
| *B29C 35/02* | (2006.01) |
| *B29C 43/00* | (2006.01) |
| *B29B 13/02* | (2006.01) |
| *B29B 13/04* | (2006.01) |
| *C08J 3/20* | (2006.01) |
| *C08J 3/24* | (2006.01) |
| *C08J 7/12* | (2006.01) |
| *B29C 35/08* | (2006.01) |
| *B29C 43/10* | (2006.01) |
| *A61F 2/00* | (2006.01) |
| *B29B 7/88* | (2006.01) |
| *B29B 11/06* | (2006.01) |
| *B29B 11/12* | (2006.01) |
| *B65B 31/00* | (2006.01) |
| *B65B 55/08* | (2006.01) |
| *B65B 55/10* | (2006.01) |
| *B65B 55/16* | (2006.01) |
| *B65B 55/18* | (2006.01) |
| *B29L 31/00* | (2006.01) |
| *B29K 105/00* | (2006.01) |
| *B29K 23/00* | (2006.01) |
| *B29L 9/00* | (2006.01) |
| *B29C 71/02* | (2006.01) |
| *B29B 13/00* | (2006.01) |

(52) U.S. Cl.
CPC ........ *B29C 35/0805* (2013.01); *A61F 2/0095* (2013.01); *B29B 7/88* (2013.01); *B29B 11/06* (2013.01); *B29B 11/12* (2013.01); *B29B 13/022* (2013.01); *B29B 13/045* (2013.01); *B29C 35/02* (2013.01); *B29C 35/0866* (2013.01); *B29C 43/006* (2013.01); *B29C 43/10* (2013.01); *B65B 31/00* (2013.01); *B65B 55/08* (2013.01); *B65B 55/10* (2013.01); *B65B 55/16* (2013.01); *B65B 55/18* (2013.01); *C08J 3/203* (2013.01); *C08J 3/24* (2013.01); *C08J 7/12* (2013.01); *C08J 7/123* (2013.01); *B29B 2013/002* (2013.01); *B29C 2035/085* (2013.01); *B29C 2035/0877* (2013.01); *B29C 2071/022* (2013.01); *B29C 2791/001* (2013.01); *B29C 2791/002* (2013.01); *B29K 2023/0683* (2013.01); *B29K 2105/0035* (2013.01); *B29K 2995/0087* (2013.01); *B29L 2009/00* (2013.01); *B29L 2031/7532* (2013.01); *C08J 2323/06* (2013.01)

(58) Field of Classification Search
CPC ................ B29C 2071/022; C08J 3/24; B29K 2023/0683
See application file for complete search history.

(56) References Cited

U.S. PATENT DOCUMENTS

| | | | |
|---|---|---|---|
| 3,974,132 | A | 8/1976 | Vaidiserri |
| 5,032,450 | A | 7/1991 | Rechlicz et al. |
| 5,096,654 | A | 3/1992 | Craggs et al. |
| 5,827,904 | A | 10/1998 | Hahn |
| 5,879,400 | A | 3/1999 | Merrill et al. |
| 6,165,220 | A | 12/2000 | McKellop et al. |
| 6,316,158 | B1 | 11/2001 | Saum et al. |
| 6,448,315 | B1 | 9/2002 | Lidgren et al. |
| 6,641,617 | B1 | 11/2003 | Merrill et al. |
| 6,852,772 | B2 | 2/2005 | Muratoglu et al. |
| 7,205,339 | B2 | 4/2007 | Muratoglu |
| 7,381,752 | B2 | 6/2008 | Guard et al. |
| 7,431,874 | B2 | 10/2008 | Muratoglu et al. |
| 7,790,779 | B2 | 9/2010 | Muratoglu |

(Continued)

FOREIGN PATENT DOCUMENTS

| | | |
|---|---|---|
| EP | 1457172 A1 | 9/2004 |
| EP | 0881919 B1 | 8/2005 |

(Continued)

OTHER PUBLICATIONS

Chen et al. "Photocrosslinking of Polyethylene. OI. Photoinitiatiators, Crosslinking Agent, and Reaction Kinetics" Nov. 1989, J. Polymer Science, Polymer Chemistry Ed. Interscience Publishers, NY NY, 27(12):4051-4075.

(Continued)

*Primary Examiner* — Jeffrey C Mullis
(74) *Attorney, Agent, or Firm* — Troutman Pepper Hamilton Sanders LLP

(57) ABSTRACT

Methods of making oxidation and wear resistant polymeric materials using peroxide cross-linking and high temperature melting process are disclosed. A multiple step procedure for enabling the manufacturing of such material without size limitations is also disclosed.

23 Claims, 14 Drawing Sheets

(56) References Cited

U.S. PATENT DOCUMENTS

| | | |
|---|---|---|
| 7,833,452 B2 | 11/2010 | Muratogiu et al. |
| 7,858,671 B2 | 12/2010 | Merrill et al. |
| 8,420,000 B2 | 4/2013 | Muratoglu et al. |
| 8,425,815 B2 | 4/2013 | Muratoglu et al. |
| 8,461,225 B2 | 6/2013 | Muratoglu et al. |
| 8,529,937 B2 | 9/2013 | Brunner et al. |
| 8,530,057 B2 | 9/2013 | Muratoglu et al. |
| 8,569,395 B2 | 10/2013 | Muratoglu et al. |
| 8,858,979 B1 | 10/2014 | DesJardins et al. |
| 8,933,145 B2 | 1/2015 | Oral et al. |
| 9,273,189 B2 | 3/2016 | Muratoglu et al. |
| 9,370,878 B2 | 6/2016 | Muratoglu et al. |
| 9,433,705 B2 | 9/2016 | Muratoglu et al. |
| 9,681,683 B2 | 6/2017 | Esposti et al. |
| 9,731,047 B2 | 8/2017 | Oral et al. |
| 10,220,547 B2 | 3/2019 | Muratoglu et al. |
| 2002/0064653 A1 | 5/2002 | Ladika et al. |
| 2004/0156879 A1 | 8/2004 | Muratoglu |
| 2005/0090571 A1 | 4/2005 | Mehta et al. |
| 2006/0064653 A1 | 3/2006 | Zhang et al. |
| 2007/0059334 A1 | 3/2007 | Abi et al. |
| 2007/0114702 A1 | 5/2007 | Muratoglu et al. |
| 2007/0213835 A1 | 9/2007 | Wimmer et al. |
| 2007/0265369 A1 | 11/2007 | Muratoglu |
| 2007/0267030 A1 | 11/2007 | Muratoglu et al. |
| 2008/0215142 A1 | 9/2008 | Muratoglu et al. |
| 2008/0319137 A1 | 12/2008 | Rufner et al. |
| 2009/0030524 A1 | 1/2009 | Schroeder et al. |
| 2009/0181253 A1 | 7/2009 | Michalik et al. |
| 2009/0243159 A1 | 10/2009 | Sun |
| 2010/0190882 A1 | 7/2010 | Muratoglu et al. |
| 2010/0292374 A1 | 11/2010 | Bellare |
| 2011/0039014 A1 | 2/2011 | King et al. |
| 2011/0040381 A1 | 2/2011 | Kidd et al. |
| 2011/0070454 A1 | 3/2011 | Gregg et al. |
| 2012/0041094 A1 | 2/2012 | Oral |
| 2012/0046380 A1 | 2/2012 | Morrison et al. |
| 2012/0267819 A1 | 10/2012 | Freedman |
| 2013/0203885 A1 | 8/2013 | Muratoglu et al. |
| 2014/0098001 A1 | 4/2014 | Van Oosterbosch et al. |
| 2015/0151866 A1 | 6/2015 | Oral |
| 2015/0190545 A1 | 7/2015 | Oral |
| 2015/0314038 A1 | 11/2015 | Oral et al. |
| 2016/0215117 A1 | 7/2016 | Muratoglu |
| 2016/0250779 A1 | 9/2016 | Muratoglu |
| 2017/0137603 A1 | 5/2017 | Morrison et al. |
| 2017/0259467 A1 | 9/2017 | Muratoglu et al. |
| 2019/0134273 A1 | 5/2019 | Oral et al. |

FOREIGN PATENT DOCUMENTS

| | | |
|---|---|---|
| EP | 1779877 A1 | 5/2007 |
| EP | 2384774 A2 | 11/2011 |
| WO | 1997029793 A1 | 8/1997 |
| WO | 1999029793 A1 | 6/1999 |
| WO | 2001005337 A1 | 1/2001 |
| WO | 2001080778 A1 | 11/2001 |
| WO | 2002048259 A2 | 6/2002 |
| WO | 2005074619 A2 | 8/2005 |
| WO | 2005110276 A1 | 11/2005 |
| WO | 2006026040 A1 | 3/2006 |
| WO | 2007024684 A2 | 3/2007 |
| WO | 2007024689 A2 | 3/2007 |
| WO | 2008092047 A1 | 7/2008 |
| WO | 2010096771 A2 | 8/2010 |
| WO | 2013151960 A2 | 10/2013 |
| WO | 2015057943 A2 | 4/2015 |
| WO | 2017192347 A1 | 11/2017 |
| WO | 2019046243 A2 | 3/2019 |

OTHER PUBLICATIONS

Evaluation of cross-linked UHMWPE with regards to its suitability as implant material for hip joint shells, pp. 1-91, Technical Univ. of Berlin, Plastics Research (Nov. 2003) (German) translation).

Evaluation of cross-linked UHMWPE with regards to its suitability as implant material for hip joint shells, pp. 1-91, Technical Univ. of Berlin, PlasticsResearch (Nov. 2003) (English translation).

International Search Report and Written Opinion for PCT/US2010/024935 dated Sep. 27, 2010.

International Search Report and Written Opinion for PCT/US2013/034887 dated Aug. 6, 2013.

International Search Report and Written Opinion for PCT/US2014/060865 dated Mar. 13, 2015.

International Search Report and Written Opinion for PCT/US2018/048256 dated Mar. 13, 2019.

IRGANOX 1010, Phenolic Primary Antioxidant for Processing and Long-Term Thermal Stabilization, Ciba Specialty Chemicals, Inc. (Aug. 1998).

Atkinson et al. "Materials for Internal Prostheses: The Present Position and Possible Future Developments" 1980, Biomaterials 1(2):89-99 (abstract only).

Costa et al. Mechanism of Crosslinking and Oxidative Degradation UHMWPE handbook.

Kurtz "Chapter 16, Vitamin-E Blended UHMWPE Biomaterials" 2005, UHMWPE Handbook: Ultra high molecular weight polyethylene in total joint, vol. 11:235-250 (abstract only).

Oral et al. "A Surface Crosslinked UHMWPE Stabilized by Vitamin E With Low Wear and High Fatigue Strength" 2010, Biomaterials 31(27):7051-7060.

Oral et al. "Peroxide Cross-Linked UHMWPE Blended with Vitamin E" 2016, J. Biomed. Mater. Res., Part B 105 (6):1379-1389.

Morshedian et al. "Polyethylene Cross-Linking by Two-Step Silane Method: A Review" 2009, Iranian Polymer Journal 18(2):103-128.

Fang et al. "Processing and mechanical properties of HA/UHMWPE nanocomposite" 2006, Biomaterials 27:3701-3707.

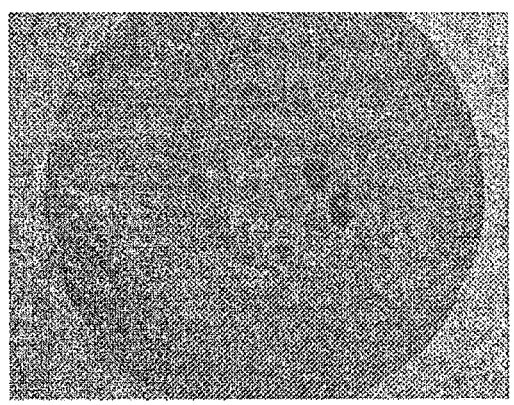 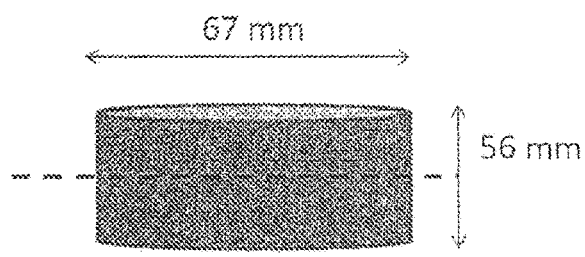
(a) (b)
Figure 1A-B

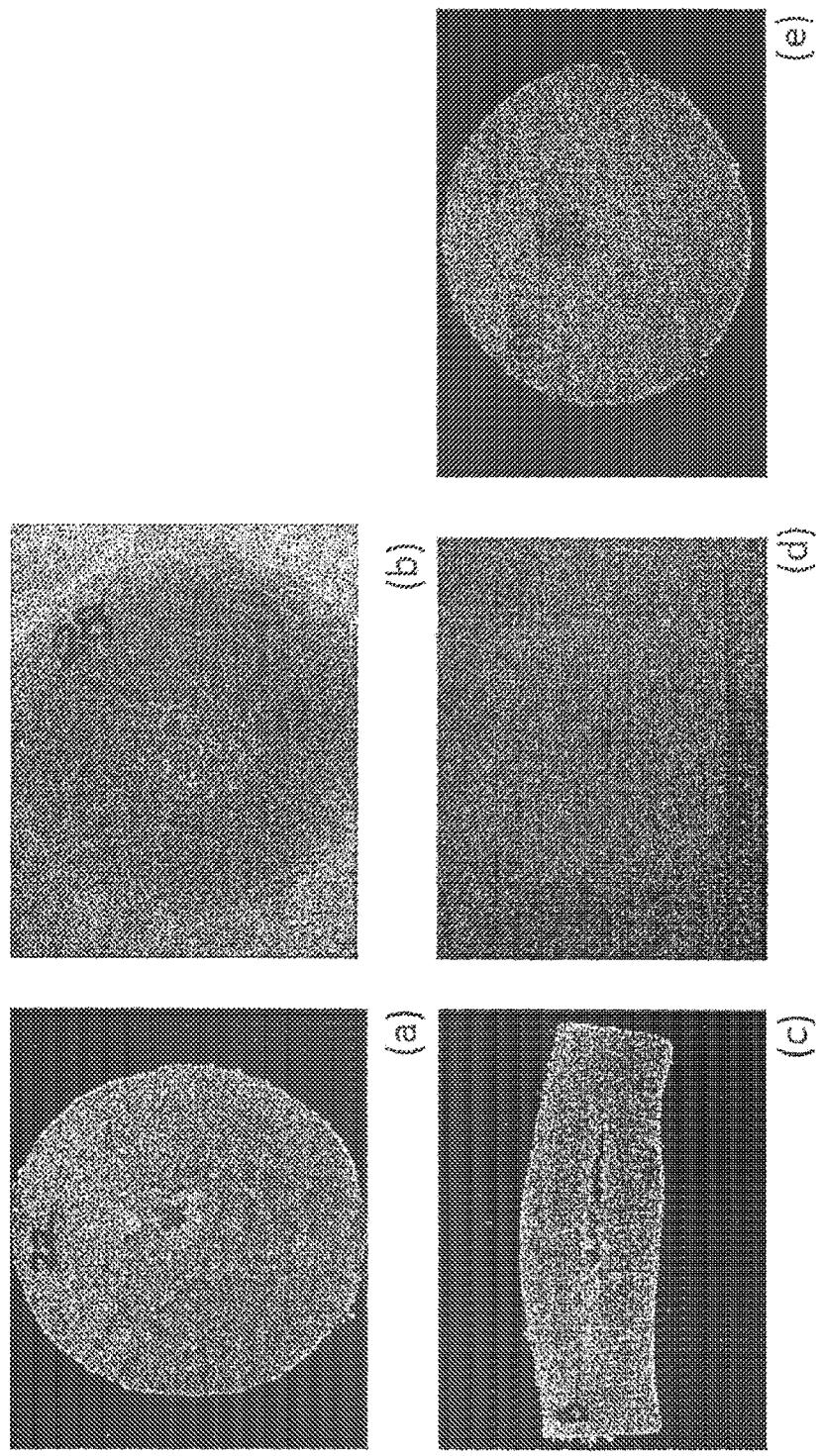
Figure 2A-E

PEROXIDE CROSS-LINKING AND HIGH TEMPERATURE MELTING

CROSS REFERENCE TO RELATED APPLICATIONS

This application is a divisional of U.S. Ser. No. 15/030,206, filed Apr. 18, 2016 (allowed), which is a 371 of PCT/US2014/060865, filed Oct. 16, 2014, which claims priority to U.S. Ser. No. 61/892,249, filed Oct. 17, 2013, each of which are hereby incorporated by reference.

STATEMENT REGARDING FEDERALLY SPONSORED RESEARCH

Not Applicable

BACKGROUND OF THE INVENTION

Joint implants have been manufactured from polyolefins, particularly high density and ultrahigh molecular weight polyethylene (UHMWPE). Today, almost all polymeric joint implants are manufactured from UHMWPEs with molecular weight in the range of 2 to 6 million grams/mol. The viscosity of these polymers generally increases with increasing molecular weight and their melt flow rate (MFR) generally decrease. At these molecular weights, UHMWPE resin can only be consolidated into solid forms by methods of compression molding (for example, compression molding, direct compression molding, hot isostatic molding) and specialized extrusion (ram extrusion). These consolidated forms can be used as end-products such as joint implants and end-products can be machined further from these consolidated solid forms such as sheets, bars or rods. Alternatively, preforms, i.e. transient solid forms before the end-product, can be machined from these consolidated forms and further treated before a final end product can be made by for example, machining.

The mechanical properties of the consolidated solid forms of polymeric resin are dependent on the consolidation method and conditions. In addition, one or more of the mechanical properties can be enhanced further by further treatment of the consolidated form, for example by peroxide cross-linking (U.S. Application No. 61/756,596), high pressure crystallization (U.S. Pat. Nos. 8,420,000; 8,425,815; 8,426,486) or high temperature melting (U.S. Patent Publication No. 2012/0041094). These methods may include exposure to temperatures above the melting point of polyethylene, especially temperatures close to or greater than 200° C. for prolonged periods of time.

During the consolidation of UHMWPE, there may be variable amounts of dissolved and trapped gases in the polymer matrix. The amount of trapped gas may depend on the relative rates of cooling and crystallization of different parts of the pressed form of the polymer in the last steps of consolidation. Finally, high temperature exposure of such a consolidated form results in the expansion of the trapped gases and can cause defects in the samples (FIGS. 1 and 2). These defects can be exacerbated by molecular processes accompanying high temperature exposure.

This invention discloses methods of manufacturing peroxide cross-linked and high temperature melted polymeric material total joint implants, where peroxide cross-linking is limited to a finite thickness on the surfaces where wear resistance is desired and the high temperature melted polymeric material makes up the rest of the joint implant. This is essentially a medical implant with non-uniform properties. The surface has good wear resistance and the bulk has good mechanical properties.

This invention also discloses a method of manufacturing of high temperature melted consolidated UHMWPE for total joint implants in more shapes and sizes (FIG. 3). The invention comprises a method of making an implant, wherein the UHMWPE powder is made into a 'pre-molded green' shape by sintering with and without pressure and with or without elevated temperature without completely consolidating the material, exposing this pre-molded form to high temperature, then completely molding the material into a consolidated form from which implants can be machined, by irradiating the consolidated form, machining an implant, packaging and sterilizing the implant.

SUMMARY OF THE INVENTION

In one embodiment, the invention encompasses a method of making a consolidated polymeric material comprising the steps of blending the polymeric material with one or more additives; pre-molding the blended polymeric material into a partially consolidated form; heating the pre-molded polymeric material to a temperature above the melting temperature of the blended polymeric material for a period of time; cooling the pre-molded blended polymeric material; and completely consolidating the pre-molded, heat treated blended polymeric material. The polymeric material blended with one or more additives can be ultrahigh molecular weight polyethylene powder blended with vitamin E. The premolded blended polymeric material can be fabricated by using temperature and pressure without fully consolidating the powder; that is the pre-molded blended polymeric material has porosity that can be measured with state-of-the-art techniques. The heating of the premolded polymeric material can be carried out at above 200° C.; this is to subject the material to high temperature melting. With a porous preform the high temperature melting does not result in the cavitation shown in FIGS. 1 and 2 even with larger size samples; this cavitation occurs when larger size samples that are consolidated with minimal porosity are subjected to high temperature melting. Typically after the high temperature melting the premolded polymeric material is cooled down to room temperature, although this is not necessary. Cooling down to room temperature may only be needed when the subsequent consolidation step is carried out in a separate vessel, oven, chamber, or a mold. This final consolidation step, also referred to as full consolidation or complete consolidation, is needed to reduce the porosity of the high temperature melt treated premolded polymeric material. In certain embodiments, the polymeric material is irradiated after the final consolidation step and subsequently machined into an article such as an implant shape. The article is packaged and sterilized.

In one embodiment, the invention encompasses a method of making a consolidated polymeric material comprising the steps of blending the polymeric material with one or more additives; pre-molding the blended polymeric material into a partially consolidated form under hydrostatic pressure below 200° C., followed by completely consolidating by heating the pre-molded polymeric material to a temperature above 200° C. for a period of time under hydrostatic pressure; and cooling the completely consolidated pre-molded blended polymeric material. In some embodiments the said hydrostatic pressure can be applied by the use of hot isostatic pressing equipment. In certain embodiments the said hydrostatic pressure can be replaced by uniaxial pressure.

In one embodiment, the invention encompasses a method of making a consolidated polymeric material comprising the steps of blending the polymeric material with one or more additives; consolidating the polymeric material blend under hydrostatic pressure above 200° C.; and cooling the completely consolidated blended polymeric material.

In one embodiment, the invention encompasses a method of making a cross-linked consolidated polymeric material comprising the steps of blending the polymeric material with one or more additives; pre-molding the blended polymeric material into a partially consolidated form; heating the pre-molded polymeric material to a temperature above the melting temperature of the blended polymeric material for a period of time; cooling the pre-molded blended polymeric material; completely consolidating the pre-molded, heat treated blended polymeric material; and irradiating the consolidated polymeric material.

In one embodiment, the invention encompasses a method of making a medical implant comprising the steps of blending a polymeric material with one or more additives; pre-molding the blended polymeric material into a partially consolidated form; heating the pre-molded blended polymeric material to a temperature above the melting temperature of the blended polymeric material for a period of time; cooling the pre-molded blended polymeric material; completely consolidating the pre-molded, heat treated blended polymeric material; machining the consolidated polymeric material into an article or an implant shape; and irradiating the article or the medical implant. In some embodiments the irradiated article is machined into medical implant shape.

In most embodiments, the polymeric material, the article, or the medical implant is heated after irradiation.

In some embodiments, the cooling step after subjecting the pre-molded blended polymeric material to high temperature melting is optional.

In one embodiment, the invention encompasses a method of making a cross-linked consolidated polymeric material comprising the steps of blending the polymeric material with one or more additives; pre-molding the blended polymeric material into a partially consolidated form; heating the pre-molded polymeric material to a temperature above the melting temperature of the blended polymeric material for a period of time; cooling the pre-molded blended polymeric material; completely consolidating the pre-molded, heat treated blended polymeric material; irradiating the consolidated polymeric material and heating the irradiated consolidated polymeric material.

In one embodiment, the invention encompasses a method of making a medical implant comprising the steps of blending a polymeric material with one or more additives; pre-molding the blended polymeric material into a partially consolidated form; heating the pre-molded blended polymeric material to a temperature above the melting temperature of the blended polymeric material for a period of time; cooling the pre-molded blended polymeric material; completely consolidating the pre-molded, heat treated blended polymeric material; machining the consolidated polymeric material into a medical implant shape: and irradiating the medical implant.

In one embodiment, the invention encompasses a method of making a medical implant comprising the steps of blending a polymeric material with one or more additives; pre-molding the blended polymeric material into a partially consolidated form; heating the pre-molded blended polymeric material to a temperature above the melting temperature of the blended polymeric material for a period of time; cooling the pre-molded blended polymeric material; completely consolidating the pre-molded, heat treated blended polymeric material; irradiating the consolidated polymeric material; heating the irradiated consolidated polymeric material; and cooling, machining the irradiated consolidated material into implant shape.

In one embodiment, the invention encompasses a method of making a medical implant comprising the steps of blending a polymeric material with one or more additives; pre-molding the blended polymeric material into a partially consolidated form; heating the pre-molded blended polymeric material to a temperature above the melting temperature of the blended polymeric material for a period of time; cooling the pre-molded blended polymeric material; and completely consolidating the pre-molded, heat treated blended polymeric material into implant shape by direct compression molding. In certain embodiments, implant shape achieved by direct compression molding is incomplete. Therefore additional machining steps are needed to obtain the final implant shape. For example direct compression molding of some tibial inserts forms the articular surface, the superior surface, during molding; the backside features of the implant are machined after the direct compression molding is completed.

In one embodiment, the invention encompasses a method of making a interlocked hybrid medical implant comprising the steps of blending a polymeric material with one or more additives; pre-molding the blended polymeric material into a partially consolidated form; heating the pre-molded blended polymeric material to a temperature above the melting temperature of the blended polymeric material for a period of time; cooling the pre-molded blended polymeric material; and completely consolidating the pre-molded, heat treated blended polymeric material into implant shape by direct compression molding onto a second material. That said second material can be a metallic material or a ceramic material or a polymeric material. The said second material can have porosity with open channels to allow for penetration of the heat treated blended polymeric material in order to generate a strong interface between the said second material in the said heat treated blended polymeric material. The complete consolidation step of the premolded heat treated blended polymeric material serves two purposes: one is to decrease the porosity of the said premolded heat treated blended polymeric material and second is to penetrate the said polymeric material into the open pores of the second material.

In some embodiments the polymeric material with one or more additives may be replaced with polymeric material containing no additives.

In one embodiment, the invention encompasses a method of making a cross-linked consolidated polymeric material comprising the steps of pre-molding the polymeric material into a partially consolidated form; heating the pre-molded polymeric material to a temperature above the melting temperature of the polymeric material for a period of time; cooling the pre-molded polymeric material; completely consolidating the pre-molded, heat treated polymeric material; irradiating the consolidated polymeric material; machining the irradiated consolidated polymeric material; diffusing the implant preform with one or more additives; and heating and subsequently cooling the diffused implant preform.

In one embodiment, the invention encompasses a method of making a medical implant comprising the steps of pre-molding the polymeric material into a partially consolidated form; heating the pre-molded polymeric material to a temperature above the melting temperature of the polymeric material for a period of time; cooling the pre-molded polymeric material; completely consolidating the pre-molded, heat treated polymeric material; irradiating the consolidated polymeric material; machining the irradiated consolidated polymeric material into a medical implant perform; diffusing the implant preform with one or more additives; and heating the diffused implant perform and subsequently cooling and machining into implant shape.

In one embodiment, the invention encompasses a method of making a consolidated polymeric material comprising the steps of pre-molding a polymeric material into partially consolidated form; heating the pre-molded polymeric material to a temperature above its melting temperature of the polymeric material for a period of time; cooling the heat treated pre-molded polymeric material; layering the heat treated pre-molded polymeric material with a layer of a cross-link agent-blended pre-molded polymeric material or resin polymeric material; and completely consolidating the layered material. In some embodiments the heat treated premolded polymeric material is layered on top with a layer of cross-linking agent blended premolded polymeric material or resin polymeric material before the subsequent complete consolidation of the two layers together. The complete consolidation step is typically carried out by direct compression molding. During the complete consolidation step the cross-linking agent causes the polymeric material to cross-link while at the same time the temperature and pressure applied fuses the layers together and decreases the porosity of the heat treated premolded polymeric material.

In one embodiment, the invention encompasses a method of making a medical implant comprising steps of pre-molding a polymeric material into partially consolidated form; heating the pre-molded polymeric material to a temperature above its melting temperature of the polymeric material for a period of time; cooling the heat treated pre-molded polymeric material; layering the heat treated pre-molded polymeric material with more than one layer of cross-link agent-blended pre-molded polymeric material or resin polymeric material; and completely consolidating the layered material. In some embodiments the heat treated premolded polymeric material is layered both on top and on the bottom with a layer of cross-linking agent blended premolded polymeric material or resin polymeric material before the subsequent complete consolidation of the three layers together. The complete consolidation step is typically carried out by direct compression molding. During the complete consolidation step the cross-linking agent causes the polymeric material to cross-link while at the same time the temperature and pressure applied fuses the layers together and decreases the porosity of the heat treated premolded polymeric material.

In the embodiments where the heat treated premolded polymeric material is layered with polymeric material containing cross-linking agent, the said cross linking agent is a peroxide.

In one embodiment, the invention encompasses a method of making a medical implant comprising the steps of molding a polymeric material into partially consolidated form; heating the pre-molded polymeric material to a temperature above its melting temperature of the polymeric material for a period of time; cooling the pre-molded polymeric material; layering the pre-molded polymeric material with a layer of a cross-link agent-blended pre-molded or resin polymeric material; and completely consolidating the layered material.

Optionally, the additive used in the embodiments described above is an antioxidant and/or a cross-linking agent. In a non-limiting example, the additive is vitamin E and/or a peroxide.

In some embodiments, the polymeric material is irradiated after the complete consolidation step.

In some embodiments, the irradiated polymeric material is further heated below the melting point of the irradiated polymeric material.

In some embodiments, the irradiated polymeric material is further heated above the melting point of the irradiated polymeric material.

In some embodiments, the polymeric material is heated below or above the melting point of the polymeric material.

In some embodiments, the complete consolidation step is carried out by using the consolidation techniques known in the art such as direct compression molding, uniaxial compression, or hot isostatic pressing.

In some embodiments, the polymeric material is blended with one or more antioxidants. In some embodiments, the polymeric material is blended with vitamin E.

In some embodiments, the polymeric material is chosen from high-density-polyethylene, low-density-polyethylene, linear-low-density-polyethylene, ultra-high molecular weight polyethylene (UHMWPE), copolymers or mixtures thereof.

In some embodiments, the pre-molding is done by compression. In some embodiments, the pre-molding is done by isostatic pressure or hydrostatic pressure. In some embodiments, the pre-molding is done at a temperature between room temperature and the peak melting temperature of the polymeric material. In some embodiments, the pre-molding is done at a temperature close to the peak melting temperature of the polymeric material. In some embodiments, the pre-molding is done at a temperature above the peak melting temperature of the polymeric material. In some embodiments, the pre-molding is done at below the ambient pressure. In some embodiments, the pre-molding is done under vacuum. In some embodiments, the pre-molding is done under about 1, 2, 3, 4, 5 MPa or more of uniaxial or hydrostatic pressure. In some embodiments, the pre-molding is done by increasing the temperature above 20° C. in the absence of any added pressure beyond ambient pressure.

In some embodiments, the heat treatment after pre-molding is done at a temperature above 200° C. In some embodiments, the heat treatment after pre-molding is done at a temperature between 280 and 330° C. In some embodiments, the heat treatment after pre-molding is done for at least 1 hour up to 1 week. In some embodiments, the heat treatment after pre-molding is done for between 2 and 8 hours. In some embodiments, the heat treatment after pre-molding is done in inert gas, or a mixture of inert gas and air.

In some embodiments, the complete consolidation step is done by compression. In some embodiments, the complete consolidation step is done by applying isostatic or hydrostatic pressure. In some embodiments, the complete consolidation is done above the peak melting temperature of the polymeric material and a pressure from 0.1 to 1000 MPa. In some embodiments, the complete consolidation is done at a temperature between 140 and 230° C. or 150 and 230° C. or 160 and 230° C. or 170 and 230° C. and a pressure below 10 MPa or between 10 and 25 MPa or above 25 MPa.

In some embodiments, the irradiation is an ionizing irradiation. In some embodiments, the irradiation is x-ray irradiation. In some embodiments, the radiation as ultraviolet irradiation. In some embodiments, the irradiation is an electron beam irradiation. In some embodiments, the irradiation is a gamma irradiation. In some embodiments, the irradiation is performed at about room temperature. In some embodiments, the irradiation is performed at an elevated temperature below the melting point of the polymeric material. In some embodiments, the irradiation is performed at an elevated temperature close to the peak melting temperature of the polymeric material. In some embodiments, the irradiation is performed at an elevated temperature above the melting temperature of the polymeric material.

In some embodiments, the second material in the complete consolidation to form an interlocked hybrid material is a porous metal.

In some embodiments, the second material in the complete consolidation to form an interlocked hybrid material is a porous material. In some embodiments the porous material is only porous on one side. In some embodiments, the porosity in the porous material is nonuniform. In some embodiments, the porosity in the porous material has different for sizes on either side. In some embodiments the porous material as a continuous nonporous section within the above. The purpose of the porous material and fabrication of an interlocked hybrid material is to create a mono block medical implant. The polymeric material that is fused together with the porous material forms implants, where by the polymeric material constitutes the articular surface and the porous material is on the backside abutting the bone. In patients the bone will grow into the pores on the backside of implants to achieve fixation. The interface between the polymeric material in the porous material needs to be strong enough to avoid separation of the polymeric material from the porous material in the patient. In some embodiments the porous material is metallic, ceramic, or polymeric in nature.

In some embodiments, the final polymeric material is machined into an implant.

In some embodiments, the medical implant is packaged and sterilized. Optionally, the packaging is done in inert gas or partial inert gas or in vacuum. Optionally, the sterilization is a gamma sterilization or a gas sterilization. Optionally, the sterilization is by exposure to ethylene oxide gas. Optionally, the sterilization is by exposure to gas plasma. Optionally, the sterilization is by exposure to ionizing radiation such as gamma irradiation, x-ray irradiation, or electron beam irradiation. Optionally, the sterilization is by autoclave.

In some embodiments, the heating after irradiation is done below the peak melting temperature of the polymeric material. In some embodiments, the heating after irradiation is done above the peak melting temperature of the polymeric material. The said heating after irradiation is done in inert gas, in vacuum, or in air. In some embodiments, the said heating after irradiation is done in a mixture of air and different inert gases.

In some embodiments, the irradiation is to a dose of 0.1 kGy to 1000 kGy. In some embodiments, the irradiation is to a dose of 150 or 175 kGy. In some embodiments, the irradiation is to a dose of 100, 125, 200, 225, 250, 275, 300, 325, 350, 375, 400 kGy, or more. In some embodiments the irradiation dose rate is also adjusted. For instance in some embodiments the irradiation using electron beam is carried out at a rate of 25, 50, 100, 125, 150, 200, 250, 300 kGy/pass or more.

In this invention, 'partial consolidation' or 'partially consolidated' or 'pre-molding' of the polymeric material is described. These states refer to a state of the polymeric material which is less integrated than a 'completely consolidated' form of the polymeric material with measurable porosity. The premolded polymeric material is subjected to high temperature melting. In the presence of the porous structure there is reduced cavitation formed during the high temperature melting step. The subsequent complete consolidation into solid forms of implant stock or implants reduce the porosity and also heal the cavitation, if there is any cavitation formed during the high temperature melting step.

The consolidation state of the polymeric material is dependent on the amount of fusion between its original particle boundaries (also called 'grain boundaries'), which is dependent on the amount of polymer chains that have diffused from one resin particle to the neighboring resin particles. While elevated temperatures, especially above the melting point of the polymeric material and increased pressure (up to a certain point) can enhance the fusion of neighboring resin particles, fusion can occur at lower temperatures and ambient pressure or under partial pressure or applied vacuum. For example, a UHMWPE resin powder can be placed into a mold, sintered by applying heat and pressure or heat under partial pressure or vacuum, heat at ambient pressure, pressure at ambient temperature or a combination or sequence of these such that a 'pre-molded green' is obtained. This 'pre-molded green' can have some porosity. This porosity can be spatially heterogeneous or homogeneous. The green can also be formed with no load, except that provided by gravity, or under active loading. The latter is achieved by several methods including but not limited to hydrostatic loading, isostatic loading, uniaxial compression, cold isostatic pressing, hot isostatic pressing etc. . . .

Pre-molding to prepare the green can be done by cold isostatic pressing; the sintering or fusion process to prepare the green can be done under hydrostatic pressure at a temperature between room temperature and the melting point of the polymeric material. The pre-molded green can be heated to below or above the melting temperature of the polymeric material for a period of time after the sintering process. Then, the pre-molded and heat treated polymeric material can be completely molded by a compression molding process or by hot isostatic pressing. Hot isostatic pressing can be done under hydrostatic pressure at a temperature above the melting temperature of the polymeric material for a period of time before cooling to at least below the melting temperature of the polymeric material under pressure before releasing the pressure.

By "complete molding" or "completing the molding" is meant to decrease the porosity of the high temperature treated green using pressure and temperature. The completely molded material is expected to be strong enough to be used in total joint applications as a load bearing and/or articular component.

The green preparation or the preparation of the premolded polymeric material can be carried out in air, in vacuum, or in inert gas environment.

What is meant by "green state" is the premolded polymeric material.

The green state can have measurable or non-measurable porosity. In some embodiments the green state has porosity that can be detected by measuring the density of the green. In other embodiments the extent of porosity is very small and its effect on the density is not measurable.

In one embodiment consolidated polymeric material is subjected to high temperature melting. For certain size molded samples there are cracks and cavities that are formed during this high temperature melting step (FIGS. 1 and 2). Subsequently, the high temperature melted sample is further subjected to heat and pressure, for instance by hot isostatic pressing, uniaxial compression, compression molding and other such methods, to heal the cracks and cavities formed in the previous high temperature melting step.

In one embodiment, a polymeric material is placed into a mold and pressurized at elevated temperature below or above the melting point of the polymeric material. It is held in the pressurized and heated state for a time period, then is cooled to about ambient temperature. The cooling can be done under pressure, under a pressure different from the previous pressure, at partial pressure or vacuum. A 'pre-molded green pellet' is thus formed and this step is called 'pre-molding'. This green is then heated to an elevated temperature above the melting point of the polymeric material for a period of time, after which it is cooled to about ambient temperature. The temperature of this process can be above 200° C. for part or all of this time in which case the heating step is called 'high temperature melting'. Then, the heat treated green is placed into a mold and consolidated by heating and pressurizing, after which it is cooled under pressure to at least below the melting temperature of the polymeric material before the pressure is released. This second molding step is called 'secondary molding' or 'complete consolidation'. There can be multiple 'pre-molding' steps and/or heat treatment steps before complete consolidation.

In one embodiment, a polymeric material is placed into a mold and pressurized at elevated temperature below or above the melting point of the polymeric material. It is held in the pressurized and heated state for a time period, then is cooled to about ambient temperature. The cooling can be done under pressure, under a pressure different from the previous pressure, at partial pressure or vacuum. A 'pre-molded green pellet' is thus formed. This green is then heated to an elevated temperature above the melting point of the polymeric material for a period of time, after which it is cooled to about ambient temperature. Then, the heat treated green is placed into a mold and consolidated by heating and pressurizing, after which it is cooled under pressure to at least below the melting temperature of the polymeric material before the pressure is released.

The consolidated polymeric material is exposed to radiation. This irradiated consolidated polymeric material can be heated to below or above the melting temperature of the polymeric material for a period of time. Then, the irradiated consolidated material is cooled to about ambient temperature. Then, the irradiated consolidated polymeric material can be machined into a final implant shape. The implant can be packaged and sterilized using irradiation or non-irradiation techniques such as gas plasma or ethylene oxide sterilization.

In any of the embodiments, the final consolidation step can be performed by fusing a number of pre-molded forms of polymeric materials. It can also be performed using a number of pre-molded forms and not pre-molded resin.

In any of the embodiments, the starting polymer resin can be mixed or blended with an additive such as an antioxidant. Or it can be blended with more than one additive, one or more of which can be antioxidants. For example, the antioxidant blended with the polymeric material can be vitamin E or α-tocopherol. The concentration of any of the additives can be from 0.001 wt % to 99 wt %, or more preferably from 0.01 wt % to 5 wt %, or more preferably 0.1 wt % to 1 wt %, or most preferably about 0.1 wt %, 0.2 wt %, 0.3 wt %, 0.4 wt %, 0.5 wt %.

In any of the embodiments, high temperature melting and its associated processes can be performed as in U.S. Patent Publication No. 2012/0041094, which is incorporated in its entirety as reference.

In one of the embodiments, one or more additive(s) can be incorporated into the consolidated polymeric material after pre-molding, after heat treatment, after complete consolidation, after irradiation, after machining, or after annealing. The incorporation of the additive(s) can be done by diffusion of the additive(s) in pure form, in solution or in emulsion. The incorporation can also be done by a diffusion process followed by heating aimed at homogenizing the additive concentration(s) in the polymeric material.

In one embodiment, a polymeric material is pre-molded. The pre-molded polymeric material is heated to a temperature above the melting point for a period of time or high temperature melted for a period of time. The pre-molded, heat treated polymeric material is completely consolidated. The completely consolidated polymeric material is irradiated. The irradiated consolidated polymeric material is diffused with one or more additive(s). The additive-diffused irradiated consolidated polymeric material can be heated to below or above its melting temperature for a period of time after which it is cooled to about room temperature. The additive-diffused irradiated consolidated polymeric material can be machined to form an implant. Then, the implant can be packaged and sterilized.

In any of the embodiments, the temperature of the heating step can be below or above the melting temperature of the polymeric material. The temperature can be from room temperature to 500° C., more preferably from room temperature to 350° C. It can be 30, 40, 50, 60, 70, 80, 90, 100, 110, 120, 125, 130, 135, 140, 145, 150, 155, 160, 170, 180, 190, 200, 210, 220, 230, 240, 250, 260, 270, 280, 285, 290, 295, 300, 305, 310, 315, 320, 325, 330, 335, 340, or 350° C. The heating environment can be air, inert gas, or a mixture of gases.

In one embodiment, a polymeric material is blended with one or more additives. The blended polymeric material is pre-molded. The pre-molded blended polymeric material is heated to a temperature above the melting point for a period of time or high temperature melted for a period of time. The pre-molded, heat treated blended polymeric material is completely consolidated.

The completely consolidated blended polymeric material is irradiated. The irradiated consolidated blended polymeric material can be heated to below or above its melting temperature for a period of time after which it is cooled to about room temperature. The irradiated consolidated blended polymeric material can be machined to form an implant. Then, the implant can be packaged and sterilized.

In one embodiment, a polymeric material is blended with one or more additives. The blended polymeric material is pre-molded. The pre-molded blended polymeric material is heated to a temperature above the melting point for a period of time or high temperature melted for a period of time. The pre-molded, heat treated blended polymeric material is completely consolidated directly into implant shape by direct compression molding. The direct compression molded blended implant is irradiated. The irradiated direct compression molded blended implant can be packaged and sterilized.

In one embodiment, a polymeric material is blended with one or more additives. The blended polymeric material is pre-molded. The pre-molded blended polymeric material is heated to a temperature above the melting point for a period of time or high temperature melted for a period of time. The pre-molded, heat treated blended polymeric material is completely consolidated directly into implant shape by direct compression molding onto a second material, thereby forming an interlocked hybrid implant. The interlocked hybrid implant is irradiated. The interlocked hybrid implant can be packaged and sterilized.

In some embodiments the direct compression molded polymeric material requires some machining to achieve the final implant shape. For instance direct compression molded tibial inserts are typically molded such that the articular surface is formed during the molding step and the backside locking mechanism features are machined subsequently.

In one embodiment, a polymeric material is blended with one or more additives, where one or more of these additives are cross-linking agents and one or more of these additives are antioxidants. This polymeric material blend is layered with a pre-molded and the high temperature melted polymeric material in a mold and subsequently consolidated together. Several layers of either polymeric material can be used to form a multi-layer structure. The layer made from the pre-molded, high temperature melted polymeric material has excellent mechanical properties and other layer formed by the polymeric material containing the additives has excellent wear resistance. In one example this embodiment is used to create an orthopedic implant where the articular surface and/or the backside surface of the implant consists of the polymeric material with one or more additives, especially at least one peroxide cross-linking agent, to create a cross-linked polymeric material with improved wear resistance. In the same orthopedic implant the bulk consists of the pre-molded, high temperature melted polymeric material with excellent mechanical properties. The resulting implant has excellent wear resistance thanks to the cross-linking of the surfaces and excellent mechanical properties thanks largely to the excellent mechanical properties in the bulk.

In one embodiment pre-molded then high temperature melted, polymeric material containing antioxidant(s) is placed in a mold together with a polymeric material containing an antioxidant and cross-linking agent(s) such as a peroxide. The latter polymeric material may be in the form of powder or in the form of a pre-molded green. The two layers are then direct compression molded such that the polymeric material containing the cross-linking agent(s) constitutes the articular surface of the implant. There may be additional machining steps necessary to achieve the final implant shape after direct compression molding.

In some embodiments, more than one polymeric material containing antioxidant(s) and cross-linking agent(s) are layered with a pre-molded, high temperature melted, polymeric material containing antioxidant(s), such that after direct compression molding the polymeric material containing cross-linking agent(s) is found on more than one surface. For example a tibial insert where the polymeric material with cross-linking agent is found on the articular surface as well as the backside surface of the implant. In such instances the concentration of the cross-linking agents can be varied to achieve different levels of cross-linking on different surfaces. It may be desirable to have a higher cross-link density on the articular surface and a lower cross-link density on the backside surface. Similarly the concentration of the antioxidants may be different between the surface regions in the bulk of the implant. One can achieve this by varying the concentration of the antioxidant(s) in the pre-molded polymeric material and the polymeric material containing cross-linking agent.

Direct compression molding does not always result in the final implant shape. In some embodiments the direct compression molding will form the articular surface but the remaining surfaces of the implant, such as the backside, will need to be machined after direct compression molding. In other embodiments, the direct compression molded polymeric material is in its final implant shape and does not require any additional machining.

In any of the embodiments, the second material onto which compression molding is done can be a metal, more preferably a porous metal.

In any of the embodiments, the antioxidant concentration in a blend of polymeric material or a pre-molded polymeric material or a consolidated polymeric material is from 0.001 wt % to 50 wt %, or from 0.05 wt % to 10 wt %, or from 0.1 wt % to 1 wt %, or 0.2 wt %, or 0.3 wt %, or 0.4 wt %, or 0.5 wt %, or 0.6 wt %, or 0.7 wt %, or 0.8 wt %, or 0.9 wt %, or 1 wt %.

In any of the embodiments, the cross-link agent concentration in a blend of polymeric material or a pre-molded polymeric material or a consolidated polymeric material is from 0.001 wt % to 50 wt %, or from 0.05 wt % to 10 wt %, or from 0.1 wt % to 5 wt %, or 0.2 wt %, or 0.3 wt %, or 0.4 wt %, or 0.5 wt %, or 0.6 wt %, or 0.7 wt %, or 0.8 wt %, or 0.9 wt %, or 1 wt %, or 1.25 wt % or 1.5 wt %, or 2 wt %.

Irradiation: Gamma irradiation or electron radiation may be used. In general, gamma irradiation results in a higher radiation penetration depth than electron irradiation. Gamma irradiation, however, generally provides low radiation dose rate and requires a longer duration of time, which can result in more in-depth and extensive oxidation, particularly if the gamma irradiation is carried out in air. Oxidation can be reduced or prevented by carrying out the gamma irradiation in an inert gas, such as nitrogen, argon, or helium, or under vacuum. Electron irradiation, in general, results in more limited dose penetration depth, but requires less time and, therefore, reduces the risk of extensive oxidation if the irradiation is carried out in air. In addition if the desired dose levels are high, for instance 20 Mrad, the irradiation with gamma may take place over one day, leading to impractical production times. On the other hand, the dose rate of the electron beam can be adjusted by varying the irradiation parameters, such as conveyor speed, scan width, and/or beam power. With the appropriate parameters, a 20 Mrad melt-irradiation can be completed in for instance less than 10 minutes. The penetration of the electron beam depends on the beam energy measured by million electron-volts (MeV). Most polymers exhibit a density of about 1 g/cm$^3$, which leads to the penetration of about 1 cm with a beam energy of 2-3 MeV and about 4 cm with a beam energy of 10 MeV. If electron irradiation is preferred, the desired depth of penetration can be adjusted based on the beam energy. Accordingly, gamma irradiation or electron irradiation may be used based upon the depth of penetration preferred, time limitations and tolerable oxidation levels.

According to certain embodiments, the cross-linked polymeric material can have a melt history, meaning that the polymeric material is melted concurrently with or subsequent to irradiation for cross-linking. According to other embodiments, the cross-linked polymeric material has no such melt history.

(i) Irradiation in the Molten State (IMS):

Melt-irradiation (MIR), or irradiation in the molten state ("IMS"), is described in detail in U.S. Pat. No. 5,879,400. In the IMS process, the polymer to be irradiated is heated to at or above its melting point. Then, the polymer is irradiated. Following irradiation, the polymer is cooled.

Prior to irradiation, the polymer is heated to at or above its melting temperature and maintained at this temperature for a time sufficient to allow the polymer chains to achieve an entangled state. A sufficient time period may range, for example, from about 5 minutes to about 3 hours. For UHMWPE, the polymer may be heated to a temperature between about 145° C. and about 230° C., preferably about 150° C. to about 200° C.

The temperature of melt-irradiation for a given polymer depends on the DSC (measured at a heating rate of 10° C./min during the first heating cycle) peak melting temperature ("PMT") for that polymer. In general, the irradiation temperature in the IMS process is above the peak melting temperature, at least about 2° C. higher than the PMT, more preferably between about 2° C. and about 20° C. higher than the PMT, and most preferably between about 5° C. and about 10° C. higher than the PMT.

In electron beam IMS, the energy deposited by the electrons is converted to heat. This primarily depends on how well the sample is thermally insulated during the irradiation. With good thermal insulation, most of the heat generated is not lost to the surroundings and leads to the adiabatic heating of the polymer to a higher temperature than the irradiation temperature. The heating could also be induced by using a high enough dose rate to minimize the heat loss to the surroundings. In some circumstances, heating may be detrimental to the sample that is being irradiated. Gaseous by-products, such as hydrogen gas when PE is irradiated, are formed during the irradiation. During irradiation, if the heating is rapid and high enough to cause rapid expansion of the gaseous by-products, and thereby not allowing them to diffuse out of the polymer, the polymer may cavitate. The cavitation is not desirable in that it leads to the formation of defects (such as air pockets, cracks) in the structure that could in turn adversely affect the mechanical properties of the polymer and in vivo performance of the device made thereof.

The temperature rise depends on the dose level, level of insulation, and/or dose rate. The dose level used in the irradiation stage is determined based on the desired properties. In general, the thermal insulation is used to avoid cooling of the polymer and maintaining the temperature of the polymer at the desired irradiation temperature. Therefore, the temperature rise can be controlled by determining an upper dose rate for the irradiation. These considerations for optimization for a given polymer of a given size are readily determined by the person of skill in view of the teachings contained herein.

In embodiments of the present invention in which electron radiation is utilized, the energy of the electrons can be varied to alter the depth of penetration of the electrons, thereby controlling the degree of cross-linking and crystallinity following irradiation. The range of suitable electron energies is disclosed in greater detail in International Application WO 97/29793. In one embodiment, the energy is about 0.5 MeV to about 12 MeV. In another embodiment the energy is about 1 MeV to 10 MeV. In another embodiment, the energy is about 10 MeV.

(ii). Cold Irradiation (CIR):

Cold irradiation is described in detail in WO 97/29793. In the cold irradiation process, a polymer is provided at room temperature or below room temperature. Preferably, the temperature of the polymer is about 20° C. Then, the polymer is irradiated. In one embodiment of cold irradiation, the polymer may be irradiated at a high enough total dose and/or at a fast enough dose rate to generate enough heat in the polymer to result in at least a partial melting of the crystals of the polymer. In general, increasing the dose level with CIR would lead to an increase in wear resistance.

Exemplary ranges of acceptable total dosages are disclosed in greater detail in International Application WO 97/29793. In the embodiments below, UHMWPE is used as the starting polymer. In one embodiment, the total dose is about 0.5 MRad to about 1,000 Mrad. In another embodiment, the total dose is about 1 MRad to about 100 MRad. In yet another embodiment, the total dose is about 4 MRad to about 30 MRad. In still other embodiments, the total dose is about 20 MRad or about 15 MRad.

If electron radiation is utilized, the energy of the electrons also is a parameter that can be varied to tailor the properties of the irradiated polymer. In particular, differing electron energies will result in different depths of penetration of the electrons into the polymer. The practical electron energies range from about 0.1 MeV to 16 MeV giving approximate iso-dose penetration levels of 0.5 mm to 8 cm, respectively. A preferred electron energy for maximum penetration is about 10 MeV, which is commercially available through vendors such as Studer (Daniken, Switzerland) or E-Beam Services (New Jersey, USA). The lower electron energies may be preferred for embodiments where a surface layer of the polymer is preferentially cross-linked with gradient in cross-link density as a function of distance away from the surface.

(iii). Warm Irradiation (WIR):

Warm irradiation is described in detail in WO 97/29793. In the warm irradiation process, a polymer is provided at a temperature above room temperature and below the melting temperature of the polymer. Then, the polymer is irradiated. In one embodiment of warm irradiation, which has been termed "warm irradiation adiabatic melting" or "WIAM." In a theoretical sense, adiabatic heating means an absence of heat transfer to the surroundings. In a practical sense, such heating can be achieved by the combination of insulation, irradiation dose rates and irradiation time periods, as disclosed herein and in the documents cited herein. However, there are situations where irradiation causes heating, but there is still a loss of energy to the surroundings. Also, not all warm irradiation refers to an adiabatic heating. Warm irradiation also can have non-adiabatic or partially (such as about 10-75% of the heat generated is lost to the surroundings) adiabatic heating. In all embodiments of WIR, the polymer may be irradiated at a high enough total dose and/or a high enough dose rate to generate enough heat in the polymer to result in at least a partial melting of the crystals of the polymer.

The polymer may be provided at any temperature below its melting point but preferably above room temperature. The temperature selection depends on the specific heat and the enthalpy of melting of the polymer and the total dose level that will be used. The equation provided in International Application WO 97/29793 may be used to calculate the preferred temperature range with the criterion that the final temperature of polymer maybe below or above the melting point. Preheating of the polymer to the desired temperature, for example, about 50° C., about 60° C., about 70° C., about 80° C., about 85° C., about 90° C., about 95° C., about 105° C., about 110° C., about 115° C., or about 125° C., may be done in an inert or non-inert environment.

Exemplary ranges of acceptable total dosages are disclosed in greater detail in International Application WO 97/29793. In one embodiment, the UHMWPE is preheated to about room temperature (about 25° C.) to about 135° C. In one embodiment of WIAM, the UHMWPE is preheated to about 100° C. to just below the melting temperature of the polymer. In another embodiment of WIAM, the UHMWPE is preheated to a temperature of about 100° C. to about 135° C. In yet other embodiments of WIAM, the polymer is preheated to about 120° C. or about 130° C.

In general terms, the pre-irradiation heating temperature of the polymer can be adjusted based on the peak melting temperature (PMT) measure on the DSC at a heating rate of 10° C./min during the first heat. In one embodiment the polymer is heated to about 20° C. to about PMT. In another embodiment, the polymer is preheated to about 90° C. In another embodiment, the polymer is heated to about 100° C. In another embodiment, the polymer is preheated to about 30° C. below PMT and 2° C. below PMT. In another embodiment, the polymer is preheated to about 12° C. below PMT.

In the WIAM embodiment of WIR, the temperature of the polymer following irradiation is at or above the melting temperature of the polymer. Exemplary ranges of acceptable temperatures following irradiation are disclosed in greater detail in International Application WO 97/29793. In one embodiment, the temperature following irradiation is about room temperature to PMT, or about 40° C. to PMT, or about 100° C. to PMT, or about 110° C. to PMT, or about 120° C. to PMT, or about PMT to about 200° C. In another embodiment, the temperature following irradiation is about 145° C. to about 190° C. In yet another embodiment, the temperature following irradiation is about 145° C. to about 190° C. In still another embodiment, the temperature following irradiation is about 150° C.

In WIR, gamma irradiation or electron radiation may be used. In general, gamma irradiation results in a higher dose penetration depth than electron irradiation. Gamma irradiation, however, generally requires a longer duration of time, which can result in more in-depth oxidation, particularly if the gamma irradiation is carried out in air. Oxidation can be reduced or prevented by carrying out the gamma irradiation in an inert gas, such as nitrogen, argon, or helium, or under vacuum. Electron irradiation, in general, results in more limited dose penetration depths, but requires less time and, therefore, reduces the risk of extensive oxidation. Accordingly, gamma irradiation or electron irradiation may be used based upon the depth of penetration preferred, time limitations and tolerable oxidation levels. In the WIAM embodiment of WIR, electron radiation is used.

Ranges of acceptable dose rates are exemplified in greater detail in International Application WO 97/29793. In any of the irradiation methods described above, the dose rates will vary between 0.5 Mrad/pass and 50 Mrad/pass. The upper limit of the dose rate depends on the resistance of the polymer to cavitation/cracking induced by the irradiation. In any of the irradiation methods described above, the radiation dose can be from 0.001 MRad to 100000 MRads, preferably from 1 MRad (10 kGy) to 30 MRad (300 kGy), or 25 kGy, or 150 kGy or 175 kGy.

In any of the embodiments above, irradiation, cross-linking, doping, heating, annealing or high temperature melting of a pre-molded polymeric material or polymeric material in the resin form, or polymeric material in the completely consolidated form can be done in multiple steps, in any order or repeated steps in any order.

BRIEF DESCRIPTION OF THE DRAWINGS

FIG. 1. Defects in a consolidated 0.1 wt % vitamin E-blended UHMWPE after consolidation and high temperature exposure at 330° C. for 6 hours (a). A crossection of a cylinder is shown. The original cylinder subjected to processing was 6.7 cm in diameter and 5.6 cm in height (b). The dashed line denotes where the crossection was taken.

FIG. 2. Examples of defects in different consolidated forms of UHMWPE. All samples were exposed to 320° C. for 6 hours. (a, b) 0.1 wt % vitamin E blended UHMWPE, cylindrical, direct compression molded pucks (67 mm diameter, 56 mm in height); (c) 0.2 wt % vitamin E blended UHMWPE, direct compression molded rectangular block (30 mm in height); (d) virgin (no additive) UHMWPE, barstock from compression molded sheet (89 mm in width, 89 mm in length, approximately 150 mm in height); (e) virgin (no additive) UHMWPE, ram extruded barstock (approximately 150 mm in height).

DETAILED DESCRIPTION OF THE INVENTION

Figure 3:
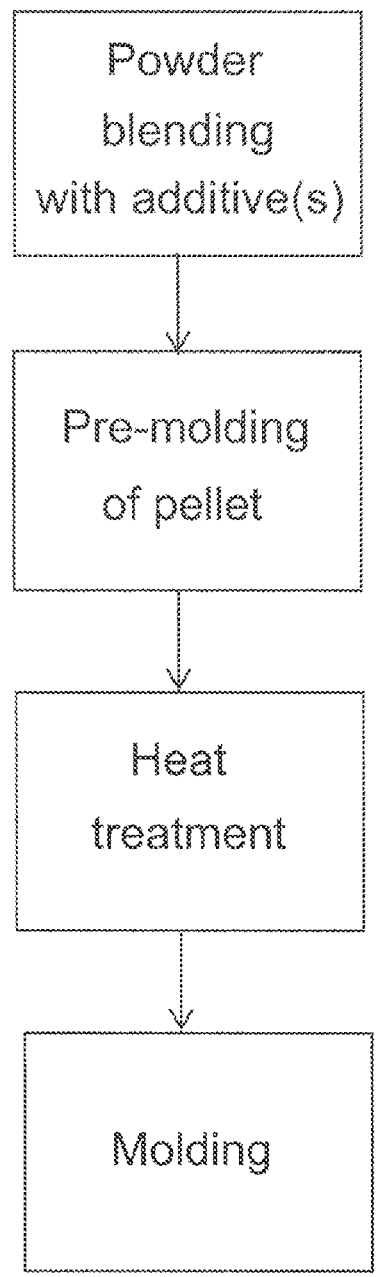
FIG. 3. Schematic description of process which includes a step for pre-molding of pellet before high temperature treatment and second molding.

This invention comprises methods of making oxidation and wear resistant polymeric materials using peroxide cross-linking and high temperature melting process. The invention also comprises a multiple step procedure for enabling the manufacturing of such material without size limitations.

Definitions

The term "additive" refers to any material that can be added to a base polymer in less than 50 v/v %. This material can be an organic or inorganic material with a molecular weight less than that of the base polymer. An additive can impart different properties to the polymeric material, for example, it can be a nucleating agent, a cross-linking agent or an antioxidant.

Peroxide initiation or decomposition temperature ($T_p$): means the temperature at which the peroxide dissociates/decomposes substantially into free radicals which can initiate other reactions, for example at least 0.1%, more preferably at least 10%, or most preferably at least 50% within 1 hour into the free radical(s) that initiate cross-linking in the polymer. Organic peroxides are commonly characterized by their half-lives, i.e., the time it takes for half of a quantity of given peroxide in a given solution to decompose in 1 hour ($T_1$) or 10 hours ($T_{10}$). The peroxide initiation temperature, $T_p$, is used generally interchangeably with decomposition temperature, which may be, for example, 5° C. or 10° C. below or 5° C. or 10° C. above the temperature corresponding to the half-life in 10 hours ($T_{10}$) or to the half-life in 1 hour ($T_1$). This difference may be because the presence of the peroxide in the polymer rather than that in solution. Peroxide initiation or decomposition temperature can be in the range from −20° C. to 500° C., preferably from 0° C. to 200° C., more preferably from 30° C. to 190° C. It can be 30° C., 35° C., 40° C., 45° C., 50° C., 55° C., 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., 150° C., 155° C., 160° C., 165° C., 170° C., 175° C., 180° C., 185° C., 190° C., 195° C., 200° C., 205° C., 210° C., 215° C., 220° C., 225° C., 230° C., 235° C., 240° C., 245° C., 250° C., 255° C., 260° C., 265° C., 270° C., 275° C., 280° C., 285° C., 290° C., 295° C., 300° C., 305° C., 310° C., 315° C., or 320° C.

Peroxides are a group of chemicals with the peroxide functional group. General peroxide categories include inorganic peroxides, organic peroxides, diacyl peroxides, peroxyesters, peoxydicarbonates, dialkyl peroxides, ketone peroxides, peroxyketals, cyclic peroxides, peroxymonocarbonates and hydroperoxides. They contain an easily breakable 0-0 bond that can dissociate/decompose into free radicals when heated and cause cross-linking in polyolefins; therefore peroxides are referred to as part of a family of "cross-linking agents" in this application. Peroxides in this invention can be selected from any peroxide, for example, benzoyl peroxide, dicumyl peroxide, methyl ethyl ketone peroxide, acetone peroxide, 2,5-Di(tert-butylperoxy)-2,5-dimethyl-3-hexyne (Luperox® 130), 3,3,5,7,7-pentamethyl-1,2,4 trioxepane (Trigonox®311), etc. or mixtures thereof. Other examples of peroxides are dilauryl peroxide, methyl ether ketone peroxide, t-amyl peroxyacetate, t-butyl hydroperoxide, t-amyl peroxybenzoate, D-t-amyl peroxide, 2,5-Dimethyl 2,5-Di(t-butylperoxy)hexane, t-butylperoxy isopropyl carbonate, succinic acid peroxide, cumene hydroperoxide, 2,4-pentanedione peroxide, t-butyl perbenzoate, diethyl ether peroxide, acetone peroxide, arachidonic acid 5-hydroperoxide, carbamide peroxide, tert-butyl hydroperoxide, t-butyl peroctoate, t-butyl cumyl peroxide, Di-sec-butyl-peroxydicarbonate, D-2-ethyl hexylperoxydicarbonate, 1,1-Di(t-butylperoxy)cyclohexane. Other examples of peroxides are members of the Luperox® family supplied by Arkema. Other examples of peroxides are 1,1-Di(tert-butylperoxy)-3,3,5-trimethylcyclohexane, 2,5-Dimethyl-2,5-di(tert-butylperoxy)hexane, 3,3,5,7,7-Pentamethyl-1,2,4-trioxepane, Butyl 4,4-di(tert-butylperoxy) valerate, Di(2,4-dichlorobenzoyl) peroxide, Di(4-methylbenzoyl) peroxide, Di(tert-butylperoxyisopropyl) benzene, tert-Butyl cumyl peroxide, tert-Butyl peroxy-3,5, 5-trimethylhexanoate, tert-Butyl peroxybenzoate, tert-Butylperoxy 2-ethylhexyl carbonate. Other examples of peroxides are members of the Trigonox™ or Perkadox™ family supplied by Akzo Nobel.

A crosslinking agent is a compound which can cause cross-linking in polymeric materials. Most often, cross-linking of the polymer follows a trigger which initiates the cross-linking process. For example, in the case of peroxides, heating to a temperature where the peroxide decomposes into free radicals, which are then transferred onto the polymer and initiate recombination reactions causing cross-linking is required. In other cases, other stimuli may be used to trigger the reaction such as the application of ultraviolet light, heat, pressure or vacuum, contact with a particular solvent, or irradiation or combinations thereof. In some embodiments, the cross-linking agents used are those that are commercially available and may contain impurities. In some embodiments, the cross-linking agents may be 100% pure or less. In some embodiments, the cross-linking agents are 80%, 85%, 90%, 91%, 92%, 93%, 94%, 95%, 96%, 97%, 98%, or 99% pure.

The definition of crosslinking agent herein differs somewhat from what is known in the art. Typically, a crosslinking agent is defined as a compound which can chemically attach to two or more points on the polymeric material, creating a linkage between the same or different polymer chains. We are using a more general, expanded definition where the crosslinking agent is a compound that initiates the processes that leads to the crosslinking of the polymeric material and the compound may or may not itself chemically or ionically attach to the polymer. For instance, the cross-linking agent may have a free radical, which may abstract a hydrogen from the polymeric material, creating a free radical on the polymeric material; subsequently such free radicals on the polymeric material can react with each other to form a cross-link without chemically attaching the cross-linking agent to the polymeric material. The cross-linking agent may also form covalent or ionic bonding with one or more sites on the polymeric material, thereby causing grafting or cross-linking. In this case, the cross-linking agent becomes part of the cross-linked polymeric material. In some embodiments, there are unreacted cross-linking agent and/or the byproducts of the cross-linking agent in the polymeric material. In some embodiments these unreacted cross-linking agent and/or the byproducts of the cross-linking agent are partially or fully extracted from the polymeric material after cross-linking. This extraction, among other methods, can include solvent extraction, emulsified solvent extraction, heat extraction, supercritical fluid extraction, and/or vacuum extraction. For instance, in some embodiments supercritical carbon dioxide extraction is used. In other embodiments, extraction by placing the polymeric material under vacuum with or without heat is used. For instance, a cross-linking agent fo UHMWPE may be a peroxide.

The term "antioxidant" refers to what is known in the art as (see, for example, WO 01/80778, U.S. Pat. No. 6,448, 315). Alpha- and delta-tocopherol; propyl, octyl, or dedocyl gallates; lactic, citric, ascorbic, tartaric acids, and organic acids, and their salts; orthophosphates, lycopene, tocopherol acetate are generally known form of antioxidants. Antioxidants are also referred as free radical scavengers, include: glutathione, lipoic acid, vitamins such as ascorbic acid (vitamin C), vitamin B, vitamin D, vitamin-E, tocopherols (synthetic or natural, alpha-, gamma-, delta-), acetate vitamin esters, water soluble tocopherol derivatives, tocotrienols, water soluble tocotrienol derivatives; melatonin, carotenoids, including various carotenes, lutein, pycnogenol, glycosides, trehalose, polyphenols and flavonoids, quercetin, lycopene, lutein, selenium, nitric oxide, curcuminoids, 2-hydroxytetronic acid; cannabinoids, synthetic antioxidants such as tertiary butyl hydroquinone, 6-amino-3-pyrodinoles, butylated hydroxyanisole, butylated hydroxytoluene, ethoxyquin, tannins, propyl gallate, other gallates, Aquanox family; Irganox® and Irganox® B families including Irganox® 1010, Irganox® 1076, Irganox® 1330; Irgafos® family including Irgafos® 168; phenolic compounds with different chain lengths, and different number of OH groups; enzymes with antioxidant properties such as superoxide dismutase, herbal or plant extracts with antioxidant properties such as St. John's Wort, green tea extract, grape seed extract, rosemary, oregano extract, mixtures, derivatives, analogues or conjugated forms of these. Antioxidants/free radical scavengers can be primary antioxidants with reactive OH or NH groups such as hindered phenols or secondary aromatic amines, they can be secondary antioxidants such as organophosphorus compounds or thiosynergists, they can be multifunctional antioxidants, hydroxylamines, or carbon centered radical scavengers such as lactones or acrylated bis-phenols. The antioxidants can be selected individually or used in any combination.

Irganox®, as described herein refers to a family of antioxidants manufactured by Ciba Specialty Chemicals. Different antioxidants are given numbers following the Irganox® name, such as Irganox® 1010, Irganox® 1035, Irganox® 1076, Irganox® 1098, etc. Irgafos® refers to a family of processing stabilizers manufactured by Ciba Specialty Chemicals. Irganox® family has been expanded to include blends of different antioxidants with each other and with stabilizers from different families such as the Irgafos family. These have been given different initials after the Irganox® name, for instance, the Irganox® HP family are synergistic combinations of phenolic antioxidants, secondary phosphate stabilizers and the lactone Irganox® HP-136. Similarly, there are Irganox® B (blends), Irganox® L (aminic), Irganox® E (with vitamin E), Irganox® ML, Irganox® MD families. Herein we discuss these antioxidants and stabilizers by their tradenames, but other chemicals with equivalent chemical structure and activity can be used. Addition, these chemicals can be used individually or in mixtures of ant composition. Some of the chemical structures and chemical names of the antioxidants in the Irganox® family are listed in Table 1.

TABLE 1

Chemical names and structures of some antioxidants trademarked under the Irganox ® name.

| Tradename | Chemical name | Chemical Structure |
|---|---|---|
| Irganox ®1010 | Tetrakis[methylene(3,5-di-tert-butylhydroxyhydrocinnamate)]methane | 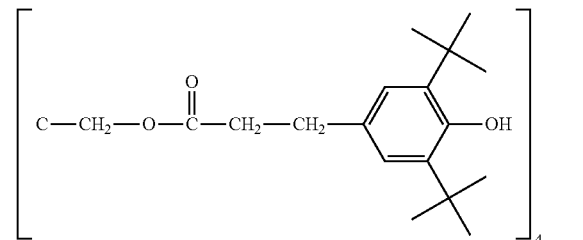 1178 g/mol |
| Irganox ®1035 | Thiodiethylene bis[3-[3,5-di-tert-butyl-4-hydroxyphenyl]propionate] | 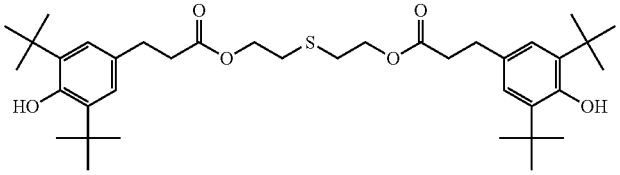 [SMILES: CC(C)(C)c1cc(CCC(=O)OCCSCCOC(=O)CCc2cc(C(C)(C)C)c(O)c(C(C)(C)C)c2)cc(C(C)(C)C)c1O] |

TABLE 1-continued

Chemical names and structures of some antioxidants trademarked under the Irganox ® name.

| Tradename | Chemical name | Chemical Structure |
|---|---|---|
| Irganox ®1076 | Octadecyl 3,5-di-tert-butyl-4-hydroxylhydrocinnamate | 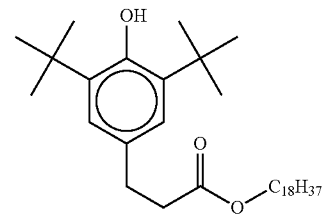 |
| Irganox ®1098 | N,N'-hexane-1,6-diylbis(3-(3,5-di tert-butyl-4-hydroxyphenylpropionamide)) | |
| Irganox ®1135 | Benzenepropanoic acid, 3,5-bis (1,1-dimethyl-ethyl)-4-hydroxy-C7-C9 branched alkyl esters | 309 g/mol |
| Irganox ®1330 | 1,3,5-tris(3,5-di-tert-butyl-4-hydroxybenzyl)-2,4,6-trimethylbenzene | 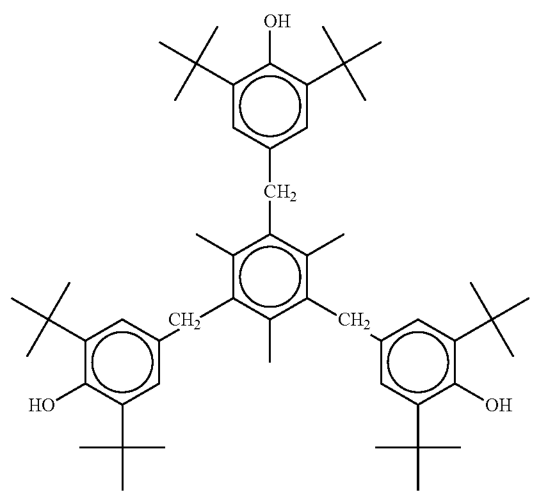 |
| Irganox ®1520 | | 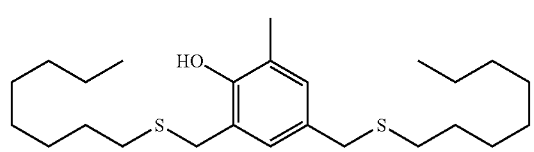 [SMILES: CCCCCCCCSCc1cc(C)c(O)c(CSCCCCCCCC)c1] |
| Irganox ®1726 | 2,4-bis(dodecylthiomelhyl)-6-methylphenol | 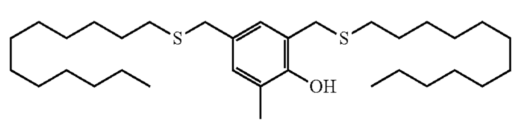 [SMILES: CCCCCCCCCCCCSCc1cc(C)c(O)c(CSCCCCCCCCCCCC)c1] |
| Irganox ®245 | Triethylene glycol bis(3-tert-butyl-4-hydroxy-5-methylphenyl)propionate | 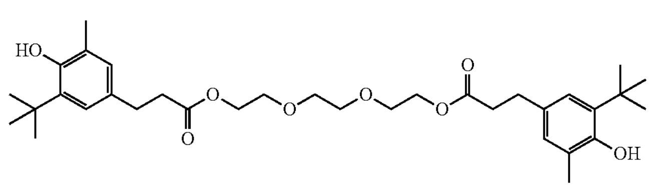 [SMILES: Cc1cc(CCC(=O)OCCOCCOCCOC(=O)CCc2cc(C)c(O)c(C(C)(C)C)c2)cc(C(C)(C)C)c1O] |

TABLE 1-continued

*Chemical names and structures of some antioxidants trademarked under the Irganox ® name.*

| Tradename | Chemical name | Chemical Structure |
|---|---|---|
| Irganox ®3052 | 2,2'-methylenebis(4-methyl-6-tert-butylphenol)monoacrylate | 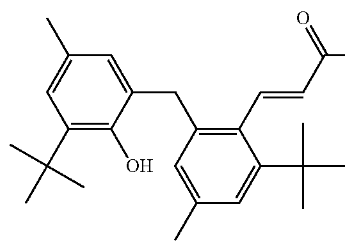 |
| Irganox ®3114 | 1,3,5-TRis(3,5-di-tert-butyl-4-hydroxybenzyl)-1,3,5-triazine-2,4,6(1H,3H,5H)-trione | 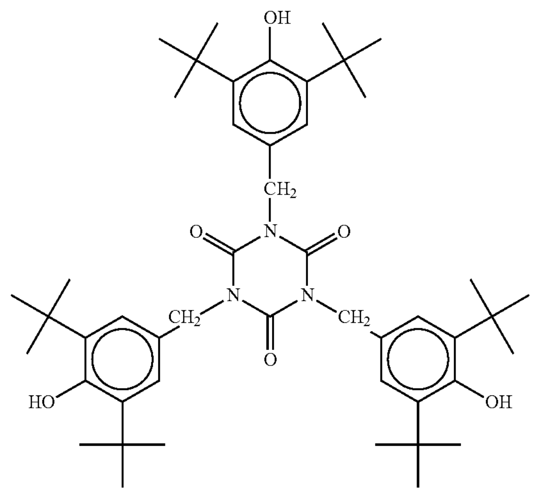 |
| Irganox ®5057 | Benzenamine,N-phenyl-,reaction products with 2,4,4-trimethylpentene | R, $R_1$ = H, $C_4H_9$, or $C_8H_{17}$ and other alkyl chains |
| Irganox ®565 | 2,4-bis(octylthio)-6-(4-hydroxy-3,5-di-tert-butylanilino)-1,3,5-triazine | 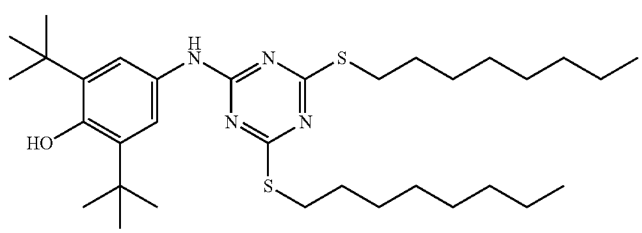 [SMILES: CCCCCCCCSc1nc(Nc2cc(C(C)(C)C)c(O)c(C(C)(C)C)c2)nc(SCCCCCCCC)n1] |
| Irganox ®HP-136 | 5,7-di-t-butyl-3-(3,4 di-methylphenyl)-3H-benzofuran-2-one | 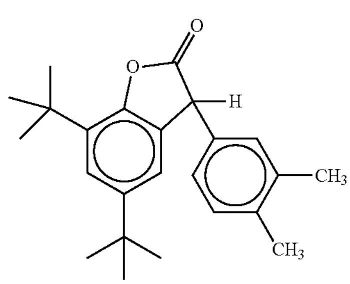 |

TABLE 1-continued

Chemical names and structures of some antioxidants trademarked under the Irganox ® name.

| Tradename | Chemical name | Chemical Structure |
| --- | --- | --- |
| Irgafos ®168 | Tris(2,4-di-tert-butylphenyl)phospite | 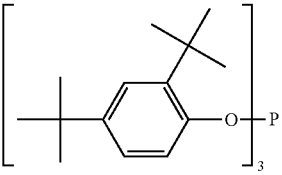<br>646.9 g/mol |

The term 'blending' generally refers to mixing of a polymeric material in its pre-consolidated form with an additive. If both constituents are solid, blending can be done by using other component(s) such as a liquid to mediate the mixing of the two components, after which the liquid is removed by evaporating. If the additive is liquid, for example α-tocopherol, then the polymeric material can be mixed with large quantities of liquid. This high concentration blend can be diluted down to desired concentrations with the addition of lower concentration blends or virgin polymeric material without the additive to obtain the desired concentration blend. Or the polymeric material can be mixed with enough liquid additive to obtain the desired concentration in the polymeric material. In the case where an additive is also an antioxidant, for example vitamin E, or α-tocopherol, then blended polymeric material is also antioxidant-doped.

In one embodiment UHMWPE flakes are blended with α-tocopherol; preferably the UHMWPE/α-tocopherol blend is heated to diffuse the α-tocopherol into the flakes. This blend is then subjected to further treatment such as partial or complete molding and heat treatment.

In some embodiments the cross-linking agent(s) and antioxidant(s) are blended together to form a cross-linking agent/antioxidant blend. The said cross-linking agent/antioxidant blend is then blended with polymeric material to obtain a polymeric material/cross-linking agent/antioxidant blend.

The term 'consolidation' refers generally to processes used to convert the polymeric material resin, particles, flakes, i.e. small pieces of polymeric material into a mechanically integral large-scale solid form, which can be further processed, by for example machining in obtaining articles of use such as medical implants. Methods such as injection molding, extrusion, compression molding, isostatic pressing (hot or cold), etc. can be used. In the present invention the pre-molded green polymeric material is poorly consolidated; that is the consolidation is not taken to its full extent. In the case of the green, the green also has porosity more than what is present in well-functioning medical implants made from the same polymeric material.

In the case of UHMWPE, consolidation is most often performed by "compression molding". In some instances consolidation can be interchangeably used with compression molding. The molding process generally involves:
  i. heating the polymeric material to be molded,
  ii. pressurizing the polymeric material while heated,
  iii. keeping at temperature and pressure, and
  iv. cooling down and releasing pressure.

Heating of the polymeric material can be done at any rate. Temperature can be increased linearly with time or in a step-wise fashion or at any other rate. Alternatively, the polymeric material can be placed in a pre-heated environment. The mold for the consolidation can be heated together or separately from the polymeric material to be molded. Steps (i) and (ii), i.e. heating and pressurizing before consolidation can be done in multiple steps and in any order.

For example, polymeric material can be pressurized at room temperature to a set pressure level 1, after which it can be heated and pressurized to another pressure level 2, which still may be different from the pressure or pressure(s) in step (iii). Step (iii), where a high temperature and pressure are maintained is the 'dwell period' where a major part of the consolidation takes place. One temperature and pressure or several temperatures and pressures can be used during this time without releasing pressure at any point. For example, dwell temperatures in the range of 135 to 350° C. and dwell pressures in the range of 0.1 MPa to 100 MPa or up to 1000 MPa can be used. The dwell time can be from 1 minute to 24 hours, more preferably from 2 minutes to 1 hour, most preferably about 10 minutes. The temperature(s) at step (iii) are termed 'dwell' or 'molding' temperature(s). The pressure(s) used in step (iii) are termed 'dwell' or 'molding' pressure(s). The order of cooling and pressure release (step iv) can be used interchangeably. In some embodiments the cooling and pressure release may follow varying rates independent of each other. In some embodiments, consolidation of polymeric resin or blends of the resin with additive(s) are achieved by compression molding. The dwell temperature and dwell time for consolidation can be changed to control the amount of integration.

In this invention, we also describe 'partial consolidation' or 'partially consolidated' or 'pre-molded' polymeric material, which refers to a state of the polymeric material which is less integrated than a 'completely consolidated' form of the polymeric material. The extent of integration can be quantified, for example, by measuring the elongation at break of the polymeric materials after consolidation. In general, a lower elongation at break indicates a less integrated or less consolidated state for the same type of polymeric resin. In general, a partially consolidated polymeric material may not have the required properties to be used as a final product and needs to be further integrated or processed or consolidated to increase its state of consolidation and/or to reduce its porosity. In pre-molding, temperature and pressure steps can be applied separately. Also in pre-molding, ambient pressure, partial pressure below ambient to reduce oxygen concentration, or vacuum can be used. Also the pre-molding step can be performed in air or in inert gas or a mixture thereof. The inert gas can be argon, helium, nitrogen or a mixture thereof. For example, dwell temperatures in the range of 0° C. to 350° C. and dwell pressures in the range of 0.001 MPa to 100 MPa or up to 1000 MPa can be used. The dwell time can be from 1 minute to 24 hours, more preferably from 2 minutes to 1 hour, most preferably about 5 minutes.

Compression molding can also be done by "layered molding". This refers to consolidating a polymeric material by compression molding one or more of its pre-molded and resin forms, which may be in the form of flakes, powder, pellets or the like or consolidated or pre-molded forms in layers. This may be done such that there can be distinct regions in the consolidated form containing different concentrations of additives such as antioxidant(s) or crosslinking agent(s). Whenever a layered-molded polymeric material is described in the examples below and is used in any of the embodiments, it can be fabricated by:
 (a) layered molding of a pre-molded polymeric material with polymeric resin powder or its antioxidant/cross-linking agent blends where one or more layers contain no crosslinking agent(s) and one or more layers contain one or more additives;
 (b) molding together of pre-molded layers of polymeric material containing different or identical concentration of additives such as antioxidant(s) and crosslinking agent(s).

One or more of the layers can be treated before or during molding by heating, or high temperature melting. The layer or layers to be molded can be heated in liquid(s), in water, in air, in inert gas, in supercritical fluid(s) or in any environment containing a mixture of gases, liquids or supercritical fluids before pressurization. The layer or layers can be pressurized individually at room temperature or at an elevated temperature below the melting point or above the melting point before being molded together. The temperature at which the layer or layers are pre-heated can be the same or different from the molding or dwell temperature(s). The temperature can be gradually increased from pre-heat to mold temperature with or without pressure. The pressure to which the layers are exposed before molding can be gradually increased or increased and maintained at the same level.

During consolidation, different regions of the mold can be heated to different temperatures. The temperature and pressure can be maintained during molding for 1 second up to 1000 hours or longer. During cool-down under pressure, the pressure can be maintained at the molding pressure or increased or decreased. The cooling rate can be 0.0001° C./minute to 120° C./minute or higher. The cooling rate can be different for different regions of the mold. After cooling down to about room temperature, the mold can be kept under pressure for 1 second to 1000 hours. Or the pressure can be released partially or completely at an elevated temperature.

In some embodiments, the consolidated polymeric material is fabricated through "direct compression molding" (DCM), which is compression molding using parallel plates or any plate/mold geometry which can directly result in an implant or implant preform. Preforms are generally oversized versions of implants, where some machining of the preform can give the final implant shape. In some embodiments certain features of the final implant shape may be machined after direct compression molding.

In some embodiments, the pre-molded polymeric material is subjected to high temperature melting and subsequently direct compression molded. The direct compression molded polymeric material may be in its final implant shape. In some embodiments certain features of the final implant shape may be machined after direct compression molding. In certain embodiments, the pre-molded polymeric material contains cross-linking agents. In some embodiments the pre-molded polymeric material is subjected to irradiation before the subsequent direct compression molding.

Compression molding can also be done such that the polymeric material is directly compression molded onto a second surface, for example a metal or a porous metal to result in an implant or implant preform. This type of molding results in a "hybrid interlocked polymeric material" or "hybrid interlocked medical implant preform" or "hybrid interlocked medical implant". Molding can be conducted with a second piece, for example a metal, that becomes an integral part of the consolidated polymeric article. For example, a combination of antioxidant-containing polyethylene resin, powder, or flake and virgin polyethylene resin, powder or flake is direct compression molded into a metallic acetabular cup or a tibial base plate. The porous tibial metal base plate is placed in the mold, antioxidant blended polymeric resin, powder, or flake is added on top. Prior to consolidation, the pores of the metal piece can be filled with a waxy or plaster substance through half the thickness to achieve polyethylene interlocking through the other unfilled half of the metallic piece. The pore filler is maintained through the irradiation and subsequent processing (for example peroxide diffusion) to prevent infusion of components in to the pores of the metal.

In some embodiments, the article is machined after processing to shape an implant. In some embodiments, there is more than one metal piece integral to the polymeric article. The metal(s) may be porous only in part or non-porous. In another embodiment, one or some or all of the metal pieces integral to the polymeric article is a porous metal piece that allows bone in-growth when implanted into the human body. In one embodiment, the porous metal of the implant is sealed using a sealant to prevent or reduce the infusion of antioxidant/peroxide (in diffusion steps after consolidation) into the pores during the selective doping of the implant. Preferably, the sealant is water soluble. But other sealants are also used. The final cleaning step that the implant is subjected to also removes the sealant. Alternatively, an additional sealant removal step is used. Such sealants as water, saline, aqueous solutions of water soluble polymers such as poly-vinyl alcohol, water soluble waxes, plaster of Paris, or others are used. In addition, a photoresist like SU-8, or other, may be cured within the pores of the porous metal component. Following processing, the sealant may be removed via an acid etch or a plasma etch. In these embodiments, the polymeric material, which is molded directly onto a second surface to form the hybrid interlocked polymeric material, maybe a pre-molded polymeric material with or without additives and/or cross-linking agents. In such embodiments the pre-molded polymeric material may be subjected to high temperature melting and/or radiation cross-linking.

The term 'cross-linking' refers to what is known in the art as processes that result in the covalent bonding of the parts of a material, for example polymer chains in a polymeric material. In the case of UHMWPE, which is a semi-crystalline polymer, there is covalent bonding of the polymer chains of the polymeric material. For instance, the cross-link density of polyolefins, such as polyethylene is measured by swelling a roughly 3×3×3 mm cube of polymeric material in xylene. The samples are weighed before swelling in xylene at 130° C. for 2 hours and they are weighed immediately after swelling in xylene. The amount of xylene uptake is determined gravimetrically, then converted to volumetric uptake by dividing by the density of xylene; 0.75 g/cc. By assuming the density of polyethylene to be approximately 0.94 g/cc, the volumetric swell ratio of cross-linked UHMWPE is then determined. The cross-link density is calculated by using the swell ratio as described in Oral et al., *Biomaterials* 31: 7051-7060 (2010) and is reported in mol/ $m^3$. The term 'highly cross-linked' refers generally to the state of the polymeric material where there is further cross-linking and the cross-link density is higher than that of 'substantially cross-linked' polymeric material. The term 'cross-linked' refers to the state of polymeric material that is cross-linked to any level, for instance substantial cross-linked or highly cross-linked states.

The term 'wear' refers to the removal of material from the polymeric material during articulation or rubbing against another material. For UHMWPE, wear is generally assessed gravimetrically after an initial creep deformation allowance in number of cycles of motion. The term 'wear resistant' refers to the state of a polymeric material where it has low wear. For example, the wear rate is tested on cylindrical pins (diameter 9 mm, length 13 mm) on a bidirectional pin-on-disc wear tester in undiluted bovine calf serum at 2 Hz in a rectangular pattern (5 mm×10 mm) under variable load with a maximum of 440 lbs as described in Bragdon et al. (J Arthroplasty 16: 658-665 (2001)). Initially, the pins are subjected to 0.5 million cycles (MC), after which they are tested to 1.25 million cycles with gravimetric measurements approximately every 0.125 MC. The wear rate is determined by the linear regression of the weight loss as a function of number of cycles from 0.5 to 1.25 MC. The term "highly wear resistant" refers to the state of a polymeric material with a wear rate of less than 3 mg/million-cycles under these conditions.

The term "surface" of a polymeric material refers generally to the exterior region of the material having a thickness of about 1.0 µm to about 2 cm or more, preferably about 1.0 mm to about 5 mm, more preferably about 2 mm of a polymeric material or a polymeric sample or a medical device comprising polymeric material. Surface may also refer to multiple regions in the exterior of the polymeric material.

The term "bulk" of a polymeric material refers generally to an interior region of the material having a thickness of about 1.0 µm to about 2 cm or more, preferably about 1.0 mm to about 5 mm, more preferably about 2 mm, from the surface of the polymeric material to the center of the polymeric material. However, the bulk may include selected sides or faces of the polymeric material including any selected surface.

Although the terms "surface" and "bulk" of a polymeric material generally refer to exterior regions and the interior regions, respectively, there generally is no discrete boundary between the two regions. But, rather the regions are more of a gradient-like transition. These can differ based upon the size and shape of the object and the resin used.

The term 'doping' refers to a process known in the art (see, for example, U.S. Pat. Nos. 6,448,315 and 5,827,904). In this connection, doping generally refers to contacting a polymeric material with a component or the solution/emulsion of a component under certain conditions, as set forth herein, for example, doping UHMWPE with an antioxidant under supercritical conditions. "Doping" also refers to introducing additive(s) into the base polymeric material in quantities less than 50 v/v %. A polymeric material treated in such a way, for example, to incorporate an antioxidant is termed as an "antioxidant-doped" polymeric material. The polymeric material can be "doped" by other additives as well, such as a crosslinking agent, in which case the polymeric material treated in such a way may be termed as "crosslinking agent-doped" polymeric material. Alternatively, if the polymeric material is doped by one or more peroxides, it may be termed "peroxide-doped" polymeric material.

Doping may also be done by diffusing an additive into the polymeric material by immersing the polymeric material in additive, by contacting the polymeric material with additive in the solid state, by contacting the polymeric material with a bath of additive in the liquid state, or by contacting the polymeric material with a mixture of the additive in one or more solvents in solution, emulsion, suspension, slurry, aerosol form, or in a gas or in a supercritical fluid. The doping process by diffusion can involve contacting a polymeric material, a preform, medical implant or device with an additive, such as 2,5-dimethyl-2,5-Di-(t-butylperoxy) hexyne-3 (Luperox® 130), for about an hour up to several days, preferably for about one hour to 24 hours, more preferably for one hour to 16 hours. The doping time can be from a second to several weeks, or it can be 1 minute to 24 hours, or it can be 15 minutes to 24 hours in 15 minute intervals. The medium for the diffusion of the additive (bath, solution, emulsion, paste, slurry and the like) can be heated to room temperature or up to about 200° C. or more and the doping can be carried out at room temperature or up to about 200° C. or more. Preferably, the antioxidant can be heated to 100° C. and the doping is carried out at 100° C. Or the doping can be carried out at 20° C. 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., 150° C., 155° C., 160° C., 165° C., 170° C., 175° C., 180° C., 185° C., 190° C., 195° C., 200° C., 205° C., 210° C., 215° C., 220° C., 230° C., 240° C., 250° C., 260° C., 270° C., 280° C., 290° C., 300° C., 320° C. or 340° C.

The doped polymeric material can be annealed (heated) by heating below or above the melting point of the polymeric material subsequent to doping. The annealing is preferably for about an hour up to several days, more preferably for about one hour to 24 hours, most preferably for one hour to 16 hours. The doping time can be from a second to several weeks, or it can be 1 minute to 24 hours, or it can be 15 minutes to 24 hours in 15 minute intervals. The doped polymeric material can be heated to room temperature or up to about 350° C. and the annealing can be carried out at room temperature or up to about 350° C. Preferably, the doped polymeric material can be heated to 120° C. and the annealing is carried out at 120° C. Or annealing can be carried out at 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., 150° C., 155° C., 160° C., 165° C., 170° C., 175° C., 180° C., 185° C., 190° C., 195° C., 200° C., 205° C., 210° C., 215° C., 220° C., 225° C., 230° C., 235° C., 240° C., 245° C., 250° C., 255° C., 260° C., 265° C., 270° C., 275° C., 280° C., 285° C., 290° C., 295° C., 300° C., 315° C., 320° C., 325° C., 330° C., 335° C. or 340° C. In the case of a "peroxide-doped" polymeric material, annealing can cause cross-linking if the temperature(s) used during annealing is close to or above the peroxide initiation temperature(s). Annealing can be performed in liquid(s), in air, in other gases such as oxygen, in inert gas, in supercritical fluid(s), in a sensitizing environment or in vacuum. Annealing can also be performed in ambient pressure, above ambient pressure, or below ambient pressure. Annealing can also be performed while the polymeric material is immersed in liquid antioxidant, such as vitamin E, or a solution/emulsion of antioxidant(s).

A "sensitizing environment" or "sensitizing atmosphere" refers to a mixture of gases and/or liquids (at room temperature) that contain sensitizing gases and/or liquid component(s) that can react with residual free radicals to assist in the recombination of the residual free radicals. The gases maybe acetylene, chloro-trifluoro ethylene (CTFE), ethylene, or like. The gases or the mixtures of gases thereof may contain noble gases such as nitrogen, argon, neon and like. Other gases such as, carbon dioxide or carbon monoxide may also be present in the mixture. In applications where the surface of a treated material is machined away during the device manufacture, the gas blend could also contain oxidizing gases such as oxygen. The sensitizing environment can be dienes with different number of carbons, or mixtures of liquids and/or gases thereof. An example of a sensitizing liquid component is octadiene or other dienes, which can be mixed with other sensitizing liquids and/or non-sensitizing liquids such as a hexane or a heptane. A sensitizing environment can include a sensitizing gas, such as acetylene, ethylene, or a similar gas or mixture of gases, or a sensitizing liquid, for example, a diene. The environment is heated to a temperature ranging from room temperature to a temperature below the melting point of the material.

In certain embodiments of the present invention in which the sensitizing gases and/or liquids or a mixture thereof, inert gas, air, vacuum, and/or a supercritical fluid can be present at any of the method steps disclosed herein, including blending, mixing, consolidating, quenching, irradiating, annealing, mechanically deforming, doping, homogenizing, heating, melting, and packaging of the finished product, such as a medical implant.

The term "free radical initiator" refers to what is known in the art as substances which can yield radical species under certain conditions, for example, by heating. They generally possess bonds that can easily dissociate. For example, peroxide(s) contain easily breakable 0-0 bonds.

The term "nucleating agent" refers to an additive known in the art, an organic or inorganic material with a molecular weight less than that of the base polymer, which increases the rate of crystallization in the polymeric material. Typically, organocarboxylic acid salts, for example calcium carbonate, are good nucleation agents for polyolefins. Also, nucleating agents are typically used in small concentrations such as 0.5 wt %.

The term "crystallinity" refers to the fraction of the polymer that is crystalline. The crystallinity is calculated by knowing the weight of the sample (weight in grams), the heat absorbed by the sample in melting (E, in J/g) and the heat of melting of polyethylene crystals ($\Delta H=291$ J/g), and using the following equation according to ASTM F2625 and the like or their successors:

% Crystallinity=$E/w \cdot \Delta H$

The term "peak melting temperature' refers to what is known in the art as the melting transition of a polymeric material, where the material goes to a transition from a solid to a melt state. In a semi-crystalline material such as UHMWPE, this transition can overlap with the melting temperature of its crystalline portion. It can be determined using a differential scanning calorimeter at a heating rate of 10° C./min from −20° C. to 200° C. The peak melting temperature for UHMWPE is generally about 136 to about 140° C., or can be about 144 to about 147° C. if it contains extended chain crystals.

The term "non-permanent device" refers to what is known in the art as a device that is intended for implantation in the body for a period of time shorter than several months. Some non-permanent devices could be in the body for a few seconds to several minutes, while other may be implanted for days, weeks, or up to several months. Non-permanent devices include catheters, tubing, intravenous tubing, and sutures, for example.

The term "packaging" refers to the container or containers in which a medical device is packaged and/or shipped. Packaging can include several levels of materials, including bags, blister packs, heat-shrink packaging, boxes, ampoules, bottles, tubes, trays, or the like or a combination thereof. A single component may be shipped in several individual types of package, for example, the component can be placed in a bag, which in turn is placed in a tray, which in turn is placed in a box. The whole assembly can be sterilized and shipped. The packaging materials include, but not limited to, vegetable parchments, multi-layer polyethylene, Nylon 6, polyethylene terephthalate (PET), and polyvinyl chloride-vinyl acetate copolymer films, polypropylene, polystyrene, and ethylene-vinyl acetate (EVA) copolymers.

The term 'medical implant' refers to a medical device made for the purpose of implantation in a living body, for example and animal or human body. The medical implants include but are not limited to acetabular liners, tibial insert, glenoid component, patellar components, and other load-bearing, articular components used in total joint surgery. The term "permanent device" refers to what is known in the art that is intended for implantation in the body for a period longer than several months. Permanent devices include medical implants or devices, for example, acetabular liner, shoulder glenoid, patellar component, finger joint component, ankle joint component, elbow joint component, wrist joint component, toe joint component, bipolar hip replacements, tibial knee insert, tibial knee inserts with reinforcing metallic and polyethylene posts, intervertebral discs, sutures, tendons, heart valves, stents, and vascular grafts. The term "medical implant" refers to what is known in the art as a device intended for implantation in animals or humans for short or long term use. The medical implants, according to an aspect of the invention, comprises medical devices including acetabular liner, shoulder glenoid, patellar component, finger joint component, ankle joint component, elbow joint component, wrist joint component, toe joint component, bipolar hip replacements, tibial knee insert, tibial knee inserts with reinforcing metallic and polyethylene posts, intervertebral discs, sutures, tendons, heart valves, stents, and vascular grafts.

What is meant by room temperature is between 15° C. and 30° C.

What is meant by "virgin" is a material with no additives. For instance virgin polymeric material is a polymeric material with no additives such as antioxidants or cross-linking agents.

The term "interface" in this invention is defined as the niche in medical devices formed when an implant is in a configuration where a component is in contact with another piece (such as a metallic or a non-metallic component), which forms an interface between the polymer and the metal or another polymeric material. For example, interfaces of polymer-polymer or polymer-metal are in medical prosthesis, such as orthopedic joints and bone replacement parts, for example, hip, knee, elbow or ankle replacements.

Medical implants containing factory-assembled pieces that are in close contact with the polyethylene form interfaces. In most cases, the interfaces are not readily accessible to ethylene oxide gas or the gas plasma during a gas sterilization process."

Polymeric materials" or "polymer" include polyethylene, for example, Ultra-high molecular weight polyethylene (UHMWPE) refers to linear non-branched chains of ethylene having molecular weights in excess of about 500,000, preferably above about 1,000,000, and more preferably above about 2,000,000. Often the molecular weights can reach about 8,000,000 or more. By initial average molecular weight is meant the average molecular weight of the UHMWPE starting material, prior to any irradiation. See U.S. Pat. No. 5,879,400, PCT/US99/16070, filed on Jul. 16, 1999, and PCT/US97/02220, filed Feb. 11, 1997. The term "polyethylene article" or "polymeric article" or "polymer" generally refers to articles comprising any "polymeric material" disclosed herein.

The term "polymeric materials" or "polymer" also include hydrogels, such as poly (vinyl alcohol), poly (acrylamide), poly (acrylic acid), poly(ethylene glycol), blends thereof, or interpenetrating networks thereof, which can absorb water such that water constitutes at least 1 to 10,000% of their original weight, typically 100 wt % of their original weight or 99% or less of their weight after equilibration in water.

"Polymeric material" or "polymer" can be in the form of resin, flakes, powder, consolidated stock, implant, and can contain additives such as antioxidant(s). The "polymeric material" or "polymer" also can be a blend of one or more of different resin, flakes or powder containing different concentrations of an additive such as an antioxidant. The blending of resin, flakes or powder can be achieved by the blending techniques known in the art. The "polymeric material" also can be a consolidated stock of these blends.

"Polymeric materials" or "polymers" can also include structural subunits different from each other. Such polymers can be di- or tri- or multiple unit-copolymers, alternating copolymers, star copolymers, brush polymers, grafted copolymers or interpenetrating polymers. They can be essentially solvent-free during processing and use such as thermoplastics or can include a large amount of solvent such as hydrogels. Polymeric materials also include synthetic polymers, natural polymers, blends and mixtures thereof. Polymeric materials also include degradable and non-degradable polymers.

The products and processes of this invention also apply to various types of polymeric materials, for example, any polypropylene, any polyamide, any polyether ketone, or any polyolefin, including high-density-polyethylene, low-density-polyethylene, linear-low-density-polyethylene, ultra-high molecular weight polyethylene (UHMWPE), copolymers or mixtures thereof. The products and processes of this invention also apply to various types of hydrogels, for example, poly(vinyl alcohol), poly(ethylene glycol), poly (ethylene oxide), poly(acrylic acid), poly(methacrylic acid), poly(acrylamide), copolymers or mixtures thereof, or copolymers or mixtures of these with any polyolefin. Polymeric materials, as used herein, also applies to polyethylene of various forms, for example, resin, powder, flakes, particles, powder, or a mixture thereof, or a consolidated form derived from any of the above. Polymeric materials, as used herein, also applies to hydrogels of various forms, for example, film, extrudate, flakes, particles, powder, or a mixture thereof, or a consolidated form derived from any of the above.

The term "sterile" refers to a condition of an object, for example, an interface or a hybrid material or a medical implant containing interface(s), wherein the interface is sufficiently sterile to be medically acceptable, i.e., will not cause an infection or require revision surgery. The object, for example a medical implant, can be sterilized using ionizing radiation or gas sterilization techniques. Gamma sterilization is well known in the art. Electron beam sterilization is also used. Ethylene oxide gas sterilization and gas plasma sterilization are also used. Autoclaving is another method of sterilizing medical implants. Exposure to solvents or supercritical fluids for sufficient to kill infection-causing microorganisms and/or their spores can be a method of sterilizing.

The terms "about" or "approximately" in the context of numerical values and ranges refers to values or ranges that approximate or are close to the recited values or ranges such that the invention can perform as intended, such as utilizing a method parameter (e.g., time, dose, dose rate/level, and temperature), having a desired degree of cross-linking and/or a desired lack of or quenching of free radicals, as is apparent to the skilled person from the teachings contained herein. This is due, at least in part, to the varying properties of polymer compositions. Thus, these terms encompass values beyond those resulting from systematic error. These terms make explicit what is implicit, as known to the person skilled in the art.

All ranges set forth herein in the summary and description of the invention include all numbers or values thereabout or therebetween of the numbers of the range. The ranges of the invention expressly denominate and set forth all integers, decimals and fractional values in the range. For example, the radiation dose can be about 50 kGy, about 65 kGy, about 75 kGy, about 100 kGy, about 200 kGy, about 300 kGy, about 400 kGy, about 500 kGy, about 600 kGy, about 700 kGy, about 800 kGy, about 900 kGy, or about 1000 kGy, or above 1000 kGy, or any integer, decimal or fractional value thereabout or therebetween.

The term 'heating' refers to bringing a material to a temperature, generally a temperature above that of its current state. It can also refer to maintaining said temperature for a period of time, that is, in some instances it can be used interchangeably with 'annealing'. Heating can be done at any rate. The heating rate can be from 0.001° C./min to 1000° C./min, or it can be between 0.1° C./min to 100° C./min, or it can be from 0.5° C./min to 10° C./min, or it can be any rate from 1° C./min to 50° C./min in 1° C. intervals. The heating can be done for any duration. Heating time can be from 0.1 minutes to 100 years, or from 1 minute to 24 hours, or from 1 minute to 12 hours, or 30 minutes to 10 hours, or 5 hours, or 6 hours, or 8 hours.

The term 'cooling' refers to bringing a material to a temperature, generally a temperature below that of its current state. It can also refer to maintaining said temperature for a period of time, that is, in some instances it can be used interchangeably with 'annealing'. Cooling can be done at any rate. The cooling rate can be from 0.001° C./min to 1000° C./min, or it can be between 0.1° C./min to 100° C./min, or it can be from 0.5° C./min to 10° C./min, or it can be any rate from 1° C./min to 50° C./min in 1° C. intervals, or 2.5° C./min. The cooling can be done for any duration. Cooling time can be from 0.1 minutes to 100 years, or from 1 minute to 24 hours, or from 1 minute to 12 hours, or 30 minutes to 10 hours, or 1 hours, or 2 hours, or 5 hours, or 6 hours, or 8 hours.

The term 'annealing' refers to bringing a material to a temperature and maintaining at that temperature. In the art, it can refer generally to heating a material below its melting point and maintaining at that temperature for a period of time. In this application, it refers to heating or cooling to any temperature below or above the melting temperature of a material, for example a polymeric material. Heating/cooling can be done at any rate. The heating/cooling rate can be from 0.001° C./min to 1000° C./min, or it can be between 0.1° C./min to 100° C./min, or it can be from 0.5° C./min to 10° C./min, or it can be any rate from 1° C./min to 50° C./min in 1° C. intervals. The annealing can be done for any duration. Annealing time can be from 0.1 minutes to 100 years, or from 1 minute to 24 hours, or from 1 minute to 12 hours, or 30 minutes to 10 hours, or 5 hours, or 6 hours, or 8 hours.

The term 'high temperature melting' refers to heating a material to temperatures preferably above 200° C. It can also refer to maintaining said temperature for a period of time, that is, in some instances it can be used interchangeably with 'annealing'. Heating can be done at any rate. The heating rate can be from 0.001° C./min to 1000° C./min, or it can be between 0.1° C./min to 100° C./min, or it can be from 0.5° C./min to 10° C./min, or it can be any rate from 1° C./min to 50° C./min in 1° C. intervals. The heating can be done for any duration. Heating time can be from 0.1 minutes to 100 years, or from 1 minute to 24 hours, or from 1 minute to 12 hours, or 30 minutes to 10 hours, or 5 hours, or 6 hours, or 8 hours. During heating the material is kept at a certain temperature. There may be fluctuations in temperature during heating. The fluctuations may be as little as less than 1° or as large as several tens of degrees or more.

The term 'irradiation' refers to what is known in the art as exposing a material to radiation, for example ionizing radiation such as a gamma, electron, X-ray or ultraviolet (UV) radiation. 'Radiation cross-linking' refers to a radiation process intended to cross-link a material as a result of irradiation, for example exposing UHMWPE to gamma irradiation to cross-link the material. It also refers to the cross-linking in the material that has resulted from a radiation process. The radiation dose used can be from 0.0001 kGy to 100000 kGy, or 0.1 kGy to 1000 kGy, or from 1 kGy to 300 kGy, or about 100 kGy, or about 150 kGy, or about 175 kGy, or about 200 kGy. The radiation dose rate can be from 0.001 kGy/min to 100000 kGy/min, or from 0.1 kGy/min to 100 kGy/min, or from 1 kGy/min to 50 kGy/min, or about 25 kGy/min, or about 10 kGy/min, or about 100 kGy/min. Irradiation can be done in air, in vacuum, or partial gas environments, for example mixtures of oxygen and nitrogen. It can also be done in inert gas or partial inert gas. It can also be done at ambient temperature, or below or above ambient temperature. It can be done at elevated temperatures above ambient temperature. Irradiation temperature can be from −100° C. to 1000° C., or from 0° C. to 500° C., or from 20° C. to 200° C., or from 25° C. to 150° C., or at about 25° C., or about 70° C., or about 100° C., or about 120° C., or about 125° C.

In any of the embodiments, cross-linking agent (peroxide) cross-linking, high temperature melting and their associated processes can be performed as in U.S. Patent Application No. 61/620,202, filed Apr. 4, 2012, and U.S. Provisional Patent Application No. 61/756,595, filed Jan. 25, 2013, and U.S. Provisional Patent Application No. 61/794,284, filed Mar. 15, 2013, which are incorporated in their entirety as reference.

In any of the embodiments, the preparation of the polymeric material, high temperature melting and its associated processes can be performed as in U.S. Patent Publication No. 61/154,134, which is incorporated in its entirety as reference.

In any of the embodiments, the preparation of the polymeric material, radiation cross-linking and its associated processes can be performed as in U.S. Pat. Nos. 5,879,400 and 6,786,933, which are incorporated in their entirety as reference.

In any of the embodiments, the preparation of the polymeric material, antioxidant addition to the polymeric material or radiation crosslinking can be performed as in U.S. Pat. No. 7,431,874, which is incorporated in its entirety as reference.

In any of the embodiments, the preparation of the polymeric material, antioxidant addition to the polymeric material, radiation crosslinking, or the consolidation and post-consolidation processing can be performed as in U.S. Pat. Nos. 8,426,486 and 8,425,815, which are incorporated in their entirety as reference.

Blending of Resin

In some embodiments, one or more additives are added to the polymeric material by mixing with the polymeric resin. These additives can be added sequentially or at the same time. They can also be added with the aid of a mixing agent such as a solvent. For example, an antioxidant (AO) or a mixture of AOs (e.g. vitamin E) can be blended into UHMWPE polymeric powder using isopropyl alcohol (IPA) to aid in mixing. AO is dissolved in IPA, then mixed with UHMWPE resin powder. For example the mixing is carried out in an industrial blender, whereby the UHMWPE is placed in the blender and while the blender is in action, tumbling the UHMWPE powder, the antioxidant or the antioxidant solution (for example in IPA) is injected either all at once or intermittently to achieve the desired antioxidant concentration in the final blend. Vacuum and/or heating can be used to aid in the evaporation of the solvent during or after mixing. An organic peroxide or a mixture of organic peroxides can be introduced in pure form or with the aid of a mixing agent such as a solvent together with an antioxidant or a mixture of AOs (e.g. Vitamin E) or separately. For example, a vitamin E-blended UHMWPE powder can further be mixed with peroxide 130 in pure form by injecting through the same port or in other port in the industrial blender. Alternatively, both vitamin E and P130 can be dissolved in IPA before mixing with UHMWPE resin powder. The blending of UHMWPE with the peroxide(s) or AO(s) can be carried out by adding these respective additives in any order or altogether.

Blending of any additives into the polymeric material can be done under vacuum, partial vacuum, atmospheric pressure or in a pressurized environment. The blending can be in contact with inert gas, reactive gas, oxygen, or any combination thereof. Blending can also be performed in fluids such as supercritical fluids. These environments can be continuous, sequential or alternating in any desired sequence. Blending can also be done under heating or cooling, spontaneously or externally. The temperature during the blending of additives with polymeric material can be from −100° C. to 500° C., more preferably 25° C. to 120° C., more preferably 25° C. to 90° C., most preferably about 25° C. to 80° C. Active cooling or heating can be applied during blending to maintain temperature in the desired range or ranges. The temperature during blending can also be varied in the form of heating, cooling, or soaking at a temperature as desired.

In some embodiments blending of additives with polymeric resin can be done to achieve a final desired blend concentration. Alternatively master batches or concentrated forms of additive-mixed polymeric resin blends can be used. For example, if a 0.2 wt % vitamin E blend of UHMWPE is desired, this blend can be directly mixed to 0.2 wt % vitamin E concentration; alternatively a more concentrated vitamin E/UHMWPE blend can be made (such as a 2 wt % vitamin E/UHMWPE master batch) to be later diluted down by adding virgin UHMWPE or vitamin E/UHMWPE blend with lower vitamin E concentration blend to achieve the final desired blend concentration.

For example a 2 wt % vitamin E/UHMWPE blend can be mixed with virgin UHMWPE with no additives to obtain a lower vitamin E concentrated blend. The same can be done by adding a lower vitamin E concentration blend to the 2 wt % vitamin E/UHMWPE master batch instead of the virgin UHMWPE. The addition of peroxide(s) can be done during the said dilution step. The master batch and/or the virgin/lower concentration blends could be mixed (separately or together) with organic peroxide(s).

Cross-linking agent definition also includes carbon-carbon initiators, which can also initiate cross-linking in polymeric material similar to peroxides. Some examples of this group of compounds are 2,3-dimethyl-2,3-diphenylbutane or poly-1,4-diisopropylbenzene. Cross-linking agent may be a peroxide or a carbon-carbon initiator or a mixture thereof.

The polymeric material can be blended with additives in any quantity desired, for example 20 kilograms or more of polymeric material resin can be blended with additives using industrial blenders. After blending, the blended-polymeric material can be stored under vacuum, partial vacuum, atmospheric pressure or a pressurized environment. Inert gas, air, oxygen, reactive gas, or a combination thereof can be used as storage environment. The polymeric material can be stored at a temperature from −100° C. to 500° C., preferably from −20° C. to 30° C., most preferably from −20° C. to 4° C. Storing the blended polymeric material at temperatures below room temperature in closed or sealed containers can minimize the loss of any additives to evaporation.

High Temperature Melting Process

The term 'high temperature melting' refers to heating a material to temperatures preferably above 200° C. It can also refer to maintaining said temperature for a period of time, that is, in some instances it can be used interchangeably with 'annealing'. Heating can be done at any rate. The heating rate can be from 0.001° C./min to 1000° C./min, or it can be between 0.1° C./min to 100° C./min, or it can be from 0.5° C./min to 10° C./min, or it can be any rate from 1° C./min to 50° C./min in 1° C. intervals. The heating can be done for any duration. Heating time can be from 0.1 minutes to 100 years, or from 1 minute to 24 hours, or from 1 minute to 12 hours, or 30 minutes to 10 hours, or 5 hours, or 6 hours, or 8 hours. During heating the material is kept at a certain temperature. There may be fluctuations in temperature during heating. The fluctuations may be as little as less than 1 or as large as several tens of degrees or more.

Heating can be done using a single heating, a single soaking and a single cooling cycle or it can be done with multiple heating, soaking and cooling cycles. For example, heating can be done to about 250° C., followed by soaking at about 250° C. for some duration, followed by heating to about 300° C., followed by soaking at about 300° C. for some duration, followed by cooling to about 140° C. followed by soaking at about 140° C. for some duration, followed by cooling to about room temperature.

Heating, soaking or cooling steps can be performed for 1 second to several days, more preferably from 30 minutes to several hours. For example, heating can be done to about 250° C. for about 30 minutes, followed by soaking at about 250° C. for about 30 minutes, followed by heating to about 300° C. for about 30 minutes, followed by soaking at about 300° C. for about 20 hours or longer, followed by cooling to about 140° C. for about 6 hours, followed by soaking at about 140° C. for about 3 hours, followed by cooling to about room temperature for about 3 hours.

In a preferred embodiment, the polymeric material blended with additive(s) is consolidated, then the consolidated polymeric material is heated in multiple steps to above 200° C., for example heated to 250° C. and soaked at this temperature for at least 4 hours, followed by heating to 300° C. for at least 10 hours but less than 30 hours, followed by cooling to 280° C. and soaking at this temperature for at least an hour, or about 4 hours, or about 7 hours, followed by cooling to room temperature in multiple cooling and soaking steps or one cooling step. The rate at which cooling or heating is done for each step can be different and it can be from 0.0001° C./min to 100° C./min or more, or from 0.1° C./min to about 1° C./min, or about 0.3° C./min, or about 2.5° C./min.

High temperature melting alters the mechanical properties and the wear rate of the polymeric resin. In preferred embodiments the polymeric resin is previously blended with an antioxidant (for example vitamin E, Irganox 1010, or a HALS, or a mixture thereof) and a cross-linking agent (for example a carbon-carbon initiator, Trigonox 311, or P130, or a mixture thereof). During high temperature melting the Izod strength of the material increases while the wear rate of the material decreases as a function of increasing temperature and increasing duration of high temperature melting. In some cases, there are byproducts present from the previous cross-linking and/or generated during high temperature melting. High temperature melting also assists in removal of these byproducts, most of which are volatile. Depending of the formulation of the polymeric resin, that is the additives used, optimization of the high temperature melting parameters would be necessary to avoid too much compromise on the wear rate but at the same time to remove any unwanted byproducts. Not all byproducts are unwanted. In some cases the byproducts are biocompatible, therefore their removal may not be necessary.

After High Temperature Melting

High temperature melting can be done on any size sample of interest. For example, a cylindrical bar with a diameter of approximately less than 1", 1.5", 2", 3", or 4" or larger may be produced by ram extrusion. This bar can be high temperature melted as is or may be machined into smaller samples, implant preforms or implants before or after high temperature melting. Multiple machining steps can be employed in between steps also.

Implant preforms are shapes that are dimensionally larger than implants. After completion of any required processing, the implant preforms are machined by removing anywhere between 100 μm to several millimeters or centimeters to obtain the final implant form.

A high temperature melted sample can be exposed to different environments before or after high temperature melting. They can be heated or cooled in water or aqueous solutions, organic solvents, gases or supercritical fluids. They can be under vacuum or partial vacuum or atmospheric conditions. They can be exposed to multiple environmental conditions sequentially for various periods of time.

Extraction of certain molecules, for instance, byproducts of peroxide cross-linking and/or byproducts of high temperature melting and/or residual unreacted peroxide molecules, from samples may be desired before or after high temperature melting. Extraction can be done at any temperature in a desired environment such as in contact with liquids, gases or supercritical fluids.

In an embodiment of the invention, the polymeric resin with one or more additives is consolidated. The consolidated polymeric material is high temperature melted. The high temperature melted polymeric material is machined. High temperature melted, machined polymeric material is placed in an extraction environment for a period of time. The high temperature melted, machined, extracted polymeric material is further machined into implant form. The implant is packaged and sterilized.

In an embodiment of the invention, the polymeric resin with one or more additives is consolidated. The consolidated polymeric material is machined. The machined polymeric material is high temperature melted. Machined, high temperature melted polymeric material is placed in an extraction environment for a period of time. The high temperature melted, machined, extracted polymeric material is further machined into implant form. The implant is packaged and sterilized.

In other embodiments the extraction step is carried out from the consolidated polymeric material.

"Extraction" defines what is known in the art as removal of some components from polymeric material. Removal can be aided in contact with a solvent, fluid, an emulsion, a slurry, gas or supercritical fluid. Mixtures or stepwise use of different environments can be employed. Extraction can be performed at a temperature from −100° C. to 500° C. or more, more preferably it is performed between room temperature or about 25° C. to about 300° C., more preferably about 40, 50, 60, 70, 80, 90, 100, 110, 120, 130, 135, 137, 140, 160, 250, or 300° C. Extraction duration can be 1 minute to several months, more preferably about 24 hours, most preferably about 4 hours. It can be done in partial vacuum, vacuum, ambient conditions or under pressure applied by a liquid, by mechanical means or contained by self-pressurization.

Extraction of unreacted species and/or chemical byproducts is desirable in some implants because they can cause adverse local tissue reactions not well tolerated by the patient. Extraction can be a thermal treatment where the polymeric material (for example peroxide cross-linked antioxidant containing UHMWPE before or after high temperature melting) is subjected to a series of heating to a temperature, soaking at that temperature, and cooling to a temperature. Steps of heat, soak, cool can be used in any order, in any sequence, and/or in as many times as desired or needed. Multiple heat/soak/heat/soak/cool/soak cycles can be used.

High temperature melting of larger size polymeric material is more challenging due to the poor thermal conductivity of the polymeric material. Therefore, the high temperature melting is tailored to ensure that heating and cooling cycles are done in a way to minimize the temperature gradient generated within the polymeric material. However, once one optimizes this process there will always be some thermal gradient, for instance, during heating the surface temperature will stay higher than core temperature and vice versa during cooling. For instance, in one trial we optimized the high temperature melting of a polymeric material of about 4" in diameter and about 10" in length in a nitrogen convection oven by heating the sample first to an elevated temperature close to but below the high temperature melting temperature slowly to obtain uniformity in the sample before heating further to the high temperature melting temperature. In this manner, the temperature non-uniformity during HTM was minimized for a large block sample and the effects of the HTM, which can be dependent on duration were also more uniform. This polymeric material was obtained by ram extruding an approximately 4" diameter bar using GUR 1050 UHMWPE resin powder containing 0.2 wt % Vitamin E and 0.8 wt % P130.

Following high temperature melting, the cooling cycle can also be tailored to minimize the temperature gradient within the polymeric material. The cooling cycle can have cooling to the desired temperatures as well as soaking at desired temperatures. For example the high temperature melting can be carried out, for example at 300° C. for a desired amount of time, for example 30 hours. Subsequently the polymeric material can be cooled down for example to 250° C., for example over a period of a few hours, and soaked at that temperature for a few hours until the temperature within the polymeric material is approximately 250° C. throughout. Subsequently the polymeric material can be cooled down to for example 140° C., for example over a period of a few hours, and soaked at that temperature for a few hours until the temperature within the polymeric material is approximately 140° C. throughout. Subsequently the polymeric material can be cooled down to 100° C., for example over a period of a few hours or longer, and soaked at that temperature for a few hours until the temperature within the polymeric material is approximately 100° C. throughout. With UHMWPE the crystallization will take place between 140° C. and 100° C. during cool-down; therefore more time may be required to soak the high temperature melted, peroxide cross-linked UHMWPE/vitamin E blend at 100° C. to ensure that the entire polymeric material is crystallized and cooled down to approximately 100° C. Subsequently the polymeric material can be cooled down slowly to room temperature or alternatively additional cool/soak steps can be used.

Consolidation

In one embodiment, a polymeric material is blended with one or more additives, where one or more of these additives are cross-linking agents and one or more of these additives are antioxidants. The blend is then consolidated by ram extrusion. The consolidated blend can then be heated to below or above the melting temperature and/or high temperature melted and cooled. The consolidated and thermally treated polymeric material can be machined into implant preforms or medical implants. The medical implant can be packaged and sterilized.

Some parameters that can be varied during ram extrusion are the ram speed, the feed rate, the barrel diameter, the barrel length, and the barrel temperature. The barrel temperature is typically controlled by multiple heating zones; therefore, one has the flexibility to vary the temperature at some fashion along the length of the ram extrusion barrel. These parameters can be changed to manipulate the properties of the resulting consolidated bar of polymeric material such as mechanical strength, crosslink density, wear rate or toughness among others.

In one embodiment, a polymeric material is blended with one or more additives, where one or more of these additives are cross-linking agents and one or more of these additives are antioxidants. The blend is then consolidated by ram extrusion. The consolidated blended polymeric material can be machined into blocks or implant preforms. The machined blocks or implant preforms can then be heated to below or above the melting temperature and/or high temperature melted and cooled. The consolidated and thermally treated polymeric material can be machined further into medical implants. The medical implant can be packaged and sterilized.

Machining and thermal treatment steps can be repeated as many times as necessary until the final implant is packaged and sterilized. One concern with heat treatment is dimensional stability; if there are a lot of dimensional changes during thermal treatment, then the thermal treatment can be performed on a large consolidated polymeric material such as a bar, a block, or an implant preform. If the dimensional change is less than the machining tolerances for the final implants, then thermal treatment can be performed on a final implant form as well before packaging and sterilization.

Thermal treatment or extraction can be used to remove volatiles from a polymeric material at any stage of processing. For this reason, thermal treatment can be performed with multiple soaking, ramping, heating, cooling steps and utilizing different environments such as inert gas, air or a combination thereof. The thermal treatment can also be performed in other gases, liquids, supercritical fluids or a combination or a sequence thereof.

The "cross-linking agent" is added to the polymeric material to form a blend and a cross-linking agent can be activated to initiate the cross-linking. Cross-linking agents are chemical additives. Some cross-linking agents can generate free radicals that abstract a hydrogen from the polymeric material to form free radicals on the polymeric material. The free radicals on the polymeric material react with each other to form cross-links. The activation of this type of cross-linking agent, in some embodiments, requires heat. The free radical generation may require decomposition of the cross-linking agent. Therefore the initiation of cross-linking of the polymeric material by such a cross-linking agent would need an activation and/or decomposition of the cross-linking agent. The terms "activation" and "decomposition" are used interchangeably to indicate the generation of free radicals to initiate cross-linking of the polymeric material.

Consolidation and cross-linking steps can be performed simultaneously and/or sequentially and can be repeated as many times as needed. Consolidation can have multiple steps of heat, soak, cool repeated in any order or sequence and as many times as needed to achieve acceptable levels of consolidation and crosslinking. In some embodiments the crosslinking agent is thermally activated to initiate the crosslinking process. In these cases if the activation temperature is below or around the temperatures used during consolidation some or all of the crosslinking will take place during consolidation. If the activation temperature is above the consolidation temperature then there will be little or no crosslinking taking place during consolidation. In those cases where little, some, or no crosslinking have occurred during consolidation, the consolidated polymeric material can be heated further to a temperature within a range of temperatures to increase the crosslink density of the polymeric material. For example, if a polymeric material is blended with an organic peroxide whose 1-hour decomposition temperature is 180° C., consolidation for 10-20 minutes at 180° C. will not have substantially decomposed the peroxide and not have led to substantial cross-linking of the polymeric material. In order to increase the cross-link density further, the consolidated, peroxide-blended polymeric material can be heated further to another temperature close to or above 180° C. for one hour or more. This final heating step can be combined with high temperature melting.

Multiple consolidation temperatures can be used during the consolidation cycle. These temperatures, which are often dictated by the temperature of the mold, in which the consolidation is taking place, can be changed in a continuous or step-wise manner. For example, a polymeric material blended with additive(s) can be consolidated starting at around 160° C. for a period of time, then consolidated further at around 190° C. for another period of time. Alternatively, consolidation can start at a temperature of around 140° C. for a period of time, which can be ramped to around 230° C. for a period of time and held there for a period of time over the consolidation period. These temperatures and durations can be changed to increase or decrease the usage of the additive(s) in the polymeric material. For example usage of the additive(s) could be the decomposition of the peroxide additive during consolidation, or the reaction of the antioxidant with the free radicals generated during consolidation, or the reaction of the carbon-carbon initiator additive during consolidation. For example, increasing the temperature may increase the decomposition of an organic peroxide or a carbon-carbon initiator added into the polymeric material and thus may change the rate of cross-linking of the polymeric material. Also, using temperatures for consolidation below the temperatures at which substantial decomposition of the cross-linking agent or peroxide can occur may improve consolidation before cross-linking of the polymeric material. In such cases, the consolidation temperature can be increased to increase the cross-link density after a period at a lower temperature.

In one embodiment, polymeric material blended with one or more additives, some of which may be antioxidant(s) and/or cross-linking agent(s), is consolidated. The consolidated polymeric material is irradiated. The consolidated, irradiated polymeric material is heated to below or above the melting temperature and/or high temperature melted. Then, the irradiated, thermally treated polymeric material is consolidated. The consolidated, irradiated, thermally treated and consolidated polymeric material can be irradiated again. Then, it can be further thermally treated. Finally, the polymeric material can be machined into implants. The implants are packaged and sterilized.

In another embodiment, polymeric material blended with one or more additives, some of which may be antioxidant(s) and/or cross-linking agent(s), is consolidated. The consolidated polymeric material is heated to below or above the melting temperature and/or high temperature melted. Then, the consolidated, thermally treated polymeric material can be irradiated. Finally, the polymeric material can be machined into implants. The implants are packaged and sterilized.

In another embodiment, polymeric material blended with one or more additives some of which may be antioxidant(s) and/or cross-linking agent(s) is consolidated. The consolidated polymeric material is heated to below or above the melting temperature and/or high temperature melted. Then, the consolidated, thermally treated polymeric material can be machined into implants. The implants are packaged and irradiated.

In some embodiments the consolidation is carried out by what is known in the art as ram compression. What is meant by "ram compression" is the consolidation of polymeric material placed inside a mold where a ram applies the pressure and also where the mold is heated. Typically a ram extrusion set up can be used for this purpose. Instead of a continuous mold with an open end (use with ram extrusion), a mold with a closed end is used. Polymeric material is put inside the mold. Pressure is applied by the ram. The mold is heated. The pressurization and heating can happen in any order. When the consolidation reaches the desired level, the pressure is released and the mold is cooled down. The order in which the pressure is released and the temperature is decreased can vary. The mold can have bleeding valves to remove volatiles that might be formed during consolidation.

Layered Molding Embodiments

In some embodiments, a polymeric material with additive(s) such as cross-linking agent(s) can be consolidated comprising different layers. The layers can include different types of polymeric material or mixtures thereof and/or different concentration of any of the additive(s) incorporated into the polymeric material.

In some embodiments, the consolidation of polymeric material comprising layers can be done such that the resulting consolidated polymeric material is close to the final shape to be used in the final application/product, for example a medical implant. Some minor machining can optionally be performed to result in a final product/implant. In some embodiments the machining is done on all surfaces. In other embodiments the machining is done on selective surfaces: for example only the articular surfaces of a medical implant are machined or only the backside surfaces are machined, and/or one of the articular/backside surfaces is machined together with the peripheral surfaces.

In some embodiments, a polymeric material with additive(s) with no cross-linking agents can be layered into a consolidation mold/chamber together with a second layer comprising a polymeric material with additive(s) at least one of which is a cross-linking agent. In some embodiments the latter layer is placed as the top layer inside the mold or as the bottom layer inside the mold. The two layers are either partially or totally consolidated together or separately by placing in partially or totally in contact with heated surfaces. Partial consolidation can be also done in contact with non-heated surfaces.

In some embodiments, layering can be done in multiple steps of consolidation. Layers can have the same composition or different compositions. Layering can be done with two layers or more layers. Layering can also be used on parts of a surface, for example some areas of the surfaces of the intended final product.

In one preferred embodiment, polymeric material also comprising an antioxidant, for example vitamin E, is placed inside a mold. Subsequently the said polymeric material with an antioxidant is subjected to compression inside the mold to achieve partial consolidation. The said partial consolidation is performed at below room temperature, at room temperature, at above room temperature, or at above the melting point of the said polymeric material. Preferably the said consolidation is performed between room temperature and the melting point of the said polymeric material. Preferably the said consolidation is performed without applying any active heating or cooling to the mold. After the partial consolidation of the said polymeric material, and other polymeric material with an antioxidant and a cross-linking agent is placed on top of the partially consolidated first layer of polymeric material. Subsequently the two layers are consolidated under compression inside the mold. The said consolidation is performed either at a single temperature for a prescribed duration or at different temperatures in different periods of time using a multiple heating, soaking, and cooling cycles in a desired order.

In one preferred embodiment, polymeric material also comprising an antioxidant, for example vitamin E, is placed inside a mold. Subsequently the said polymeric material with an antioxidant is subjected to compression inside the mold to achieve partial consolidation. The said partial consolidation is performed at below room temperature, at room temperature, at above room temperature, or at above the melting point of the said polymeric material. Preferably the said consolidation is performed between room temperature and the melting point of the said polymeric material. Preferably the said consolidation is performed without applying any active heating or cooling to the mold. After the partial consolidation of the said polymeric material, an intermediate heating step(s) can be used such as high temperature melting of the partially consolidated polymeric material. After partial consolidation and heating/cooling, other polymeric material with an antioxidant and a cross-linking agent is placed on top of the partially consolidated first layer of polymeric material. Subsequently the two layers are consolidated under compression inside the mold. The said consolidation is performed either at a single temperature for a prescribed duration or at different temperatures in different periods of time using a multiple heating, soaking, and cooling cycles in a desired order. Such a consolidated polymeric material can be subsequently heated/cooled or machined on one or more surfaces.

Diffusion of Cross-Linking Agents

In some embodiments, the polymeric material is blended with additive(s), at least one of which is an antioxidant. Then the antioxidant-blended polymeric material can be machined into an implant or implant preform. Cross-linking agent(s) are diffused into the implant or implant preform. The depth of diffusion can be varied depending on the diffusion parameters. Cross-linking agent can be activated such that a cross-linked implant or implant preform is obtained. At least one cross-linking agent can be a peroxide. In the case of peroxides, cross-linking can be (further) activated by heating the implant preform or implant to dose to or above the decomposition temperature(s) of the peroxide(s). In some embodiments the temperature of diffusion will be high enough to decompose the peroxide as it diffuses in to the implant or implant preform or the polymeric material, thereby cross-linking the polymeric material during diffusion. Then, the polymeric material can be machined into an implant. The implant can be packaged and sterilized. In some embodiments the diffusion will be performed using a machined implant, therefore no further machining may be necessary.

Diffusion of the cross-linking agent can be done in its pure form, in solution or in emulsion. That is, the antioxidant-blended polymeric material can be contacted with the cross-linking agent formulation in the form of gas, liquid, solid, melt, slurry, emulsion, supercritical fluid or a mixture or sequence thereof. For example, an organic peroxide can be emulsified using an emulsifier (a chemical additive which can aid in the more uniform distribution/dispersion of compound(s) in liquids where it is not dissolved well, for example Tween 20) in water or an aqueous based solution. The antioxidant-blended polymeric material can be contacted with this emulsion for a desired period of time to allow the diffusion of the cross-linking agent into the polymeric material. Diffusion can be done below room temperature, around room temperature, at an elevated temperature below or above the melting point of the polymer. The diffusion medium can contain other additives in addition to the cross-linking agent and the emulsifier. For example, the diffusion medium can contain other antioxidant(s), cross-linking agent(s) or any other desired molecule that can diffuse into the polymeric material.

Diffusion of additive(s) into the polymeric material can be done for 1 minute to several weeks, preferably from 1 hour to 24 hours, more preferably from 1 hour to 12 hours, most preferably from 1 hour to 8 hours.

Cross-linking can take place during diffusion depending on the diffusion medium, temperature and duration. Alternatively or in addition, the additive-diffused polymeric material can be heated further after the diffusion step. If the samples were heated during diffusion, then they can be cooled before this heating step. Heating can be done to a temperature between room temperature and 500° C., preferably to between room temperature and 250° C., or to 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370 or 380° C. As in other embodiments in this application, heating can be done in a gaseous environment, liquid environment, in contact with solids or in a supercritical environment or a combination or a sequence thereof. Heating can be done for 1 minute to several weeks, preferably from 1 hour to 24 hours, more preferably from 1 hour to 12 hours, most preferably from 1 hour to 8 hours. If the heating is performed with the purpose of decomposing an organic peroxide used as a cross-linking agent for the polymeric material, then the heating temperature can be close to or above the 1-hour decomposition temperature of the peroxide.

In one preferred embodiment, polymeric material also comprising an antioxidant, for example vitamin E, is placed inside a mold. Subsequently the said polymeric material with an antioxidant is subjected to compression inside the mold to achieve partial consolidation. The said partial consolidation is performed at below room temperature, at room temperature, at above room temperature, or at above the melting point of the said polymeric material. Preferably the said consolidation is performed between room temperature and the melting point of the said polymeric material. Preferably the said consolidation is performed without applying any active heating or cooling to the mold. After the partial consolidation of the said polymeric material, an intermediate heating step(s) can be used such as high temperature melting of the partially consolidated polymeric material. After partial consolidation and heating/cooling, additive(s) including antioxidant(s) and/or cross-linking agent(s) can be diffused into the polymeric material. Subsequently the partially consolidated, heated/cooled, additive-diffused polymeric material is consolidated under compression inside a mold. The said consolidation is performed either at a single temperature for a prescribed duration or at different temperatures in different periods of time using a multiple heating, soaking, and cooling cycles in a desired order. Such a consolidated polymeric material can be subsequently heated/cooled or machined on one or more surfaces.

In some embodiments the efficiency of the peroxide initiated cross-linking can be increased by the addition of co-agents, also known as cross-linking activators such as triallyl cyanurate, triallyl isocyanurate, quinone dioxime, diallyl phthalate, ethylene glycol dimethacrylate, trimethylolpropane trimethacrylate, N,N'-m-phneylenebismaleimide, 1,2-poly-butadiene and so on.

In other embodiments the extent of scorch can be reduced. By scorch is meant premature cross-linking before consolidation of polymeric material during heating and pressurizing for the cross-linking and consolidation step. It is desirable to consolidate the polymeric material before cross-linking; therefore it is desirable to reduce the extent of scorch. In some cases if cross-linking of the polymeric material occurs before consolidation reaches the desirable level, it may become more difficult for consolidation to be taken to the desirable level. The scorch can be reduced or inhibited by using anti-scorch compounds such as nitrites, 2-mercaptobenzothiazole, and/or hydroquinones. For example 2,4-diphenyl-4-methyl-1-pentene (α-methylstyrene dimer), 1,1-diphenylethylene (substituted or unsubstituted), [1,3,5-tris(4-tert-butyl-3-hydroxy-2,6-dimethylbenzyl)-1,3,5-triazine-2,4,6-(1H,3H,5H)-trione], 4,4'-thiobis(2-methyl-6-t-butylphenol), 2,2'-thiobis(6-t-butyl-4-methyphenol), or mixtures thereof can be used as scorch inhibitor(s). The scorch inhibitor can be added at any concentration into the polymeric material.

In some of the embodiments individual antioxidants or mixtures are used as anti-scorching agents. For example, a primary antioxidant is used together with other secondary antioxidants as anti-scorching agents. Commercial Irganoxes, for instance Irganox 300 (4,40-Thiobis(6-tertbutyl-3-methylphenol), Irganox 1010 (Tetra[methylene-b-(3,5-ditertbutyl-4-hydroxyphenyl)-propionate]methane), Irganox 1035 (3,5-Bis(1,1-dimethylethyl)-4-hydroxyhydroxybenzenepropanoic acid thiodi-2,1-ethanediyl ester), Irganox 1076 (n-Octadecyl-b-(4-hydroxy-3,5-ditertbutylphenyl) propionate), or other hindered phenol type antioxidants, Vitamin E, vitamin acetate, can be used as primary antioxidants. These antioxidants can be used together with secondary antioxidants such as commercial Irganoxes, Irganox 168 (Tris(2,4-ditertbutyl) phosphate), Irganox 242 (2,4-Ditertbutylphenyl phosphate) and Irganox(DLTP dilaurylthiodipropionate(didodecyl-3,3'-thiodipropinate)). The anti-scorching agents can be used together with peroxide cross-linking agents during consolidation. Subsequently, the consolidated polymeric material containing cross-linking agents and anti-scorching agents can be subjected to high temperature melting and subsequently machined into implants, packaged, and sterilized.

EXAMPLES

Example 1. The Increased Occurrence of Defects with Increasing Temperature

GUR1020 UHMWPE compression molded barstock (60 mm by 60 mm cross-section; Orthoplastics, UK) was cut in approximately 100 mm-long pieces. The pieces (n=5 each) were high temperature melted at different temperatures ranging from 305° C. to 320° C. for 6 to 12 hours (Table 2). After cooling down to room temperature, the samples were cut in half and the crossection was investigated for defects. The incidence of defects was noted.

TABLE 2

The probability of observing a defect in completely consolidated, then high temperature melted UHMWPEs. All were GUR1020 UHMWPE

| Type of UHMWPE | HTM Temperature and Time | Vinyl Index | % defect |
|---|---|---|---|
| Virgin | 305° C. - 12 hrs | 0.063 | 20 |
| Virgin | 305° C. - 8 hrs | 0.049 | 20 |
| Virgin | 310° C. - 8 hrs | 0.048 (w/o defects) 0.068 (w/defects) | 20 |
| Virgin | 310° C. - 12 hrs | 0.068 | 20 |
| 0.1 wt % vitamin E blend | 310° C. - 6 hrs | 0.021 | <20 |
| Virgin | 315° C. - 6 hrs | 0.067 | 80 |
| 0.1 wt % vitamin E blend | 320° C. - 6 hrs | 0.060 | 40 |

Thin sections (150 μm) were microtomed across the cross-section and Fourier transform infrared spectroscopy was used to obtain spectra. Several data points were taken along the depth of the sample at 4 $cm^{-1}$ and average of 32 scans was recorded. A vinyl index was calculated using the area under 880-920 $cm^{-1}$ and normalizing it to the area under 1895 $cm^{-1}$ (1850-1985 $cm^{-1}$).

Increasing the temperature and increasing the time of exposure during high temperature melting have been associated with increased vinyl index and increased elongation (Fu et al. Polymer 51: 2721-2731 (2010)).

Figure 4:
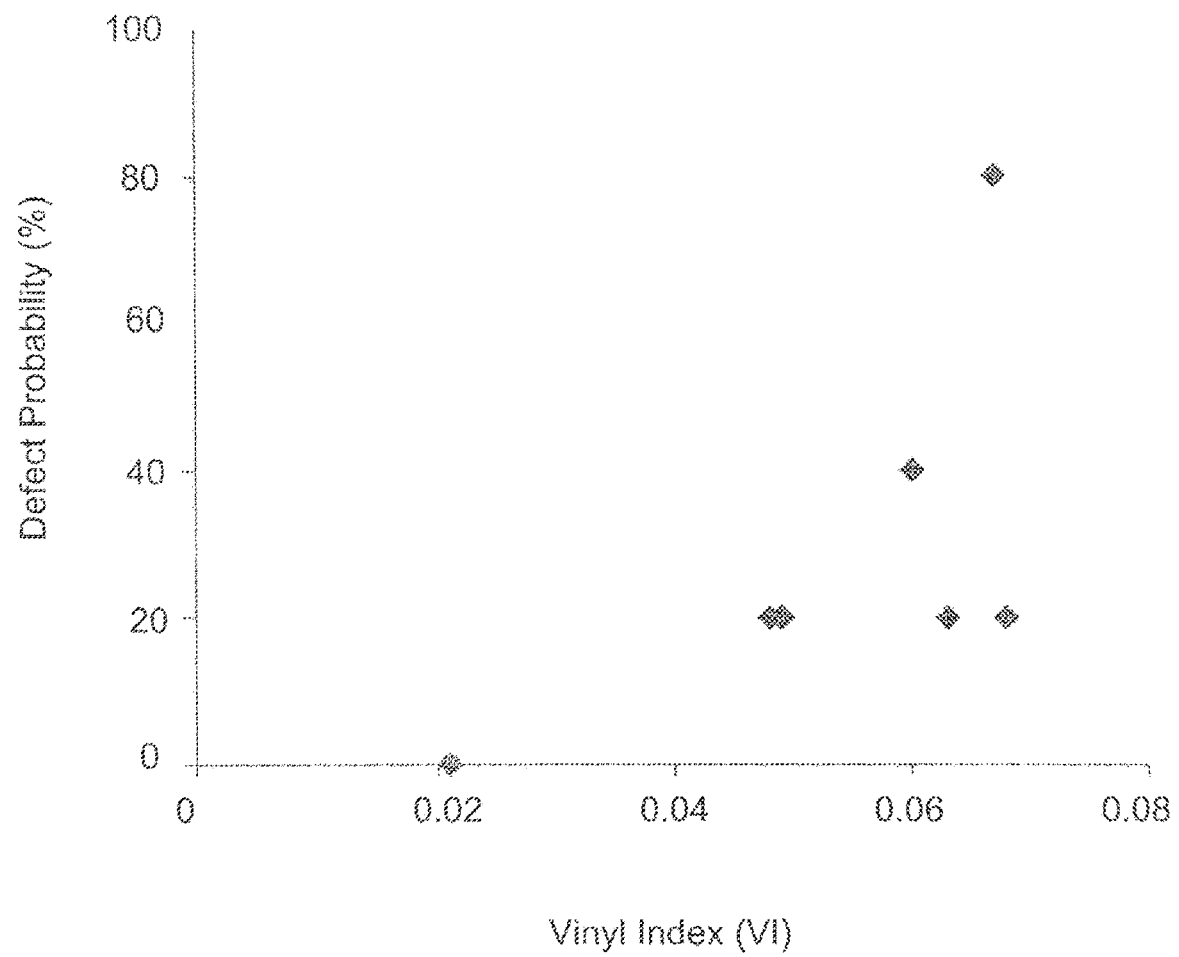
FIG. 4. Probability of observing a defect in completely consolidated, then high temperature melted UHMWPE (60 by 60 by 100 mm) with increasing vinyl index.

It was observed that the probability of observing a defect generally increased with increasing temperature (Table 1) and increasing vinyl index (FIG. 4).

Example 2. The Effect of the Pre-Molding Step on Defects

Figure 5:
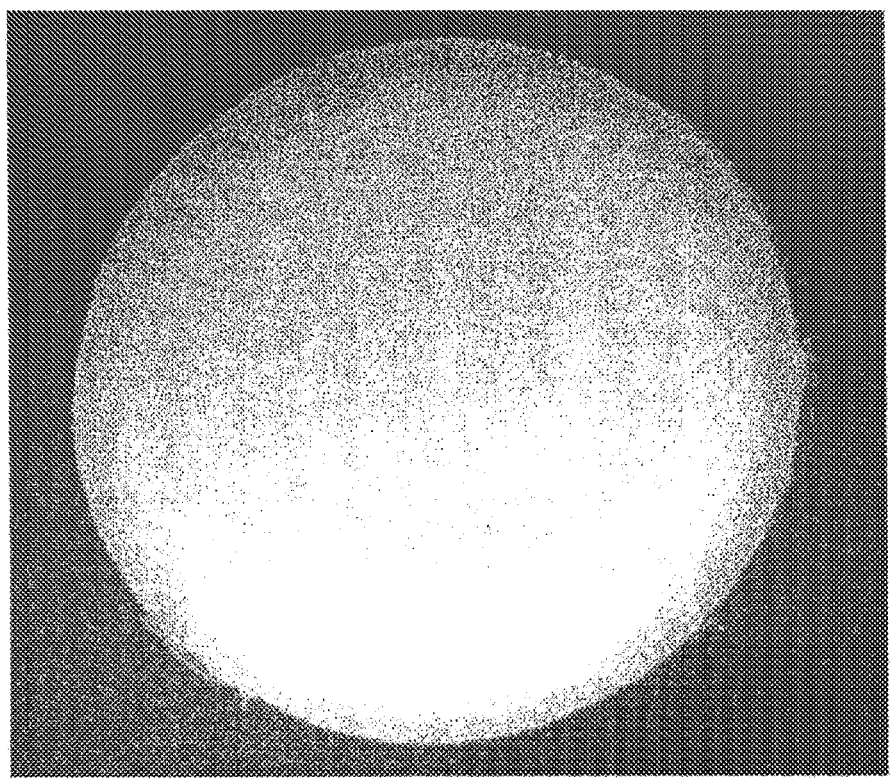
FIG. 5. Example of a UHMWPE cylindrical puck (67 mm in diameter, 43 mm in height) made by the 'pre-molding', heat treatment and complete consolidation steps without any defects.

A GUR1020 UHMWPE resin powder (~200 g) was poured into a cylindrical mold with about 67 mm diameter and compressed with 4000 lbs (~5 MPa) between platens pre-heated to 181° C., for 20 minutes, then was cooled down to about room temperature. The 'pre-molded' or 'partially consolidated' green pellet was taken out of the mold and placed in a convection oven pre-heated to 320° C. The oven was purged with nitrogen and the nitrogen flow was maintained during heating and maintaining the sample at temperature for 6 hours and cooling after this period to about room temperature. The pre-molded and high temperature melted puck was placed into the same mold used for pre-molding and compressed with 41200 lbs (~50 MPa) between platens pre-heated to 194° C., for 15 minutes, then was cooled down to about room temperature before releasing the pressure. This cylindrical puck was cut horizontally roughly in the middle (as shown in FIG. 1b) and no defects were noted (FIG. 5).

Example 3. The Mechanical Properties of Partially Consolidated, High Temperature Melted and Completely Molded UHMWPE Via the Two-Step Molding GUR1020 UHMWPE resin powder was poured into a cylindrical mold with about 100 mm diameter and compressed with 4000 lbs (~2 MPa) between platens pre-heated to 358 F (181° C.) for 10 minutes, then was cooled down to about room temperature. The partially consolidated pellet was taken out of the mold and placed in a convection oven pre-heated to temperature. The oven was purged with nitrogen and the nitrogen flow was maintained during heating and maintaining the sample at temperature for the desired amount of time and cooling after this period to about room temperature. One sample was processed at 280° C. for 6 hours, one sample was processed at 300° C. for 5 hours, one sample was processed at 310° C. for 6 hours and one sample was processed at 320° C. for 6 hours. After HTM, the cylindrical pucks were placed back into the consolidation mold and molded completely between platens pre-heated to 381 F (194° C.) for 10 minutes at ~20 MPa, then was cooled down to about room temperature under pressure.

Tensile testing was performed on dog-bones (Type V, ASTM D-638) stamped out of 3.2 mm-thick sections machined from the final pucks. Testing was performed at 10 mm/min (MTS Insight, Eden Prairie, Minn.). Elongation to break (EAB) was determined by using a laser extensometer. Ultimate tensile strength (UTS) and yield strength (YS) were also measured.

IZOD impact testing was performed on impact coupons (63.5 mm×12.7 mm×6.35 mm) after double notching according to ASTM F648.

There were no defects observed in these samples. The ultimate tensile strength and the yield strength were high and the elongation at break was exceptionally high, especially for the sample processed at 320° C. (Table 3).

TABLE 3

Tensile mechanical properties of partially consolidated, high temperature melted and completely consolidated UHMWPE via the two-step molding process.

| HTM Temperature and time | IZOD Impact Strength (kJ/m$^2$) | UTS (MPa) | EAB % | YS (MPa) | VI |
|---|---|---|---|---|---|
| 280° C. - 6 h | 153 ± 3.6 | 49.6 ± 1.7 | 434 ± 15 | 21.5 ± 0.3 | 0.02 ± 0.01 |
| 300° C. - 5 h | 112 ± 5.8 | 45.2 ± 1.3 | 492 ± 23 | 22.1 ± 0.7 | 0.04 ± 0.00 |
| 310° C. - 6 h | 92.1 ± 1.3 | 49.9 ± 0.2 | 702 ± 10 | 23.4 ± 0.2 | 0.07 ± 0.01 |
| 320° C. - 6 h | 69.1 ± 1.4 | 48.3 ± 1.1 | 975 ± 43 | 24.3 ± 0.6 | 0.10 ± 0.01 |

GUR 1020 resin was used.
UTS: Ultimate tensile strength;
EAB: elongation at break;
YS: yield strength;
VI: vinyl index;
HTM: high temperature melting Example 4. The Properties of Partially Consolidated, High Temperature Melted and Completely Molded UHMWPE Via the Two-Step Molding Followed by Radiation Cross-Linking GUR1020 UHMWPE resin powder was blended with 2 wt % vitamin E by solvent blending and dried. Further the blend was diluted to 0.2 wt % vitamin E by mixing with virgin GUR1020 powder. The 0.2 wt % vitamin E-blended powder was poured into a cylindrical mold with about 100 mm diameter and compressed with 4000 lbs (~2 MPa) between platens pre-heated to 358 F (181° C.) for 10 minutes, then was cooled down to about room temperature. The pre-molded polymeric material was taken out of the mold and placed in a convection oven pre-heated to temperature. The oven was purged with nitrogen and the nitrogen flow was maintained during heating and maintaining the sample at temperature for the desired amount of time and cooling after this period to about room temperature. Samples were processed at 320° C. for 6 hours. After HTM, the cylindrical pucks were placed back into the consolidation mold and molded completely between platens pre-heated to 381 F (194° C.) for 10 minutes at ~20 MPa, then was cooled down to about room temperature under pressure. Then the pucks were irradiated using electron beam irradiation to 150 kGy, 175 kGy and 200 kGy (n=4 each). After radiation cross-linking, 2 pucks of each radiation dose were annealed in nitrogen at 130° C. for 5 hours.

Tensile testing was performed on dog-bones (Type V, ASTM D-638) stamped out of 3.2 mm-thick sections machined from the final pucks. Testing was performed at 10 mm/min (MTS Insight, Eden Prairie, Minn.). Elongation to break (EAB) was determined by using a laser extensometer. Ultimate tensile strength (UTS) and yield strength (YS) were also measured.

IZOD impact testing was performed on impact coupons (63.5 mm×12.7 mm×6.35 mm) after double notching according to ASTM F648.

Wear testing was done on a custom-designed bidirectional pin-on-disc (POD) tester in undiluted bovine serum. Cylindrical pins (9 mm diameter, 13 mm length) were tested at 2 Hz under a peak load of 440 lbs for 1.2 million cycles (MC). They were weighed and the wear was determined gravimetrically at 500,000 cycles and every 157,000 cycles after that. Wear rate was determined by a linear regression of weight loss as a number of cycles from 500,000 cycles to 1.2 million cycles.

The mechanical properties of these samples are shown in Table 4 and the wear rates are shown in Table 5. The mechanical properties of the partially consolidated puck were as follows: UTS 7.8±0.2 MPa; YS 1.3±0.2 MPa and EAB 8.2±0.9%.

TABLE 4

Tensile mechanical properties of partially consolidated, high temperature melted and completely consolidated 0.2 wt % vitamin E-blended UHMWPE via the two-step molding process followed by irradiation.

| Radiation Dose | IZOD Impact Strength (kJ/m$^2$) | UTS (MPa) | EAB % | YS (MPa) |
| --- | --- | --- | --- | --- |
| 150 kGy | 77 ± 1.5 | 39 ± 2 | 411 ± 13 | 26 ± 0.3 |
| 175 kGy | 73 ± 0.3 | 38 ± 1 | 383 ± 9 | 25 ± 0.1 |
| 200 kGy | 71 ± 1.3 | 40 ± 2 | 306 ± 14 | 26 ± 0.5 |
| 150 kGy annealed | 75 ± 1.7 | 43 ± 1 | 451 ± 13 | 25 ± 0.2 |
| 175 kGy annealed | 67 ± 1.1 | 39 ± 2 | 377 ± 7 | 25 ± 0.7 |
| 200 kGy annealed | 62 ± 0.5 | 38 ± 2 | 339 ± 18 | 24 ± 0.2 |

GUR 1020 resin was used.
UTS: Ultimate tensile strength;
EAB: elongation at break;
YS: yield strength;
VI: vinyl index;
HTM: high temperature melting Also, thin sections (150 μm) were microtomed across the cross-section of the pre-molded, high temperature melted and completely consolidated puck and Fourier transform infrared spectroscopy was used to obtain spectra. Several data points were taken along the depth of the sample at 4 cm$^{-1}$ and average of 32 scans was recorded. A vinyl index was calculated using the area under 880-920 cm$^{-1}$ and normalizing it to the area under 1895 cm$^{-1}$ (1850-1985 cm$^{-1}$). The vinyl index of the said puck before irradiation was 0.09.

Example 5. Comparison of the Properties of Samples Made Using One-Step and Two-Step Molding Processes with High Temperature Melting (HTM)

GUR1020 UHMWPE resin powder was blended with 2 wt % vitamin E by solvent blending and dried. Further the blend was diluted to 0.2 wt % vitamin E by mixing with virgin GUR1020 powder.

For the two-step molding process, the 0.2 wt % vitamin E-blended powder (~100 g) was poured into a cylindrical mold with about 100 mm diameter and compressed with 4000 lbs (~2 MPa) between platens pre-heated to 358 F (181° C.) for 10 minutes, then was cooled down to about room temperature. The pre-molded polymeric material was taken out of the mold and placed in a convection oven pre-heated to temperature. The oven was purged with nitrogen and the nitrogen flow was maintained during heating and maintaining the sample at temperature for the desired amount of time and cooling after this period to about room temperature. Samples were processed at 300 or 310° C. for 6 hours. After HTM, the cylindrical pucks were placed back into the consolidation mold and molded completely between platens pre-heated to 381 F (194° C.) for 10 minutes at ~20 MPa, then was cooled down to about room temperature under pressure.

For the one-step process, the 0.2 wt % vitamin E-blended powder (~100 g) was poured into a cylindrical mold with about 100 mm diameter and compressed at ~20 MPa between platens pre-heated to 381 F (194° C.) for 10 minutes, then was cooled down to about room temperature. The consolidated polymeric material was taken out of the mold and placed in a convection oven pre-heated to temperature. The oven was purged with nitrogen and the nitrogen flow was maintained during heating and maintaining the sample at temperature for the desired amount of time and cooling after this period to about room temperature. Samples were processed at 280, 300, 310 or 320° C. for 6 hours.

The mechanical properties and vinyl index (VI) of the samples are shown in Table 5. Both sets of samples had good properties for consolidated UHMWPE material for use in joint implants.

TABLE 5

Wear rate of partially consolidated, high temperature melted and completely consolidated 0.2 wt % vitamin E-blended UHMWPE via the two-step molding process followed by irradiation.

| Radiation Dose | Wear rate (mg/MC) |
| --- | --- |
| No irradiation | 14.3 ± 0.6 |
| 150 kGy | 1.6 ± 0.9 |
| 175 kGy | 1.4 ± 0.2 |
| 200 kGy | 0.9 ± 0.1 |
| 150 kGy annealed | 1.3 ± 0.2 |
| 175 kGy annealed | 0.7 ± 0.1 |
| 200 kGy annealed | 0.6 ± 0.1 |

GUR 1020 resin was used.
(mg/MC; milligram/million cycle)

TABLE 5

Comparison of the two-step HTM process with the one-step HTM process

| Sample | IZOD Impact Strength (kJ/m$^2$) | UTS (MPa) | EAB % | YS (MPa) | VI |
|---|---|---|---|---|---|
| Partial molding + HTM + Secondary folding | | | | | |
| HTM @ 280° C. - 6 h | 153 ± 3.6 | 50 ± 1.7 | 434 ± 15 | 21.5 ± 0.3 | 0.02 ± 0.01 |
| HTM @ 300° C. - 6 h | 112 ± 5.9 | 49 ± 6.8 | 543 ± 52 | 22.5 ± 0.2 | 0.03 ± 0.00 |
| HTM @ 310° C. - 6 h | 92.1 ± 1.3 | 50 ± 0.2 | 702 ± 10 | 23.4 ± 0.2 | 0.07 ± 0.01 |
| HTM @ 320° C. - 6 h | 69.1 ± 1.4 | 48 ± 1.1 | 975 ± 43 | 24.3 ± 0.6 | 0.10 ± 0.01 |
| Molding + HTM | | | | | |
| HTM @ 300° C. - 6 h | 94.9 ± 1.0 | 50 ± 4.9 | 632 ± 25 | 22.9 ± 0.2 | 0.05 ± 0.00 |
| HTM @ 310° C. - 6 h | 62.3 ± 2.5 | 49 ± 2.0 | 832 ± 61 | 24.0 ± 0.5 | |

Example 6. Comparison of the Properties of Samples Made Using One-Step and Two-Step Molding Processes with High Temperature Melting (HTM) Followed by Irradiation GUR1020 UHMWPE resin powder was blended with 2 wt % vitamin E by solvent blending and dried. Further the blend was diluted to 0.2 wt % vitamin E by mixing with virgin GUR1020 powder.

For the two-step molding process, the 0.2 wt % vitamin E-blended powder (~100 g) was poured into a cylindrical mold with about 100 mm diameter and compressed with 4000 lbs (~2 MPa) between platens pre-heated to 358 F (181° C.) for 10 minutes, then was cooled down to about room temperature. The pre-molded polymeric material was taken out of the mold and placed in a convection oven pre-heated to temperature. The oven was purged with nitrogen and the nitrogen flow was maintained during heating and maintaining the sample at temperature for the desired amount of time and cooling after this period to about room temperature. Samples were processed at 320° C. for 6 hours. After HTM, the cylindrical pucks were placed back into the consolidation mold and molded completely between platens pre-heated to 381 F (194° C.) for 10 minutes at ~20 MPa, then was cooled down to about room temperature under pressure.

For the one-step process, the 0.2 wt % vitamin E-blended powder (~100 g) was poured into a cylindrical mold with about 100 mm diameter and compressed at ~20 MPa between platens pre-heated to 381 F (194° C.) for 10 minutes, then was cooled down to about room temperature. The consolidated polymeric material was taken out of the mold and placed in a convection oven pre-heated to temperature. The oven was purged with nitrogen and the nitrogen flow was maintained during heating and maintaining the sample at temperature for the desired amount of time and cooling after this period to about room temperature. Samples were processed at 320° C. for 6 hours.

Both sets of samples were irradiated to 175 kGy at 25 kGy/pass using electron beam irradiation on a 10 MeV beam line. Some samples of each set were further annealed at 130° C. in nitrogen for 5 hours.

The mechanical properties and wear rate of these samples are shown in Table 6. Both sets of samples had good properties for consolidated UHMWPE material for use in joint implants.

TABLE 6

Comparison of radiation cross-linked, 0.2 wt % vitamin E-blended HTM UHMWPE with the one-step or two-step HTM process. The two-step HTM process involved HTM at 320° for 6 hours followed by complete molding and 175 kGy irradiation. The one-step HTM process involved HTM at 310° for 8 hours followed by 175 kGy irradiation

| Sample | IZOD Impact Strength (kJ/m$^2$) | UTS (MPa) | EAB % | YS (MPa) | Wear rate (mg/MC) |
|---|---|---|---|---|---|
| One-Step | 75.4 ± 1.4 | 42.9 ± 0.8 | 341 ± 12 | 23.2 ± 0.8 | 1.1 ± 0.2 |
| Two-Step | 72.8 ± 0.3 | 37.5 ± 0.5 | 383 ± 9 | 25.3 ± 0.1 | 1.4 ± 0.2 |
| One-Step annealed | 71.2 ± 1.3 | 45.0 ± 0.9 | 359 ± 2 | 21.7 ± 0.9 | 0.8 ± 0.1 |
| Two-Step annealed | 66.7 ± 1.1 | 38.7 ± 1.7 | 377 ± 7 | 24.7 ± 0.7 | 0.7 ± 0.1 |

Example 7. Layered Molding of Pre-Molded, High Temperature Melted UHMWPE and UHMWPE Resin Powder with Cross-Linking Agents GUR1020 UHMWPE resin powder was blended with 2 wt % vitamin E by solvent blending and dried. Further the blend was diluted to 0.2 wt % vitamin E by mixing with virgin GUR1020 powder.

The 0.2 wt % vitamin E-blended powder (~100 g) was poured into a cylindrical mold with about 100 mm diameter and compressed with 4000 lbs (~2 MPa) between platens pre-heated to 358 F (181° C.) for 10 minutes, then was cooled down to about room temperature. The pre-molded polymeric material was taken out of the mold and placed in a convection oven pre-heated to temperature. The oven was purged with nitrogen and the nitrogen flow was maintained during heating and maintaining the sample at temperature for the desired amount of time and cooling after this period to about room temperature. Samples were processed at 320° C. for 6 hours.

GUR1050 UHMWPE resin powder was blended with 2 wt % vitamin E by solvent blending and dried. Further the blend was diluted to 0.8 wt % vitamin E by mixing with virgin GUR1050 powder. The vitamin E-blended UHMWPE was blended further with 1 wt % 2,5-Di(tert-butylperoxy)-2,5-dimethyl-3-hexyne (P130).

After HTM, the pre-molded GUR1020 UHMWPE placed back into the consolidation mold and layered with the vitamin E and P130-blended GUR1050 UHMWPE and molded completely between platens pre-heated to 381 F (194° C.) for 10 minutes at ~20 MPa, then was cooled down to about room temperature under pressure.

IZOD impact testing was performed on impact coupons (63.5 mm×12.7 mm×6.35 mm) after double notching according to ASTM F648.

Wear testing was done on a custom-designed bidirectional pin-on-disc (POD) tester in undiluted bovine serum. Cylindrical pins (9 mm diameter, 13 mm length) were tested at 2 Hz under a peak load of 440 lbs for 1.2 million cycles (MC). They were weighed and the wear was determined gravimetrically at 500,000 cycles and every 157,000 cycles after that. Wear rate was determined by a linear regression of weight loss as a number of cycles from 500,000 cycles to 1.2 million cycles.

The impact strength and the surface wear rate of this layered molded UHMWPE are shown in Table 7.

TABLE 7

The properties of layered molded pre-molded, high temperature melted UHMWPE and cross-link agent-blended UHMWPE powder

| Sample | Impact Strength (kJ/m$^2$) | POD Wear Rate (mg/MC) |
|---|---|---|
| Bulk: 0.8 wt % VE (1020) Pellet + HTM @ 300 C.-5 h + Surface Layer: 0.8 wt % VE (1050)/1 wt % P130 | 125.61 ± 2.75 | 3.13 ± 0.43 |

Example 8. Formation of a Tibial Insert

Figure 6:
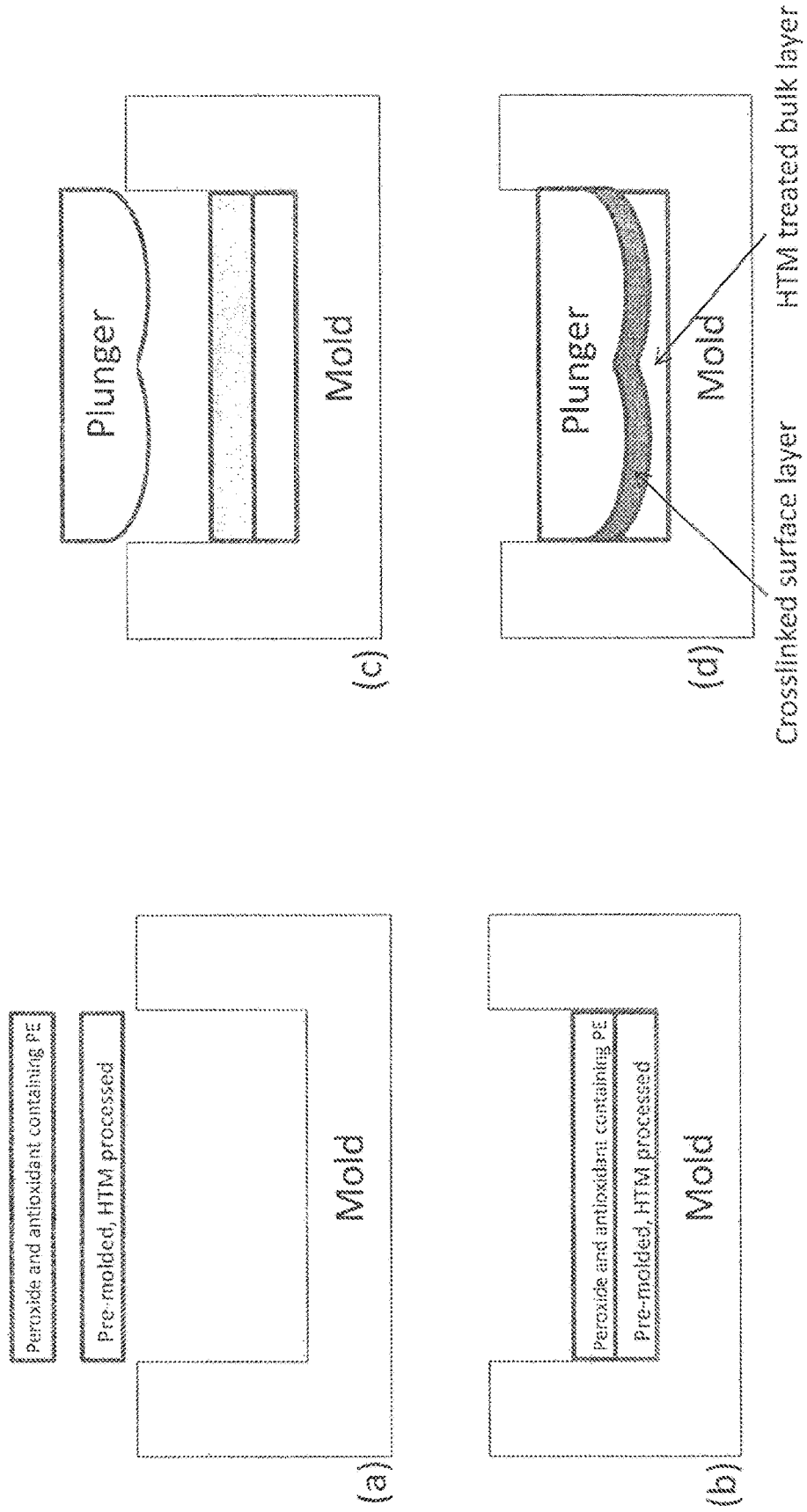
FIG. 6. Example of the formation of a tibial insert with highly cross-linked articular surface with good wear resistance and high temperature melt (HTM) treated bulk with good mechanical properties. The HTM treated bulk layer is prepared by molding a green polyethylene containing vitamin E followed by high temperature melting. Optionally this bulk layer is either fully consolidated first and then used in the molding steps described here or it is used as-is after the HTM step in the molding steps described here. The two layers are placed inside a mold and molded together at elevated temperature and pressure. The pressure is applied by the plunger. In some embodiments it is desirable to have three layers inside the mold. For example first a peroxide and antioxidant containing polyethylene blend at the bottom, then in the middle an HTM processed layer sandwiched between two layers of peroxide and antioxidant containing polyethylene blend.
Figure 7:
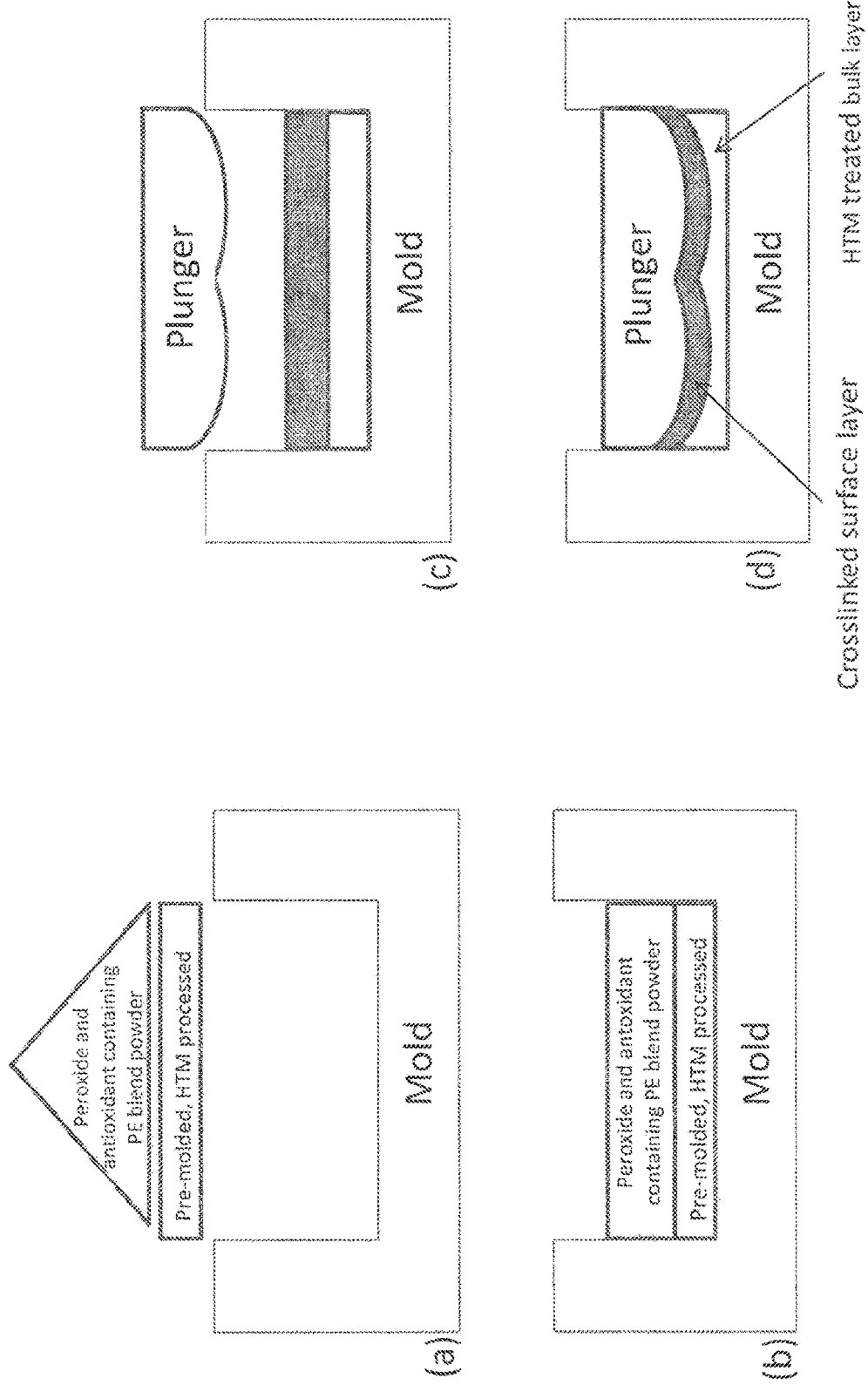
FIG. 7. Example of the formation of a tibial insert with highly cross-linked articular surface with good wear resistance and HTM treated bulk with good mechanical properties. The HTM treated bulk layer is prepared by molding a green polyethylene containing vitamin E followed by high temperature melting. Optionally this bulk layer is either first fully consolidated first and then used in molding steps described here or it is used as-is after the HTM step in the molding steps described here. The peroxide and antioxidant containing polyethylene blend is in the form of a powder blend; in some instances the terms "resin" and "powder" are used interchangeably. After the placement of the HTM processed layer into the mold, the powder blend is uniformly spread on top of the HTM processed layer. The two layers are then molded together at elevated temperature and pressure. The pressure is applied by the plunger. In some embodiments it is desirable to have three layers inside the mold. For example first a peroxide and antioxidant containing polyethylene blend at the bottom, then in the middle an HTM processed layer, and finally at the top another peroxide and antioxidant containing polyethylene blend. In some embodiments it is desirable to have three layers inside the mold. For example first a peroxide and antioxidant containing polyethylene blend powder at the bottom, then in the middle an HTM processed layer, and finally at the top another layer of peroxide and antioxidant containing polyethylene blend powder.

FIGS. 6 and 7 show the formation of a tibial insert with highly cross-linked articular surface with good wear resistance and HTM treated bulk with good mechanical properties. The HTM treated bulk layer is prepared by molding a green polyethylene containing vitamin E followed by high temperature melting. Optionally, this bulk layer is either fully consolidated first and then used in the molding steps described here, or it is used as-is after the HTM step in the molding steps described here.

The two layers are placed inside a mold and molded together at elevated temperature and pressure. The pressure is applied by the plunger. In some embodiments, it is desirable to have three layers inside the mold. For example first a peroxide and antioxidant containing polyethylene blend at the bottom, then in the middle an HTM processed layer, and finally at the top another peroxide and antioxidant containing polyethylene blend (FIG. 6). In a second example, first a peroxide and antioxidant containing polyethylene blend powder at the bottom, then in the middle an HTM processed layer, and finally at the top another layer of peroxide and antioxidant containing polyethylene blend powder (FIG. 7).

Example 9. Blending of Polymeric Material with Antioxidant(s)

Medical grade GUR1020 and GUR1050 UHMWPEs (Celanese, Tex., USA) were blended with 0.8 wt % vitamin E by first preparing a master batch containing 2 wt % vitamin E with the aid of isopropyl alcohol (IPA). Vitamin E was dissolved in IPA at room temperature and the solution was mixed with the medical grade UHMWPE (either with GUR 1020 or GUR 1050). The IPA was then evaporated to obtain master batches of vitamin E/UHMWPE blends either with GUR 1020 or GUR 1050. Then, the two master batches (also called master blends of vitamin E/UHMWPE here) were separately diluted to the desired vitamin E concentration by mixing with virgin (by virgin is meant UHMWPE with no antioxidant or cross-linking agent added) GUR 1020 or GUR 1050.

Example 10. Blending of Antioxidant-Blended UHMWPE with Cross-Linking Agent

An approximately 100 g batch of 0.8 wt % vitamin E-blended UHMWPE was prepared by mixing either of the 2 wt % master batches with the virgin corresponding UHMWPE resin (i.e. GUR 1020 or GUR 1050). These were then individually mixed with pure peroxide (2,5-dimethyl-2,5-Di-(tbutylperoxy)hexyne-3, also called Luperox 130, peroxide 130 or DYBP or P130) in the concentrations of 0.5, 1.0 or 1.5 wt % peroxide.

Example 11. Oxidation Induction Time (OIT) Testing

The oxidation induction time (OIT) was determined using a differential scanning calorimeter (DSC) (Discovery™, TA Instruments, Newark, Del., USA), which was calibrated by indium as the standard. The test was performed in accordance with an ISO standard (ISO11357-6: 2002). Small samples (~5 mg, n=3 each) were placed in an uncovered $T_0$ pan (an open DSC pan) and heated from 20 to 200° C. at a rate of 20° C./min under a nitrogen flow of 50 ml/min. After maintaining nitrogen flow for 5 minutes at 200° C. to attain thermal equilibrium, the gas was then switched from nitrogen to oxygen at a flow rate of 50 ml/min (marked as the start point of experiment). The onset of oxidation (exothermic reaction) was recorded as the OIT in minutes, and was determined as the intercept of the extended baseline and the steepest tangent drawn to the exotherm.

Example 12. Cross-Link Density Measurements

The cross-link density was measured using small sections (approximately 3×3×3 mm, n=3 each) prepared manually by cutting with a razor blade. The samples were placed in 25 mL of pre-heated xylene at 130° C. in an oil bath and were allowed to swell for 2 hours. The dry sample weight and the swollen sample weight were measured in sealed containers before and after xylene immersion to determine a gravimetric swell ratio. The gravimetric swelling ratio was converted to a volumetric swelling ratio using the density of the dry polymer as 0.94 g/cm$^3$ and the density of xylene at 130° C. as 0.75 g/cm$^3$. The cross-link density of the samples (n=3 each) was calculated using the following equations:

$$d_x = \frac{\ln(1 - q_{eq}^{-1}) + q_{eq}^{-1} + X q_{eq}^{-2}}{V_1(q_{eq}^{-1/3} - q_{eq}^{-2})} \quad \text{(Eq. 1)}$$

$$X = 0.33 + \frac{0.55}{q_{eq}} \quad \text{(Eq. 2)}$$

where the specific volume of xylene, $V_1$, was 136 cm$^3$/mol.

Example 13. Bidirectional Pin-On-Disc (POD) Wear Testing

Wear testing was done on a custom-designed bidirectional pin-on-disc (POD) tester in undiluted bovine serum. Cylindrical pins (9 mm diameter, 13 mm length) were tested using a 5×10 mm rectangular pattern of articulation at 2 Hz under a peak load of 440 lbs for 1.2 million cycles (MC). They were weighed and the wear was determined gravimetrically at daily intervals. Wear rate was determined by a linear regression of weight loss as a function of number of cycles. The wear rate was reported in milligrams/million cycle (mg/MC).

Example 14. Tensile Mechanical Testing

Tensile testing was performed on dog-bones (Type V, ASTM D-638) stamped out of 3.2 mm-thick sections machined from the prepared pucks. Testing was performed at a grip displacement speed of 10 mm/min (MTS Insight, Eden Prairie, Minn.). Elongation to break (EAB) was determined by using a laser extensometer. Ultimate tensile strength (UTS) and yield strength (YS) were also measured.

Example 15. IZOD Impact Testing

IZOD impact testing was performed on impact coupons (63.5 mm×12.7 mm×6.35 mm) after double notching according to ASTM F648.

Example 16. The Effect of High Temperature Melting on 0.8 wt % Vitamin E-Blended, Peroxide Cross-Linked UHMWPEs An approximately 100 g batch of 0.8 wt % vitamin E-blended UHMWPE was prepared by mixing either of the 2 wt % master batches described above with the virgin corresponding UHMWPE resins (i.e. GUR 1020 or GUR 1050). These were then individually mixed with pure peroxide (2,5-dimethyl-2,5-Di-(tbutylperoxy)hexyne-3, also called Luperox 130, peroxide 130 or DYBP or P130) in the concentrations of 0.5, 1.0 or 1.5 wt % peroxide.

The vitamin E and peroxide-blended UHMWPE batches were compression molded on a laboratory press at 190° C. for 2 hours and cooled under pressure to below their melting point, resulting in cylindrical pucks with an approximate diameter of 10.5 cm and a thickness of 1 cm.

The resulting pucks were either tested 'as is' or further treated by high temperature melting at 300, 310 or 320° C. for 5 hours and then cooling in nitrogen in a convection oven.

Samples were tested for oxidation induction time (OIT), cross-link density, POD wear rates, tensile mechanical properties and IZOD impact strength as described above in Examples 11, 12, 13, 14 and 15.

TABLE 8-1

The physicochemical and tensile mechanical properties of 0.8 wt % vitamin E-blended and 1 wt % peroxide-blended UHMWPEs before and after further high temperature melting. OIT denotes 'Oxidation Induction time'; CLD denotes 'Cross-link density'; UTS denotes 'Ultimate tensilestrength' and EAB denotes 'Elongation at break'.

| Sample | OIT (mins) | CLD (mol/m$^3$) | Wear (mg/MC) | UTS (MPa) | EAB (%) | Impact Strength (kJ/m$^2$) |
|---|---|---|---|---|---|---|
| GUR 1050 group | | | | | | |
| No HTM | 27.3 | 259 ± 5 | 2.2 ± 0.0 | 41.0 ± 3.0 | 309 ± 14 | 77.1 ± 0.5 |
| HTM @ 300° C.-5 h | Not-tested | 169 ± 7 | 1.7 ± 0.1 | 36.6 ± 7.1 | 338 ± 31 | 94.2 ± 0.7 |
| HTM @ 310° C.-5 h | 45.6 ± 2.0 | 124 ± 2 | Not-tested | 42.4 ± 6.0 | 388 ± 5 | Not-tested |
| HTM @ 320° C.-5 h | 42.8 ± 2.0 | 157 ± 6 | 2.2 ± 0.0 | 42.6 ± 2.3 | 454 ± 9 | 108 ± 1.3 |
| GUR 1020 group | | | | | | |
| No HTM | Not-tested | 206 ± 4 | Not-tested | 41.0 ± 2.0 | 292 ± 5 | 80.4 ± 0.8 |
| HTM @ 310° C.-5 h | 46.8 ± 2.3 | 114 ± 21 | Not-tested | 43.2 ± 4.2 | 422 ± 17 | Not-tested |

The UHMWPE blends cross-linked during compression molding. The subsequent HTM decreased cross-link density regardless of the HTM temperature used. After HTM, oxidation induction time was increased. Wear rate and UTS were not significantly changed after HTM. EAB and IZOD impact strength were significantly increased after HTM; suggesting increased ductility and toughness.

Typically the wear rate of uncrosslinked UHMWPE would be around 8-10 mg/mc. Peroxide crosslinking achieved during compression was able to reduce the wear rate.

Example 17. The Effect of High Temperature Melting on 0.5 wt % Vitamin E-Blended, Peroxide Cross-Linked UHMWPEs Approximately 100 g batch of 0.5 wt % vitamin E-blended UHMWPE was prepared by mixing the 2 wt % vitamin E/GUR 1050 UHMWPE master batch of Example 9 with the virgin GUR 1050 UHMWPE, which was then mixed with pure P130 in the amount of 0.9 wt % peroxide.

The vitamin E and peroxide-blended UHMWPE batch was compression molded on a laboratory press at 190° C. for 2 hours and cooled under pressure to below its melting point, resulting in a cylindrical puck with an approximate diameter of 10.5 cm and a thickness of 1 cm.

The resulting pucks were either tested 'as is' or further treated by high temperature melting at 300, 310 or 320° C. for 5 hours and then cooling in nitrogen in a convection oven.

Samples were tested to determine oxidation induction time, crosslink density, POD wear rate, tensile mechanical properties, and IZOD impact strength using methods described in Examples 11, 12, 13, 14 and 15.

at all temperatures. After HTM, oxidation induction time was increased. UTS was not affected substantially. Wear rate was increased only after melting at 320° C. EAB and IZOD impact strength were significantly increased at all HTM temperatures; suggesting increased ductility and toughness.

Example 18. The Effect of Peroxide Concentration on the Properties after HTM of 0.5 wt % Vitamin E-Blended GUR1050 and GUR 1020 UHMWPEs An approximately 100 g batch of 0.5 wt % vitamin E-blended GUR 1050 UHMWPE was prepared by mixing the 2 wt % vitamin E/GUR 1050 UHMWPE master batch of Example 9 with the virgin GUR 1050 UHMWPE, which was then mixed with P130 in the amounts of 0.7, 0.9 or 1.1 wt % peroxide. Similarly, a ~100 g batch of the 0.5 wt % vitamin E-blended GUR 1020 UHMWPE was mixed with P130 in the amounts of 0.9, 1.0 or 1.1 wt % peroxide.

The vitamin E and peroxide-blended UHMWPE blends were compression molded on a laboratory press at 190° C. for 2 hours and cooled under pressure to below its melting point, resulting in a cylindrical puck with an approximate diameter of 10.5 cm and a thickness of 1 cm.

The resulting pucks were either tested 'as is' or further treated by high temperature melting at 310° C. for 5 hours and then cooling in nitrogen in a convection oven.

Samples were tested to determine oxidation induction time, crosslink density, POD wear rate, tensile mechanical properties, and IZOD impact strength using methods described in Example 11, 12, 13, 14, and 15.

TABLE 9-1

The physicochemical and tensile mechanical properties of 0.5 wt % vitamin E-blended and 0.9 wt % peroxide-blended UHMWPEs before and after further high temperature melting. OIT denotes 'Oxidation Induction time'; CLD denotes 'Cross-link density'; UTS denotes 'Ultimate tensile strength' and EAB denotes 'Elongation at break'.

| Sample | OIT (mins) | CLD (mol/m$^3$) | Wear (mg/MC) | UTS (MPa) | EAB (%) | Impact Strength (kJ/m$^2$) |
|---|---|---|---|---|---|---|
| No HTM | 20.9 ± 0.4 | 252 ± 10 | 1.3 ± 0.2 | 36.9 ± 3.7 | 291 ± 15 | 77.2 ± 0.6 |
| HTM @ 300° C.-5 h | 31.5 ± 2.1 | 166 ± 4 | 1.4 ± 0.2 | 36.2 ± 4.4 | 399 ± 36 | 92.7 ± 1.1 |
| HTM @ 310° C.-5 h | 27.1 ± 5.1 | 124 ± 3 | 1.4 ± 0.2 | 39.3 ± 2.2 | 420 ± 9 | 99.7 ± 0.7 |
| HTM @ 320° C.-5 h | 36.5 ± 1.4 | 78 ± 1 | 2.2 ± 1.2 | 35.2 ± 6.5 | 411 ± 39 | 101 ± 3.3 |

The UHMWPE blends cross-linked during compression molding. The subsequent HTM decreased cross-link density

TABLE 10-1

The physicochemical and tensile mechanical properties of 0.5 wt % vitamin E-blended peroxide-blended GUR 1050 UHMWPEs before and after further high temperature melting.

| Sample | OIT (mins) | CLD (mol/m$^3$) | Wear (mg/MC) | UTS (MPa) | EAB (%) | Impact Strength (kJ/m$^2$) |
|---|---|---|---|---|---|---|
| 0.7 wt % peroxide | | | | | | |
| No HTM | 19.5 ± 1.6 | 235 ± 6 | 2.3 ± 0.3 | 40.8 ± 5.2 | 331 ± 12 | 79.8 ± 0.4 |
| HTM @ 310° C. | 24.2 ± 3.6 | 88 ± 1 | 4.5 ± 2.0 | 45.2 ± 1.8 | 416 ± 20 | 112 ± 1.3 |

TABLE 10-1-continued

The physicochemical and tensile mechanical properties of 0.5 wt % vitamin
E-blended peroxide-blended GUR 1050 UHMWPEs before and after further
high temperature melting.

| Sample | OIT (mins) | CLD (mol/m³) | Wear (mg/MC) | UTS (MPa) | EAB (%) | Impact Strength (kJ/m²) |
|---|---|---|---|---|---|---|
| 0.9 wt % peroxide | | | | | | |
| No HTM | 20.9 ± 0.4 | 252 ± 10 | 1.3 ± 0.2 | 36.9 ± 3.7 | 291 ± 15 | 77.2 ± 0.6 |
| HTM @ 310° C. | 27.1 ± 5.1 | 124 ± 3 | 1.4 ± 0.2 | 39.3 ± 2.2 | 420 ± 9 | 99.7 ± 0.7 |
| 1.1 wt % peroxide | | | | | | |
| No HTM | 20.3 | 256 ± 12 | 1.2 ± 0.2 | 36.7 ± 2.4 | 224 ± 74 | 69.5 ± 0.4 |
| HTM @ 310° C. | 23.8 | 165 ± 7 | 0.7 ± 0.1 | 31.6 ± 1.9 | 353 ± 14 | 88.2 ± 0.7 |

OIT denotes 'Oxidation Induction time';
CLD denotes 'Cross-link density';
UTS denotes 'Ultimate tensile strength' and
EAB denotes 'Elongation at break'.

For 0.5 wt % vitamin E-blended and peroxide-crosslinked GUR1050 UHMWPE (Table 10-1), high temperature melting increased OIT, EAB and impact strength and decreased cross-link density for all peroxide concentrations. The wear rate increased for the lowest concentration of peroxide. The wear rate did not change for 0.9 wt % peroxide and decreased for 1.1 wt % peroxide.

For 0.5 wt % vitamin E-blended and peroxide-cross-linked, high temperature melted GUR1020 UHMWPE (Table 10-2), increasing peroxide concentration decreased wear rate, EAB and impact strength but did not significantly change the other measured properties. Compared to 0.5 wt % vitamin E-blended, peroxide cross-linked UHMWPE using the same peroxide concentration (0.9 and 1.1 wt %; Table 10-1), OIT and wear rate were higher, impact strength was lower and there were no significant changes in the other measured properties.

TABLE 10-2

The physicochemical and tensile mechanical properties of 0.5 wt %
vitamin E-blended peroxide-blended GUR 1020 UHMWPEs before
and after further high temperature melting.

| Sample | OIT (mins) | CLD (mol/m³) | Wear (mg/MC) | UTS (MPa) | EAB (%) | Impact Strength (kJ/m²) |
|---|---|---|---|---|---|---|
| 0.9 wt % peroxide | | | | | | |
| HTM @ 310° C. | 39.4 ± 2.9 | 124 ± 5 | 2.3 ± 1.2 | 44.1 ± 3.1 | 428 ± 12 | 99.0 ± 0.1 |
| 1.0 wt % peroxide | | | | | | |
| HTM @ 310° C. | 38.5 ± 1.4 | 135 ± 5 | 0.9 ± 0.1 | 41.1 ± 1.9 | 412 ± 8 | 94.4 ± 0.4 |
| 1.1 wt % peroxide | | | | | | |
| HTM @ 310° C. | 37.9 ± 2.2 | 137 ± 1 | Not-tested | 43.2 ± 1.8 | 374 ± 7 | 90.3 ± 0.6 |

OIT denotes 'Oxidation Induction time';
CLD denotes 'Cross-link density';
UTS denotes 'Ultimate tensile strength' and
EAB denotes 'Elongation at break'.

Example 19. The Use of Other Antioxidants in Peroxide Cross-Linked and/or High Temperature Melted UHMWPEs Medical grade GUR1050 UHMWPE (Celanese, Tex., USA) was blended with 0.5 wt % antioxidants. The antioxidants used were vitamin E, vitamin E acetate, or Irganox 1010 (Pentaerythritol tetrakis(3-(3,5-di-tert-butyl-4-hydroxyphenyl)propionate) by first preparing a master batch of antioxidant/UHMWPE blend containing 2 wt % antioxidant with the aid of isopropyl alcohol (IPA) as described above in Example 9. Then, the master batch was diluted to the desired concentration by mixing with virgin GUR 1050 UHMWPE.

An approximately 100 g batch of 0.5 wt % antioxidant-blended GUR 1050 UHMWPE was prepared by separately mixing the three types of 2 wt % antioxidant/GUR 1050 UHMWPE master batch with the virgin GUR 1050 UHMWPE (Example 9), which was then mixed with P130 in the amount of 0.9 wt % peroxide. Thus, three separate blends were prepared and tested: (i) 0.5 wt % vitamin E/0.9 wt % P130/GUR 1050 UHMWPE, (ii) 0.5 wt % vitamin acetate/0.9 wt % P130/GUR 1050 UHMWPE, (iii) 0.5 wt % Irganox/0.9 wt % P130/GUR 1050 UHMWPE.

The vitamin E and peroxide-blended UHMWPE batches were compression molded on a laboratory press at 190° C. for 2 hours and cooled under pressure to below its melting point, resulting in a cylindrical puck with an approximate diameter of 10.5 cm and a thickness of 1 cm.

The resulting pucks were either tested 'as is' or further treated by high temperature melting at 310° C. for 5 hours and then cooling in nitrogen in a convection oven.

Samples were tested to determine oxidation induction time, crosslink density, POD wear rate, tensile mechanical properties, and IZOD impact strength using methods described in Example 11, 12, 13, 14 and 15.

TABLE 11-1

The physicochemical and tensile mechanical properties of antioxidant-blended, 0.9 wt % peroxide-blended GUR 1050 UHMWPEs before and after further high temperature melting. The antioxidants used were vitamin E, vitamin E acetate and Irganox 1010.

| Sample | OIT (mins) | CLD (mol/m$^3$) | Wear (mg/MC) | UTS (MPa) | EAB (%) | Impact Strength (kJ/m$^2$) |
|---|---|---|---|---|---|---|
| Vitamin E | | | | | | |
| HTM @ 310° C. | 27.1 ± 5.1 | 124 ± 3 | 1.4 ± 0.2 | 39.3 ± 2.2 | 420 ± 9 | 99.7 ± 0.7 |
| Vitamin E acetate | | | | | | |
| HTM @ 310° C. | 18.1 ± 0.3 | 102 ± 6 | Not-tested | 40.2 ± 2.1 | 401 ± 11 | 83.0 ± 3.5 |
| Irganox ® 1010 | | | | | | |
| HTM @ 310° C. | 27.4 ± 1.8 | 116 ± 3 | 0.5 ± 0.2 | 39.9 ± 0.8 | 364 ± 6 | 87.2 ± 0.6 |

OIT denotes 'Oxidation Induction time';
CLD denotes 'Cross-link density';
UTS denotes 'Ultimate tensile strength' and
EAB denotes 'Elongation at break'.

Both the vitamin E acetate and Irganox-blended, peroxide cross-linked UHMWPEs were lighter in color than the vitamin E-blended, peroxide cross-linked UHMWPE both after compression molding and after high temperature melting.

The OIT, cross-link density and impact strength of vitamin E-acetate blended, peroxide cross-linked UHMWPE were lower than the vitamin E-blended, peroxide cross-linked UHMWPE (Table 11-1). The UTS and EAB did not change considerably between the two antioxidant types.

The wear rate, EAB and impact strength of Irganox-blended, peroxide cross-linked UHMWPE were lower than the vitamin E-blended, peroxide cross-linked UHMWPE. The OIT, cross-link density, and the UTS did not change considerably between the two antioxidant types. These results suggested that peroxide cross-linking and high temperature melting were feasible and effective in cross-linking and improving the oxidation stability in UHMWPE using blending with antioxidants other than vitamin E. Antioxidant and peroxide concentration can be varied together with consolidation parameters and thermal treatment parameters to optimize OIT, UTS strength, Izod strength, and wear.

Example 20. The Use of Irganox® 1010 in Peroxide Cross-Linked and/or High Temperature Melted UHMWPEs Medical grade GUR1050 UHMWPE (Celanese, Tex., USA) was blended with 0.5 wt % Irganox 1010 (Pentaerythritol tetrakis(3-(3,5-di-tert-butyl-4-hydroxyphenyl)propionate) by first preparing a master batch of Irganox 1010/ UHMWPE blend containing 2 wt % Irganox 1010 with the aid of isopropyl alcohol (IPA) as described above in Example 9. Then, the master blend was diluted to the desired concentration by mixing with virgin GUR 1050 UHMWPE.

An approximately 100 g batch of 0.5 wt % Irganox-blended GUR 1050 UHMWPE was prepared by mixing the 2 wt % Irganox 1010/GUR 1050 UHMWPE master batch with the virgin GUR 1050 UHMWPE, which was then mixed with P130.

Medical grade GUR1020 UHMWPE (Celanese, Tex., USA) was blended with 0.5 wt % Irganox 1010 (Pentaerythritol tetrakis(3-(3,5-di-tert-butyl-4-hydroxyphenyl)propionate) by first preparing a master batch containing 2 wt % of Irganox 1010 with the aid of isopropyl alcohol (IPA). Then, the master batch was diluted to the desired concentration by mixing with virgin GUR 1020 UHMWPE.

A ~100 g batch of the 0.5 wt % Irganox-blended GUR 1020 UHMWPE was mixed with P130 (2,5-dimethyl-2,5-Di-(tbutylperoxy)hexyne-3, also called Luperox 130, peroxide 130 or DYBP) in the amount of 0.9 wt % peroxide.

The Irganox 1010 and peroxide-blended UHMWPE batches were compression molded on a laboratory press at 190° C. for 2 hours and cooled under pressure to below its melting point, resulting in a cylindrical puck with an approximate diameter of 10.5 cm and a thickness of 1 cm.

The resulting pucks were either tested 'as is' or further treated by high temperature melting at 310° C. for 5 hours and then cooling in nitrogen in a convection oven.

Samples were tested to determine oxidation induction time, crosslink density, POD wear rate, tensile mechanical properties, and IZOD impact strength using methods described in Example 11, 12, 13, 14, and 15.

TABLE 12-1

The physicochemical and tensile mechanical properties of 0.5 wt % Irganox-blended, peroxide cross-linked GUR 1050 UHMWPEs after further high temperature melting at 310° C.

| Sample | OIT (mins) | CLD (mol/m$^3$) | Wear (mg/MC) | UTS (MPa) | EAB (%) | Impact Strength (kJ/m$^2$) |
|---|---|---|---|---|---|---|
| 0.3 wt % peroxide | 21.0 | 48 ± 9 | 8.8 ± 1.0 | 50.2 ± 3.7 | 473 ± 21 | 123 ± 0.8 |
| 0.5 wt % peroxide | >60 | 127 ± 1 | 4.3 ± 0.4 | 44.9 ± 3.0 | 431 ± 13 | 95.2 ± 0.9 |
| 0.6 wt % peroxide | Not-tested | 94 ± 3 | 2.5 ± 1.1 | Not-tested | Not-tested | 94.5 ± 1.2 |
| 0.7 wt % peroxide | 35.9 | 104 ± 1 | 1.6 ± 1.4 | 44.6 ± 1.8 | 390 ± 7 | 95.3 ± 0.4 |
| 0.8 wt % peroxide | Not-tested | 159 ± 7 | 2.4 ± 1.4 | 33.1 ± 4.5 | 325 ± 19 | 87.8 ± 0.4 |
| 0.9 wt % peroxide | 27.4 | 116 ± 3 | 0.5 ± 0.2 | 39.9 ± 0.8 | 364 ± 6 | 87.2 ± 0.6 |
| 1.0 wt % peroxide | 25.3 | 155 ± 1 | 1.0 ± 0.5 | Not-tested | Not-tested | 78.8 ± 0.7 |

OIT denotes 'Oxidation Induction time';
CLD denotes 'Cross-link density';
UTS denotes 'Ultimate tensile strength' and
EAB denotes 'Elongation at break'.

For 0.5 wt % Irganox-blended, peroxide cross-linked, high temperature melted UHMWPE, the wear rate, the UTS, the EAB and impact strength generally decreased with increasing peroxide concentration and generally decreased with increasing peroxide concentration (Table 12-1).

As a comparison, 0.075 wt % Irganox-blended, 75 kGy radiation cross-linked UHMWPE typically has an OIT of 3 minutes, a wear rate of 3.6 mg/MC, a UTS of 48.0 MPa, an EAB of 291% and an impact strength of 82 kJ/m$^2$. It is clear that for a comparable wear rate, the OIT, the EAB and the impact strength would be improved using peroxide cross-linking and high temperature melting.

TABLE 12-2

The physicochemical and tensile mechanical properties of 0.5 wt % Irganox-blended, peroxide cross-linked GUR 1020 UHMWPEs after further high temperature melting at 310° C.

| Sample | OIT (mins) | CLD (mol/m$^3$) | Wear (mg/MC) | UTS (MPa) | EAB (%) | Impact Strength (kJ/m$^2$) |
|---|---|---|---|---|---|---|
| 0.9 wt % peroxide | Not-tested | 143 ± 5 | 1.5 ± 0.8 | 36.9 ± 0.8 | 356 ± 14 | 80.3 ± 4.4 |

OIT denotes 'Oxidation Induction time';
CLD denotes 'Cross-link density';
UTS denotes 'Ultimate tensile strength' and
EAB denotes 'Elongation at break'.

Compared to the GUR1050 counterpart as shown in Table 12-1, the 0.5 wt % Irganox 1010-blended, 0.9 wt % peroxide cross-linked GUR1020 UHMWPE exhibited higher cross-link density, higher wear rate, lower UTS, similar EAB and lower impact strength (Table 12-2).

Example 21. The Use of Low Concentrations of Irganox 1010 (0.1 to 0.3 wt %) in Peroxide Cross-Linked and/or High Temperature Melted UHMWPEs Medical grade GUR1050 UHMWPE (Celanese, Tex., USA) was blended with 0.1 or 0.3 wt % Irganox 1010 (Pentaerythritol tetrakis(3-(3,5-di-tert-butyl-4-hydroxyphenyl)propionate) by first preparing a master batch of Irganox 1010/UHMWPE blend containing 2 wt % Irganox 1010 with the aid of isopropyl alcohol (IPA) as described above in Example 9. Then, the master blend was diluted to the desired concentration by mixing with virgin UHMWPE.

An approximately 100 g batch of 0.1 wt % Irganox-blended GUR 1050 UHMWPE was prepared by mixing the 2 wt % Irganox 1010 GUR 1050 UHMWPE master batch with the virgin GUR 1050 UHMWPE, which was then mixed with P130 in the amount of 0.3, 0.5, or 0.7 wt % peroxide.

An approximately 100 g batch of 0.3 wt % Irganox-blended GUR 1050 UHMWPE was prepared by mixing the 2 wt % Irganox 1010 GUR 1050 UHMWPE master batch with the virgin GUR 1050 UHMWPE, which was then mixed with P130 in the amount of 0.3, 0.5, 0.7, or 0.9 wt % peroxide.

The Irganox 1010 and peroxide-blended UHMWPE batches were compression molded on a laboratory press at 190° C. for 2 hours and cooled under pressure to below its melting point, resulting in a cylindrical puck with an approximate diameter of 10.5 cm and a thickness of 1 cm.

The resulting pucks were either tested 'as is' or further treated by high temperature melting at 310° C. for 5 hours and then cooling in nitrogen in a convection oven.

Samples were tested to determine oxidation induction time, crosslink density, POD wear rate, tensile mechanical properties, and IZOD impact strength using methods described in Example 11, 12, 13, 14, and 15.

TABLE 13-1

The physicochemical and tensile mechanical properties of 0.3 and 0.1 wt % Irganox-blended, peroxide cross-linked GUR 1050 UHMWPEs after further high temperature melting at 310° C.

| Sample | OIT (mins) | CLD (mol/m$^3$) | Wear (mg/MC) | UTS (MPa) | EAB (%) | Impact Strength (kJ/m$^2$) |
|---|---|---|---|---|---|---|
| 0.3 wt % Irganox 1010 | | | | | | |
| 0.3 wt % peroxide | 42.3 | 50 ± 2 | 7.5 ± 1.6 | 53.4 ± 1.1 | 550 ± 6 | 120 ± 0.6 |
| 0.5 wt % peroxide | Not-tested | 90 ± 7 | Not-tested | 45.8 ± 4.6 | 465 ± 22 | Not-tested |
| 0.7 wt % peroxide | 19.9 | 116 ± 2 | Not-tested | 41.4 ± 1.2 | 419 ± 10 | Not-tested |
| 0.9 wt % peroxide | 20.0 | 151 ± 11 | 1.0 ± 0.5 | 37.6 ± 4.4 | 360 ± 19 | 82.2 ± 1.8 |
| 0.1 wt % Irganox 1010 | | | | | | |
| 0.3 wt % peroxide | 17.4 | 91 ± 3 | 6.1 ± 2.1 | 51.8 ± 1.7 | 482 ± 12 | 109 ± 0.5 |
| 0.5 wt % peroxide | 7.9 | 147 ± 4 | 2.7 ± 1.1 | Not-tested | Not-tested | 91.2 ± 1.3 |
| 0.7 wt % peroxide | Not-tested | 181 ± 3 | 1.7 ± 0.3 | Not-tested | Not-tested | 76.3 ± 2.5 |

OIT denotes 'Oxidation Induction time';
CLD denotes 'Cross-link density';
UTS denotes 'Ultimate tensile strength' and
EAB denotes 'Elongation at break'.

For low concentration Irganox-blended, peroxide cross-linked, high temperature melted UHMWPEs (Table 6-1), increasing peroxide concentration led to decreased OIT, increased cross-link density, decreased wear rate, decreased EAB, decreased UTS and decreased impact strength.

As a comparison, 0.075 wt % Irganox-blended, 75 kGy radiation cross-linked GUR1020 UHMWPE typically has an OIT of 3 minutes, a wear rate of 3.6 mg/MC, a UTS of 48.0 MPa, an EAB of 291% and an impact strength of 82 kJ/m$^2$. It is clear that for a comparable wear rate, the OIT, the EAB and the impact strength would be improved (approximately 44% for EAB and 15% for impact strength using linear intrapolation) using peroxide cross-linking and high temperature melting. A 0.075 wt % Irganox-blended, 0.7 wt % peroxide cross-linked GUR1020 UHMWPE high temperature melted at 310° C. for 5 hours had an OIT of 6.1 minutes, a wear rate of 2.16 mg/MC and an impact strength of 81.8 kJ/m$^2$.

Example 22. The Effect of Peroxide Concentration on the Properties of Low Vitamin E Concentration (0.1-0.3 wt %) Blended, Peroxide Cross-Linked, High Temperature Melted UHMWPE Medical grade GUR1020 and GUR1050 UHMWPEs (Celanese, Tex., USA) were blended with 0.1, 0.2 or 0.3 wt % vitamin E by first preparing a master batch of vitamin E/UHMWPE blend containing 2 wt % vitamin E with the aid of isopropyl alcohol (IPA) as described above in Example 9. Then, the master blend was diluted to the desired concentration by mixing with virgin GUR 1020 or GUR 1050 UHMWPE.

An approximately 100 g batch of the vitamin E-blended UHMWPE of each GUR 1050 and GUR 1020 were prepared by individually mixing the 2 wt % vitamin E master batches with the virgin GUR 1050 or GUR 1020 UHMWPE, which were then mixed with P130.

The vitamin E and peroxide-blended UHMWPE batches were compression molded on a laboratory press at 190° C. for 2 hours and cooled under pressure to below its melting point, resulting in a cylindrical puck with an approximate diameter of 10.5 cm and a thickness of 1 cm.

The resulting pucks were either tested 'as is' or further treated by high temperature melting at 310° C. for 5 hours and then cooling in nitrogen in a convection oven. The test results are shown in Tables 14-1 and 14-2.

Samples were tested to determine oxidation induction time, crosslink density, POD wear rate, tensile mechanical properties, and IZOD impact strength using methods described in example 11, 12, 13, 14, and 15.

TABLE 14-1

The physicochemical and tensile mechanical properties of 0.3, 0.2 and 0.1 wt % Vitamin E-blended, peroxide cross-linked GUR 1050 UHMWPEs after further high temperature melting at 310° C.

| Sample | OIT (mins) | CLD (mol/m$^3$) | Wear (mg/MC) | UTS (MPa) | EAB (%) | Impact Strength (kJ/m$^2$) |
|---|---|---|---|---|---|---|
| 0.3 wt % Vitamin E | | | | | | |
| 0.8 wt % peroxide | 33.9 | 135 ± 2 | Not-tested | Not-tested | Not-tested | 93.4 ± 0.6 |
| 1.0 wt % peroxide | 19.8 | 147 ± 15 | Not-tested | Not-tested | Not-tested | 83.2 ± 0.5 |
| 0.2 wt % Vitamin E | | | | | | |
| 0.7 wt % peroxide | 19.6 | 117 ± 1 | 1.0 ± 0.1 | 42.8 ± 2.8 | 396 ± 27 | 94.8 ± 0.8 |
| 0.9 wt % peroxide | 17.1 | 131 ± 12 | 0.5 ± 0.0 | 37.4 ± 2.7 | 344 ± 10 | 85.2 ± 0.4 |
| 0.1 wt % Vitamin E | | | | | | |
| 0.5 wt % peroxide | 8.4 | 126 ± 2 | 1.7 ± 0.2 | 46.1 ± 0.9 | 393 ± 10 | 97.1 ± 0.3 |
| 0.7 wt % peroxide | 12.0 | 110 ± 4 | 0.7 ± 0.1 | 39.2 ± 2.3 | 357 ± 8 | 90.0 ± 0.7 |

OIT denotes 'Oxidation Induction time';
CLD denotes 'Cross-link density';
UTS denotes 'Ultimate tensile strength' and
EAB denotes 'Elongation at break'.

TABLE 14-2

The physicochemical and tensile mechanical properties of 0.2 and 0.1 wt % Vitamin E-blended, peroxide cross-linked GUR 1020 UHMWPEs after further high temperature melting at 310° C.

| Sample | OIT (mins) | CLD (mol/m$^3$) | Wear (mg/MC) | UTS (MPa) | EAB (%) | Impact Strength (kJ/m$^2$) |
|---|---|---|---|---|---|---|
| 0.2 wt % Vitamin E | | | | | | |
| 0.7 wt % peroxide | 19.6 | 135 ± 4 | 2.4 ± 0.9 | 39.2 ± 3.0 | 409 ± 32 | 91.4 ± 2.1 |
| 0.9 wt % peroxide | 29.4 | 161 ± 2 | 1.5 ± 0.5 | 38.7 ± 1.3 | 367 ± 26 | 81.7 ± 2.6 |
| 0.1 wt % Vitamin E | | | | | | |
| 0.5 wt % peroxide | 18.4 | 107 ± 1 | 1.9 ± 0.3 | 48.4 ± 0.7 | 429 ± 8 | 100 ± 0.8 |
| 0.7 wt % peroxide | Not-tested | 149 ± 0 | 1.4 ± 0.4 | 40.0 ± 3.9 | 387 ± 8 | 87.9 ± 1. |

OIT denotes 'Oxidation Induction time';
CLD denotes 'Cross-link density';
UTS denotes 'Ultimate tensile strength' and
EAB denotes 'Elongation at break'.

Example 23. The Effect of Molding Conditions

Medical grade GUR1050 UHMWPE (Celanese, Tex., USA) was blended with 0.5 wt % vitamin E by first preparing a master batch of vitamin E/UHMWPE blend containing 2 wt % vitamin E with the aid of isopropyl alcohol (IPA) as described above in Example 9. Then, the master blend was diluted to the desired concentration by mixing with virgin GUR 1050 UHMWPE.

An approximately 100 g batch of 0.5 wt % vitamin E-blended UHMWPE was prepared by mixing the 2 wt % vitamin E master batch with the virgin GUR 1050 UHMWPE, which was then mixed with P130 in the amount of 0.9 wt % peroxide.

The vitamin E and peroxide-blended UHMWPE batch was compression molded on a laboratory press at (i) 190° C. for 2 hours and cooled under pressure to below its melting point, or (ii) 160° C. for 90 minutes followed by 190° C. for 30 minutes resulting in cylindrical pucks with an approximate diameter of 10.5 cm and a thickness of 1 cm.

The resulting pucks were either tested 'as is' or further treated by high temperature melting at 310° C. for 5 hours and then cooling in nitrogen in a convection oven.

Samples were tested to determine oxidation induction time, crosslink density, POD wear rate, tensile mechanical properties, and IZOD impact strength using methods described in Example 11, 12, 13, 14, and 15.

TABLE 15-1

The physicochemical and tensile mechanical properties of 0.8 wt %
vitamin E-blended and 1 wt % peroxide-blended UHMWPEs before
and after further high temperature melting.

| Sample Molding Conditions | OIT (mins) | CLD (mol/m$^3$) | Wear (mg/MC) | UTS (MPa) | EAB (%) | Impact Strength (kJ/m$^2$) |
|---|---|---|---|---|---|---|
| 190° C. for 2 hours | 27.1 | 124 ± 3 | 1.4 ± 0.2 | 39.3 ± 2.2 | 420 ± 9 | 99.7 ± 0.7 |
| 160° C. for 90 min + 190° C. for 30 min | 36.8 | 159 ± 4 | 1.4 ± 0.3 | 50.0 ± 2.8 | 374 ± 9 | 91.8 ± 0.2 |

OIT denotes 'Oxidation Induction time';
CLD denotes 'Cross-link density';
UTS denotes 'Ultimate tensile strength' and
EAB denotes 'Elongation at break'.

The ultimate tensile strength of 0.5 wt % vitamin E-blended, 0.9 wt % peroxide cross-linked GUR1050 UHMWPE was improved by changing the molding conditions (Table 8-1). This was likely the result of improved consolidation achieved when the molding was first performed at the lower temperature (160° C.). The fusing together (or sintering or consolidation) of resin flakes become less efficient with increasing levels of crosslinking. Therefore it is desirable to have consolidation to occur before substantial cross-linking would inhibit further consolidation. The consolidation and the cross-linking will always be in competition during molding of the polymeric material containing cross-linking agent among other additives. One can use lower temperatures to increase rate of consolidation and slow down the rate of cross-linking during molding. When the consolidation was carried out at the higher temperature (190° C.) the crosslinking was likely occurring faster in comparison with the rate of cross-linking in the two-step molding (160° C./190° C.) process; hence the former resulted in lower strength, which is typical of poorly consolidated polymeric material. Ram extrusion is a large-scale consolidation process, where the polymeric material with or without additives is pushed through a heated barrel. Typically the polymeric material consolidates as it travels through the barrel and comes out from the other end of the barrel in a molten state and solidifies under atmospheric pressure. When the cross-linking agent additive is present, it is preferable to have the barrel temperature to be lower at first to ensure good consolidation before substantial cross-linking takes place. The barrel typically has multiple heating zones. The additional heating zones can be used to vary the temperature along the length of the barrel, such that higher temperatures are present after desired level of consolidation takes place as the polymeric material travels through the barrel. In the higher temperature zones of the barrel desired cross-linking level can then be achieved. It is also desirable to actively cool down the barrel near where the polymeric material with the cross-linking agent is delivered into the barrel through a hopper to avoid any premature high rate of cross-linking before consolidation starts.

Example 24. Scale-Up Compression Molded Blocks of Vitamin E and Peroxide-Blended, Cross-Linked UHMWPE GUR 1020 or GUR1050 UHMWPE was blended on a large scale (approximately 55 lbs of powder resin) with vitamin E and P130.

Approximately 600 grams of each blend was placed in a rectangular mold (approximately 6.1 inches×3.25 inches× 2.1 inches) and compression molded using two temperature regimes. In the first, the temperature of the platen were kept at 160° C. for 2 hours, then raised to and kept at 190° C. for 4 hours under pressure. In the second, the platens were kept at 190° C. for 6 hours under pressure.

After compression molding, the blocks were cut in half. One half was tested as is and the other half was treated using high temperature melting. High temperature melting was performed in nitrogen in a convection oven at 310° C. for 10 hours followed by cooling under nitrogen.

Samples were tested to determine oxidation induction time, crosslink density, POD wear rate, tensile mechanical properties, and IZOD impact strength using methods described in Example 11, 12, 13, 14, and 15.

TABLE 16-1

The physicochemical and tensile mechanical properties of 0.2 wt %
vitamin E-blended and 0.7 wt % peroxide-blended GUR1020
UHMWPEs before and after further high temperature melting.

| Sample Processing Conditions | OIT (mins) | CLD (mol/m$^3$) | Wear (mg/MC) | UTS (MPa) | EAB (%) | Impact Strength (kJ/m$^2$) |
|---|---|---|---|---|---|---|
| 190° C.-6 hrs No HTM | 18.7 | 207 ± 5 | Not-tested | 48.9 ± 2.9 | 230 ± 4 | 70.5 ± 5.6 |
| 190° C.-6 hrs + HTM 310° C. 10 hrs | 28.6 | 93 ± 3 | 2.9 ± 0.3 | 50.1 ± 2.3 | 420 ± 16 | 83.5 ± 4.9 |
| 160° C./190° C. No HTM | 16.0 | 232 ± 5 | Not-tested | 45.1 ± 2.4 | 321 ± 8 | 76.9 ± 3.0 |

TABLE 16-1-continued

The physicochemical and tensile mechanical properties of 0.2 wt % vitamin E-blended and 0.7 wt % peroxide-blended GUR1020 UHMWPEs before and after further high temperature melting.

| Sample Processing Conditions | OIT (mins) | CLD (mol/m$^3$) | Wear (mg/MC) | UTS (MPa) | EAB (%) | Impact Strength (kJ/m$^2$) |
|---|---|---|---|---|---|---|
| 160° C./190° C. + HTM 310° C. 10 hrs | 35.3 | 106 ± 7 | 3.0 ± 0.5 | 50.1 ± 7.1 | 430 ± 26 | 98.3 ± 5.6 |

OIT denotes 'Oxidation Induction time';
CLD denotes 'Cross-link density';
UTS denotes 'Ultimate tensile strength' and
EAB denotes 'Elongation at break'.

TABLE 16-2

The physicochemical and tensile mechanical properties of 0.2 wt % vitamin E-blended and 0.9 wt % peroxide-blended GUR1020 UHMWPEs before and after further high temperature melting.

| Sample Processing Conditions | OIT (mins) | CLD (mol/m$^3$) | Wear (mg/MC) | UTS (MPa) | EAB (%) | Impact Strength (kJ/m$^2$) |
|---|---|---|---|---|---|---|
| 190° C.-6 hrs | 18.2 | 242 ± 26 | Not-tested | 31.7 ± 1.4 | 268 ± 8 | 63.1 ± 1.4 |
| 190° C.-6 hrs + HTM 310° C. 10 hrs | 29.1 | 161 ± 3 | Not-tested | 36.2 ± 2.5 | 347 ± 10 | 80.8 ± 2.7 |
| 160° C./190° C. | 13.8 | 314 ± 22 | Not-tested | 28.1 ± 3.1 | 251 ± 7 | 71.6 ± 1.4 |
| 160° C./190° C. + HTM 310° C. 10 hrs | 26.9 | 186 ± 20 | 0.7 ± 0.1 | 40.6 ± 4.6 | 370 ± 9 | 80.6 ± 0.8 |

OIT denotes 'Oxidation Induction time';
CLD denotes 'Cross-link density';
UTS denotes 'Ultimate tensile strength' and
EAB denotes 'Elongation at break'.

TABLE 16-3

The physicochemical and tensile mechanical properties of 0.2 wt % vitamin E-blended and peroxide-blended GUR1050 UHMWPEs before and after further high temperature melting.

| Peroxide Concentration (wt %) and Processing Conditions | OIT (mins) | CLD (mol/m$^3$) | Wear (mg/MC) | UTS (MPa) | EAB (%) | Impact Strength (kJ/m$^2$) |
|---|---|---|---|---|---|---|
| 0.6 wt % peroxide | Not-tested | Not-tested | Not-tested | 47.1 ± 4.5 | 261 ± 8 | 69.8 ± 1.8 |
| 0.6 wt % peroxide + HTM 310° C. 10 hrs | Not-tested | 128 ± 4 | Not-tested | 40.1 ± 3.4 | 386 ± 17 | 90.1 ± 4.2 |
| 0.8 wt % peroxide | Not-tested | 326 ± 13 | Not-tested | 46.4 ± 3.4 | 216 ± 3 | 62.0 ± 1.3 |
| 0.8 wt % peroxide + HTM 310° C. for 10 hrs | Not-tested | 197 ± 5 | 1.3 ± 0.2 | 43.9 ± 2.5 | 276 ± 7 | 80.0 ± 2.9 |

OIT denotes 'Oxidation Induction time';
CLD denotes 'Cross-link density';
UTS denotes 'Ultimate tensile strength' and
EAB denotes 'Elongation at break'.
All compression molding was performed using 160° C. for 2 hours followed by 190° C. for 4 hours under pressure.

These results showed that large scale consolidation by compression molding was feasible. Comparison of the properties of the blocks before and after HTM showed that OIT, UTS, EAB and impact strength were increased by HTM and cross-link density was decreased as expected.

Example 25. Large Scale Ram Extrusion of Antioxidant and Peroxide-Containing UHMWPE Followed by High Temperature Melting GUR 1020 or GUR1050 UHMWPE was blended on a large scale (approximately 55 lbs of powder resin) with vitamin E and P130.

TABLE 17-1

The resin type, vitamin E concentration and P130 concentration used in the ram extrusion of 2.75" diameter bars of UHMWPE.

| GUR UHMWPE Type | Vitamin Concentration (wt %) | P130 Concentration (wt %) |
|---|---|---|
| 1020 | 0.2 | 0.7 |
| 1020 | 0.2 | 0.9 |
| 1050 | 0.2 | 0.6 |
| 1050 | 0.2 | 0.8 |

The vitamin E and peroxide blends of UHMWPE were ram extruded into 2.75" diameter cylindrical bars, then cut into 10" length for further processing.

High temperature melting of 10"-long pieces of extruded bars were performed in a nitrogen convection oven. During high temperature melting the bars were placed and kept at the desired temperature for the desired amount of time, then were cooled down to 40° C. at roughly 2.5° C./min.

Samples were tested to determine oxidation induction time, crosslink density, POD wear rate, tensile mechanical properties, and IZOD impact strength using methods described in Example 11, 12, 13, 14, and 15.

TABLE 17-2

The physicochemical and tensile mechanical properties of 0.2 wt % vitamin E-blended and peroxide-blended GUR1020 and GUR 1050 UHMWPEs after further high temperature melting.

| Peroxide Concentration (wt %) | UHMWPE GUR Type | OIT (mins) | CLD (mol/m³) | Wear (mg/MC) | UTS (MPa) | EAB (%) | Impact Strength (kJ/m²) |
|---|---|---|---|---|---|---|---|
| 0.9 | 1020 | 27.5 | 179 ± 7 | 1.3 ± 0.2 | 41.5 ± 2.7 | 306 ± 12 | 76.6 ± 2.9 |
| 0.6 | 1050 | 27.9 | 120 ± 7 | 3.4 ± 0.2 | 51.1 ± 2.5 | 386 ± 14 | 98.9 ± 3.8 |
| 0.8 | 1050 | 32.0 | 156 ± 6 | 1.8 ± 0.2 | 45.4 ± 3.7 | 321 ± 12 | 81.2 ± 2.5 |

OIT denotes 'Oxidation Induction time';
CLD denotes 'Cross-link density';
UTS denotes 'Ultimate tensile strength' and
EAB denotes 'Elongation at break'.
All samples were ram extruded and high temperature melting was performed at 310° C. for 12 hours.

TABLE 17-3

The physicochemical and tensile mechanical properties of 0.2 wt % vitamin E-blended and 0.8 wt % peroxide-blended GUR 1050 UHMWPEs after further high temperature melting.

| HTM Temperature (° C.) | HTM Time (hrs) | OIT (mins) | CLD (mol/m³) | Wear (mg/MC) | UTS (MPa) | EAB (%) | Impact Strength (kJ/m²) |
|---|---|---|---|---|---|---|---|
| 310 | 8 | 36.2 | 176 ± 8 | 1.1 ± 0.2 | 46.4 ± 3.7 | 307 ± 13 | 78.8 ± 3.6 |
| 315 | 8 | 38.5 | 164 ± 6 | 1.5 ± 0.1 | 44.3 ± 3.1 | 323 ± 10 | 84.2 ± 0.7 |
| 320 | 6 | 31.4 | 190 ± 44 | 1.2 ± 0.2 | 49.6 ± 1.9 | 323 ± 13 | 83.8 ± 2.4 |

OIT denotes 'Oxidation Induction time';
CLD denotes 'Cross-link density';
UTS denotes 'Ultimate tensile strength' and
EAB denotes 'Elongation at break'.
All samples were ram extruded.

These results showed that 2.75" diameter bars could be extruded on the large scale with antioxidant and peroxide blends which led to the cross-linking of the bars. In addition, high temperature melting of said bars after extrusion resulted in uniform properties, good wear resistance, high elongation at break and high impact strength. Increasing peroxide concentration decreased impact strength and wear, but these properties could also be manipulated by changing HTM time and temperature.

Example 26. Peroxide Cross-Linking and High Temperature Melting with a Peroxide Decomposing at Higher than Consolidation Temperature Medical grade GUR1050 UHMWPE (Celanese, Tex., USA) was blended with 0.2 wt % vitamin E (D,L-alpha-tocopherol) by first preparing a master batch of vitamin E/UHMWPE blend containing 2 wt % vitamin E with the aid of isopropyl alcohol (IPA) as described above in Example 9. Then, the master blend was diluted to the desired concentration by mixing with virgin GUR 1050 UHMWPE.

An approximately 100 g batch of 0.2 wt % vitamin E-blended GUR 1050 UHMWPE was prepared by mixing the 2 wt % vitamin E/GUR 1050 UHMWPE master batch with the virgin GUR 1050 UHMWPE, which was then mixed with peroxide (3,3,5,7,7-pentamethyl-1,2,4-trioxepane, also called Trigonox 311, peroxide 311 or T311) in the amount of 0.8 wt % peroxide.

The vitamin E and peroxide-blended UHMWPE batches were compression molded on a laboratory press (i) at 180° C. for 5 minutes, then cooled under pressure to below its melting point or (ii) at 210° C. for 2 hours and cooled under pressure to below its melting point, resulting in a cylindrical puck with an approximate diameter of 10.5 cm and a thickness of 1 cm.

The resulting pucks were either tested 'as is' or further treated by high temperature melting at 310° C. for 5 hours and then cooling in nitrogen in a convection oven.

Samples were tested to determine oxidation induction time, crosslink density, POD wear rate, tensile mechanical properties, and IZOD impact strength using methods described in Example 11, 12, 13, 14, and 15.

TABLE 18-1

The physicochemical and tensile mechanical properties of 0.2 wt % vitamin E-blended and 0.8 wt % T311-blended GUR1050 UHMWPEs before and after further high temperature melting.

| Sample | OIT (mins) | CLD (mol/m$^3$) | Wear (mg/MC) | UTS (MPa) | EAB (%) | Impact Strength (kJ/m$^2$) |
|---|---|---|---|---|---|---|
| Molded at 180° C. for 5 minutes | Not-tested | 0 ± 0 | Not-tested | Not-tested | Not-tested | Not-tested |
| Molded at 180° C. for 5 minutes + HTM 310° C. for 5 hours | Not-tested | 41 ± 2 | Not-tested | 44.0 ± 4.2 | 524 ± 28 | 117 ± 3.9 |
| Molded at 210° C. for 2 hours | Not-tested | 162 ± 2 | Not-tested | Not-tested | Not-tested | Not-tested |
| Molded at 210° C. for 2 hours + HTM at 310° C. for 5 hours | Not-tested | 31 ± 8 | 8.8 ± 2.8 | 43.2 ± 1.5 | 599 ± 17 | 126 ± 3.1 |

OIT denotes 'Oxidation Induction time';
CLD denotes 'Cross-link density';
UTS denotes 'Ultimate tensile strength' and
EAB denotes 'Elongation at break'.

The 1 hour decomposition temperature of Trigonox 311 used here is reported as 184° C., which is also reported as $T_1$, indicating that half of the available peroxide will have decomposed in 1 hour at this temperature. The results showed that UHMWPE could be molded in the presence of this peroxide without appreciable cross-linking below this temperature, at 180° C. When the molding temperature was raised to 210° C. above the 1 hour decomposition temperature, there was substantial cross-linking.

In certain embodiments the Trigonox 311 can be mixed with another peroxide that decomposes at a lower temperature, for instance P130. The mixture of P130 and Trigonox 311 at any concentration, for example half-and-half, can be added to the UHMWPE/antioxidant blend prior to consolidation. Some of the cross-linking will occur during consolidation and some of it can occur after consolidation during high temperature treatment.

Example 27. The Wear and Mechanical Properties of Peroxide Cross-Linked UHMWPEs Medical grade GUR1050 UHMWPE (Celanese, Tex., USA) was blended with 0.1, 0.2, 0.3, 0.5, 0.6, 0.8 Or 1 wt % vitamin E by first preparing a master batch of vitamin E/UHMWPE blend containing 2 wt % vitamin E with the aid of isopropyl alcohol (IPA) as described above in Example 9. Then, the master blend was diluted to the desired concentration by mixing with virgin (no additive) GUR 1050 UHMWPE.

An approximately 100 g batch of the vitamin E-blended UHMWPE was prepared by mixing the 2 wt % vitamin E/GUR 1050 UHMWPE master batch with the virgin GUR 1050 UHMWPE, which was then mixed with P130 in concentrations of 0.5, 1 or 1.5 wt % P130 peroxide.

The vitamin E and peroxide-blended UHMWPE batch was compression molded on a laboratory press at 190° C. for 2 hours and cooled under pressure to below its melting point, resulting in cylindrical pucks with an approximate diameter of 10.5 cm and a thickness of 1 cm.

Samples were tested to determine oxidation induction time, crosslink density, POD wear rate, and tensile mechanical properties using methods described in Example 11, 12, 13, and 14. For comparison, virgin GUR 1050 UHMWPE with no vitamin E was also blended with P130 at 0.5, 1, or 1.5 wt % P130. These blends were consolidated using the above described molding consolidations. In addition, virgin GUR 1050 and vitamin E/UHMWPE blends with 0.1, 0.2, 0.5 and 1 wt % vitamin E were consolidated and irradiated to 150 kGy at room temperature using electron beam irradiation.

Figure 8:
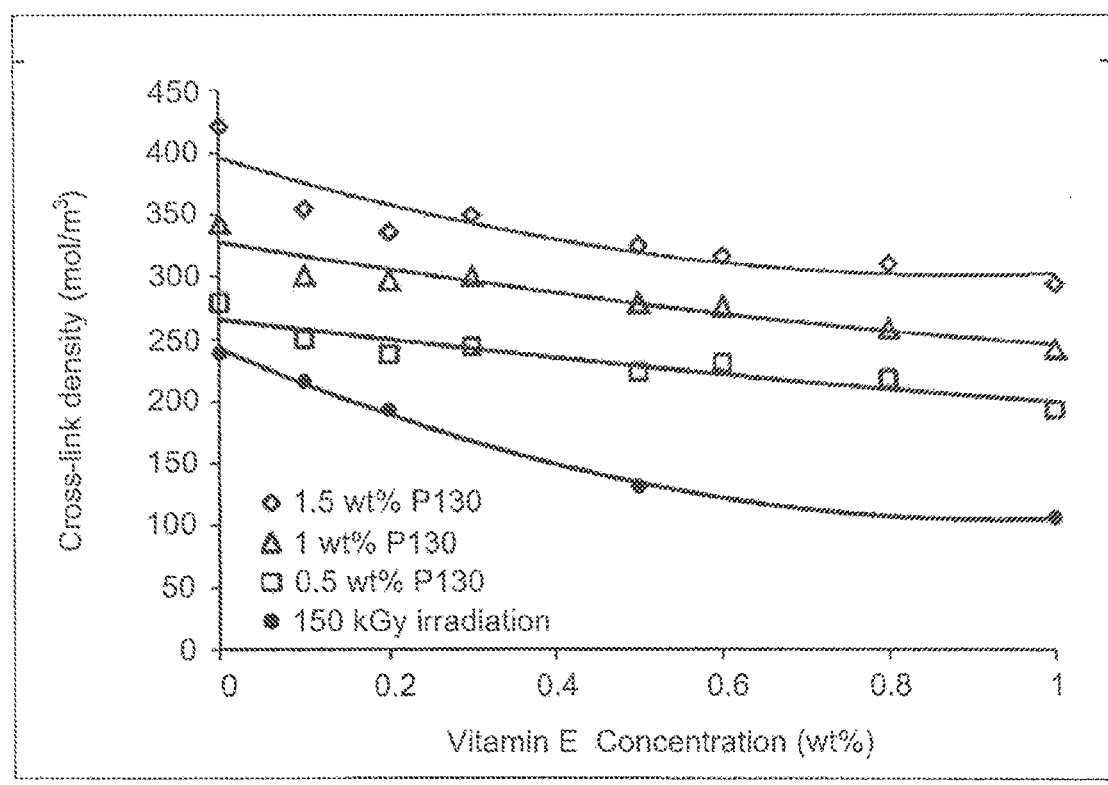
FIG. 8 shows the cross-link density of vitamin E-blended and P130 cross-linked UHMWPE compared to radiation cross-linked UHMWPE.
Figure 9:
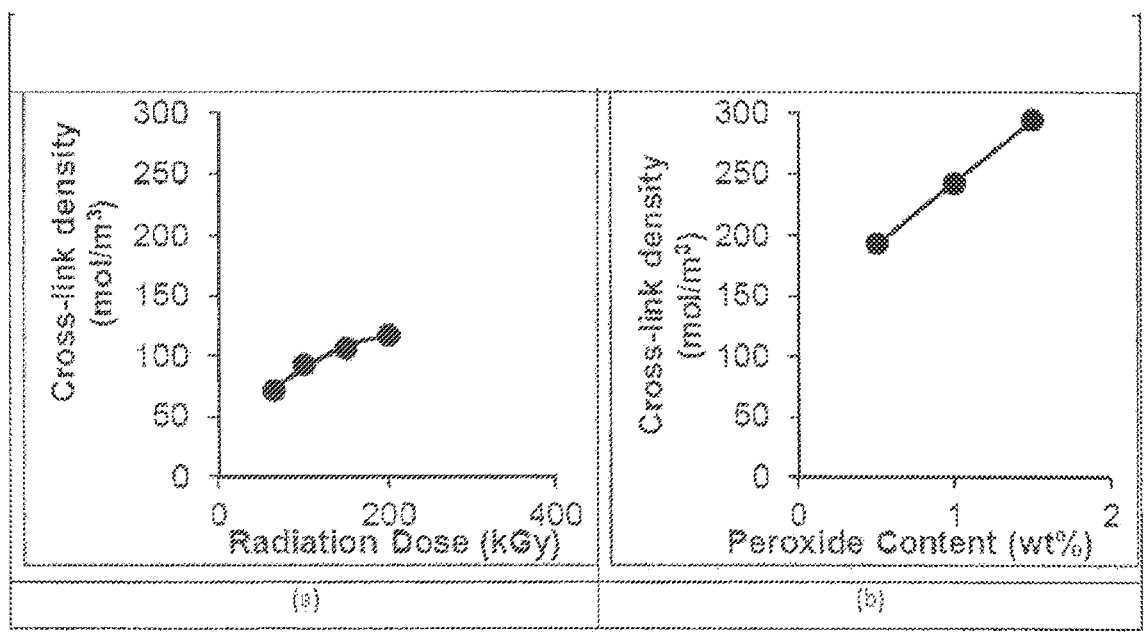
FIG. 9 shows the cross-link density as a function of (a) radiation dose and (b) peroxide content for radiation and peroxide cross-linked UHMWPEs respectively.

The cross-link density behavior of peroxide cross-linked UHMWPE as a function of increasing vitamin E concentration (FIG. 8) suggested that vitamin E interfered with cross-linking as a free radical scavenger. However, the effect of vitamin E in decreasing the cross-linking efficiency was weaker with peroxide cross-linking compared to that effect with radiation cross-linking (FIG. 8). In addition, at the high vitamin E concentration of 1 wt %, the cross-link density gains by increasing radiation dose were substantially diminished (FIG. 9a), whereas using peroxide cross-linking, it was possible to obtain high cross-link density (FIG. 9b).

TABLE 19-1

The oxidation induction time (OIT) of vitamin E-blended, peroxide cross-linked UHMWPEs as a function of vitamin E concentration and peroxide concentration.

| Vitamin E concentration | Peroxide concentration (wt. %) | | |
|---|---|---|---|
| | 0.5 | 1.0 | 1.5 |
| — | <1 | <1 | <1 |
| 0.1 | 9 | 4 | 8 |
| 0.2 | 12 | 13 | 14 |
| 0.3 | 16 | 17 | 16 |
| 0.5 | 30 | 19 | 21 |
| 0.6 | 38 | 20 | 23 |
| 0.8 | 47 | 27 | 25 |
| 1.0 | 57 | 36 | 29 |

The OIT of peroxide cross-linked UHMWPE was substantially higher than virgin (no antioxidant), peroxide cross-linked UHMWPE (Table 19-1).

Example 28. Animal Testing to Determine the Peri-Prosthetic Effect of Antioxidant-Containing Peroxide Cross-Linked UHMWPE Medical grade GUR1050 UHMWPE (Celanese, Tex., USA) was blended with 1 wt % vitamin E by first preparing a master batch of vitamin E/UHMWPE blend containing 2 wt % vitamin E with the aid of isopropyl alcohol (IPA) as described above in Example 9. Then, the master blend was diluted to the desired concentration by mixing with virgin GUR 1050 UHMWPE.

An approximately 100 g batch of 1 wt % vitamin E-blended UHMWPE was prepared by mixing the 2 wt % vitamin E/GUR 1050 UHMWPE master batch with the virgin GUR 1050 UHMWPE, which was then mixed with P130 in the amount of 2 wt % P130 peroxide.

The vitamin E and peroxide-blended UHMWPE batch was compression molded on a laboratory press at 190° C. for 2 hours and cooled under pressure to below its melting point, resulting in cylindrical pucks with an approximate diameter of 10.5 cm and a thickness of 1 cm.

The resulting pucks were either tested 'as is' or further heated to 180, 190 or 200° C. for 5 hours and cooled in a nitrogen convection oven. The pucks were machined into small cylindrical specimens (diameter=5 mm, thickness=2 mm) for further implantation in animals. Controls were machined from 1 wt % vitamin E blended UHMWPE consolidated as described above and used without further annealing.

Control samples had no added peroxide.

Animal implantation and assessment: Short term biological evaluation of the peroxide cross-linked UHMWPE was performed using subcutaneous implantation of these small cylindrical specimens in C57BL/6 mice (n-12). Two implants per group (vitamin E only, consolidated peroxide crosslinked and consolidated/annealed peroxide cross-linked) were implanted each in two mice per time point to be evaluated at 24 weeks, 1 week and 3 weeks of implantation.

At the end of implantation period, the animals were sacrificed and the tissue containing the implants was excised. Multiple sections (approximately every 100 microns) were obtained for histology, stained with Hematoxylin & Eosin and were analyzed by a blinded observer.

There was no observable difference between control samples containing only vitamin E compared to the consolidated and consolidated/annealed samples up to 3 weeks, suggesting that there was no acute inflammatory response specific to peroxide cross-linked UHMWPE in this model.

Example 29. The Effect of Some Consolidation Conditions on Peroxide Cross-Linked UHMWPE Medical grade GUR1020 UHMWPE (Celanese, Tex., USA) was blended with 0.8 wt % vitamin E by first preparing a master batch of vitamin E/UHMWPE blend containing 2 wt % vitamin E with the aid of isopropyl alcohol (IPA) as described above in Example 9. Then, the master blend was diluted to the desired concentration by mixing with virgin (no additive) GUR 1020 UHMWPE.

An approximately 100 g batch of the 0.8 wt % vitamin E-blended UHMWPE was prepared by mixing the 2 wt % vitamin E/1 GUR 1020 UHMWPE master batch with the virgin GUR 1020 UHMWPE, which was then mixed with P130 in the amount of 1 wt % P130 peroxide.

To determine the effect of molding temperature, the vitamin E and peroxide-blended UHMWPE batch was compression molded on a laboratory press at 190, 230, 245, 270 or 300° C. for 2 hours and cooled under pressure to below its melting point, resulting in cylindrical pucks with an approximate diameter of 10.5 cm and a thickness of 1 cm.

To determine the effect of molding duration, the vitamin E and peroxide-blended UHMWPE batch was compression molded on a laboratory press at 190° C. for 2 hours, 1 hour, 30 minutes or 15 minutes and cooled under pressure to below its melting point, resulting in cylindrical pucks with an approximate diameter of 10.5 cm and a thickness of 1 cm.

Samples were tested to determine crosslink density using methods described in Example 12.

TABLE 21-1

The effect of molding temperature for vitamin E containing, peroxide cross-linked UHMWPE. Molding was performed for 2 hours.

| Molding temperature (° C.) | Cross-link density (mol/m$^3$) |
|---|---|
| 190 | 212 ± 6 |
| 230 | 208 ± 3 |
| 245 | 191 ± 6 |
| 270 | 186 ± 1 |
| 300 | 170 ± 6 |

The cross-link density of vitamin E containing, P130 cross-linked UHMWPE samples was decreased with increasing molding temperature (Table 21-1). This suggested that the temperature of consolidation is an important factor in determining cross-link density.

TABLE 21-2

The effect of molding duration for vitamin E containing, peroxide cross-linked UHMWPE.

| Molding duration (min) | Cross-link density (mol/m$^3$) |
|---|---|
| 120 | 206 ± 4 |
| 60 | 206 ± 0 |
| 30 | 199 ± 3 |

The cross-link density of vitamin E containing, P130 cross-linked UHMWPE samples was not changed when the consolidation duration was decreased from 2 hours to 30 minutes for 1 cm-thickness of consolidated sample (Table 21-2).

Example 30. Effect of Gamma Irradiation on Peroxide Cross-Linked UHMWPE

Medical grade GUR1050 UHMWPE (Celanese, Tex., USA) was blended with 0.3, 0.5, 0.6, 0.8 or 1 wt % vitamin E by diluting the 2 wt % vitamin E/GUR 1050 UHMWPE master batch of Example 9 with the addition of virgin GUR 1050 UHMWPE.

An approximately 100 g batch of each vitamin E/GUR 1050 UHMWPE blend was mixed with P130 in the amount of 0.5 or 1 wt % peroxide.

The vitamin E and peroxide-blended UHMWPE blends were compression molded on a laboratory press at 190° C. for 2 hours and cooled under pressure to below its melting point, resulting in cylindrical pucks with an approximate diameter of 10.5 cm and a thickness of 1 cm.

The peroxide cross-linked pucks (n=1 each) were vacuum packaged and subsequently subjected the gamma irradiation with an approximate radiation dose of 25 kGy. The properties were tested 'as is' or after gamma sterilization.

Samples were tested to determine oxidation induction time, crosslink density, POD wear rate, and tensile mechanical properties using methods described in Example 11, 12, 13 and 14.

TABLE 22-1

Cross-link density as a function of the vitamin E content for peroxide cross-linked VE/UHMWPE blends pre and post gamma sterilization.

| Vitamin E Concentration (wt %) | Cross-link Density before sterilization (mol/m³) | | Cross-link Density after sterilization (mol/m³) | |
|---|---|---|---|---|
| | 0.5 wt % P130 | 1 wt % P130 | 0.5 wt % P130 | 1 wt % P130 |
| 0.3 | 249 ± 7 | 296 ± 8 | 237 ± 5 | 288 ± 10 |
| 0.5 | 230 ± 6 | 297 ± 12 | 210 ± 4 | 276 ± 5 |
| 0.6 | 231 ± 4 | 284 ± 5 | 208 ± 5 | 270 ± 4 |
| 0.8 | 218 ± 6 | 279 ± 10 | 192 ± 4 | 255 ± 3 |
| 1 | 207 ± 7 | 274 ± 5 | 178 ± 4 | 241 ± 3 |

Figure 10:
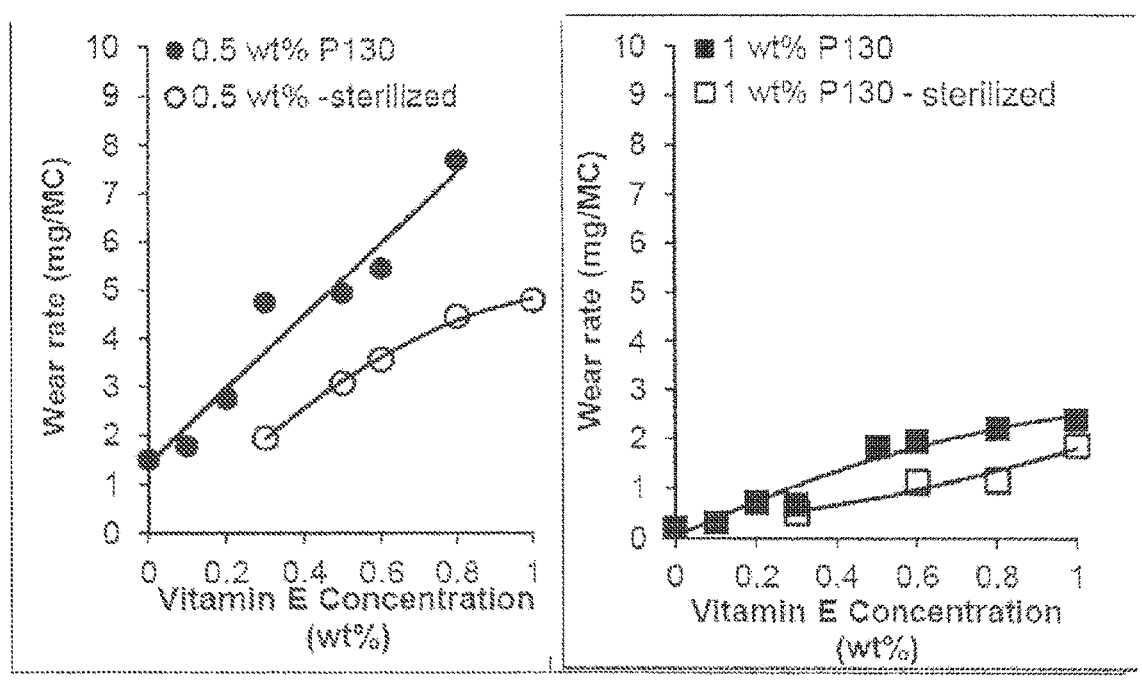
FIG. 10 shows the wear rates as a function of the vitamin E content for peroxide cross-linked, vitamin E-blended UHMWPE pre and post gamma irradiation (25 kGy).

The cross-link density of peroxide cross-linked, vitamin E-blended UHMWPE decreased after gamma irradiation (Table 22-1). Also the wear rates were decreased as a result of gamma irradiation (FIG. 10). These results suggested that peroxide cross-linking and radiation cross-linking of UHMWPE can be used in conjunction.

TABLE 22-2

Oxidation induction time (OIT) as a function of the vitamin E content for peroxide cross-linked VE/UHMWPE blends pre and post gamma sterilization.

| Vitamin E concentration (wt %) | OIT before sterilization (minutes) | | OIT after sterilization (minutes) | |
|---|---|---|---|---|
| | 0.5 wt % P130 | 1 wt % P130 | 0.5 wt % P130 | 1 wt % P130 |
| 0.3 | 16 | 17 | 13 | 14 |
| 0.5 | 30 | 19 | 18 | 22 |
| 0.6 | 38 | 20 | 22 | 20 |
| 0.8 | 47 | 27 | 38 | 25 |
| 1 | 57 | 36 | 53 | 33 |

The oxidation induction time of peroxide cross-linked, vitamin E-blended UHMWPE was decreased slightly after gamma irradiation, but the OIT values were still very high after gamma irradiation, suggesting that irradiated, peroxide cross-linked UHMWPEs were oxidatively stable in the presence of the antioxidant vitamin E.

Example 31. Prevention of Defect Formation During High Temperature Melting by Cross-Linking Vitamin E blended UHMWPE (0.1 wt %) was obtained as bar stock from Orthoplastics Inc. (Lancashire, UK). Blocks were cut (10×6×6 cm) from the bar stock and gamma-irradiated to 25, 50 or 75 kGy (n=5 each). All blocks and a set of control unirradiated blocks were then high temperature melted in a pre-heated nitrogen convection oven at 320° C. for 6 hours and cooled to about room temperature at about 2.5° C./min. After high temperature melting, the blocks were cut in half through the 10 cm length and visually observed for defects. The defect probability was calculated as the percentage of defects observed for each irradiation dose.

Samples were tested to determine tensile mechanical properties and IZOD impact strength using methods described in Examples 14 and 15.

The defect probability was 0% for 25, 50 and 75 kGy irradiated blocks after high temperature melting compared to 80% for unirradiated UHMWPE. The elongation at break and impact strength of these UHMWPEs were very high due to the high temperature melting (Table 23-1), suggesting they could be further cross-linked without significant loss of mechanical strength and toughness.

TABLE 23-1

Mechanical properties of irradiated and HTMed vitamin E blended UHMWPEs. High temperature melting was performed at 320° C. for 6 hours.

| Sample | UTS (MPa) | YS (MPa) | EAB (%) | Impact Strength (kJ/m²) |
|---|---|---|---|---|
| 25 kGy | 50.2 ± 0.9 | 23.2 ± 0.9 | 765 ± 10 | 99.4 ± 2.6 |
| 50 kGy | 53.8 ± 2.3 | 23.5 ± 0.3 | 700 ± 7 | 90.8 ± 2.8 |
| 75 kGy | 51.0 ± 1.8 | 22.3 ± 1.4 | 508 ± 39 | 99.0 ± 1.6 |

Example 32. Large Scale High Temperature Melting

GUR1050 UHMWPE was blended on a large scale (approximately 55 lbs of powder resin) with 0.2 wt % vitamin E and 0.765 wt % P130. This vitamin E and peroxide blend of UHMWPE was ram extruded into 4" diameter cylindrical bars, then cut into 4 cm length for further processing.

High temperature melting of 4 cm-thick samples (shaped as "hockey pucks") of extruded bars were performed in a nitrogen convection oven. The pucks were placed and were subjected to a heating program as designated below (Table 24-1). After these steps, the oven was cooled to 40° C. in 2 hours and samples were maintained in the oven for 4 hours. Each sample was subjected to either one or multiple steps of heating/soaking with a cooling cycle at the end.

TABLE 24-1

The sequence of heating/soaking steps and durations for each step.

| | Step 1 | Step 2 | Step 3 |
|---|---|---|---|
| Sample 1 | 250° C./10 hrs | | |
| Sample 2 | 250° C./7 hrs | 300° C./12 hrs | |
| Sample 3 | 250° C./4 hrs | 300° C./12 hrs | 250° C./5 hrs |

Samples were tested to determine POD wear rate, tensile mechanical properties, and IZOD impact strength using methods described in Example 11, 12, 13, 14, and 15.

TABLE 24-2

The mechanical strength, impact toughness and wear rates of peroxide cross-linked, vitamin E-blended, ram extruded UHMWPE before and after HTM using different heating cycles.

| | UTS (MPa) | EAB (%) | Impact Strength (kJ/m²) | Wear rate (mg/MC) |
|---|---|---|---|---|
| Pre-HTM | 46.9 ± 2.0 | 239 ± 6 | 63.6 ± 1.1 | 0.8 ± 0.1 |
| Sample 1 | 48.6 ± 3.5 | 263 ± 12 | 70.3 ± 1.3 | — |

TABLE 24-2-continued

The mechanical strength, impact toughness and wear rates of peroxide cross-linked, vitamin E-blended, ram extruded UHMWPE before and after HTM using different heating cycles.

|  | UTS (MPa) | EAB (%) | Impact Strength (kJ/m$^2$) | Wear rate (mg/MC) |
|---|---|---|---|---|
| Sample 2 | 52.9 ± 1.4 | 298 ± 5 | 78.7 ± 2.2 | 1.3 ± 0.4 |
| Sample 3 | 49.8 ± 2.3 | 292 ± 11 | 79.7 ± 2.2 | 1.1 ± 0.1 |

All UHMWPEs, which were high temperature melted, had higher UTS, EAB, impact strength and wear rates than the control ram extruded bar (Table 24-2). These results suggested that high temperature melting (HTM) improved the mechanical strength, elongation and impact toughness after ram extrusion.

Example 33. Removal of High Temperature Melting by-Products

GUR1050 UHMWPE was blended on a large scale (approximately 55 lbs of powder resin) with 0.2 wt % vitamin E and 0.875 wt % P130. This vitamin E and peroxide blend of UHMWPE was ram extruded into 4" diameter cylindrical bars, then cut into 4, 5, or 10 cm length for further processing by high temperature melting and/or extraction.

High temperature melting of different length extruded samples were performed in a nitrogen convection oven, whereby the samples were placed in a nitrogen convection oven and were subjected to a heating program. The heating program started out by slow heating to 250° C. followed by at least one long duration soak at 250° C. followed by slow heat to either 280 or 300° C. followed by a long duration soak (12 hrs) at either 280 or 300° C. After these steps, the oven was cooled to 40° C. in roughly 10 hours.

Thin sections (150 um) were cut using a manual microtome. The thin sections were scanned using an FTIR microscope. The scans were performed every 1 mm from a wavenumber of 400 to 4000 cm$^{-1}$ at an average of 32 scans. The amount of HTM byproducts was determined by normalizing the area under the absorbance at 1215 cm$^{-1}$ (1188-1222 cm$^{-1}$) against the absorbance at 1895 cm$^{-1}$ (1850-1985 cm$^{-1}$) after subtracting the respective baselines as is customary in the art.

Figure 11:
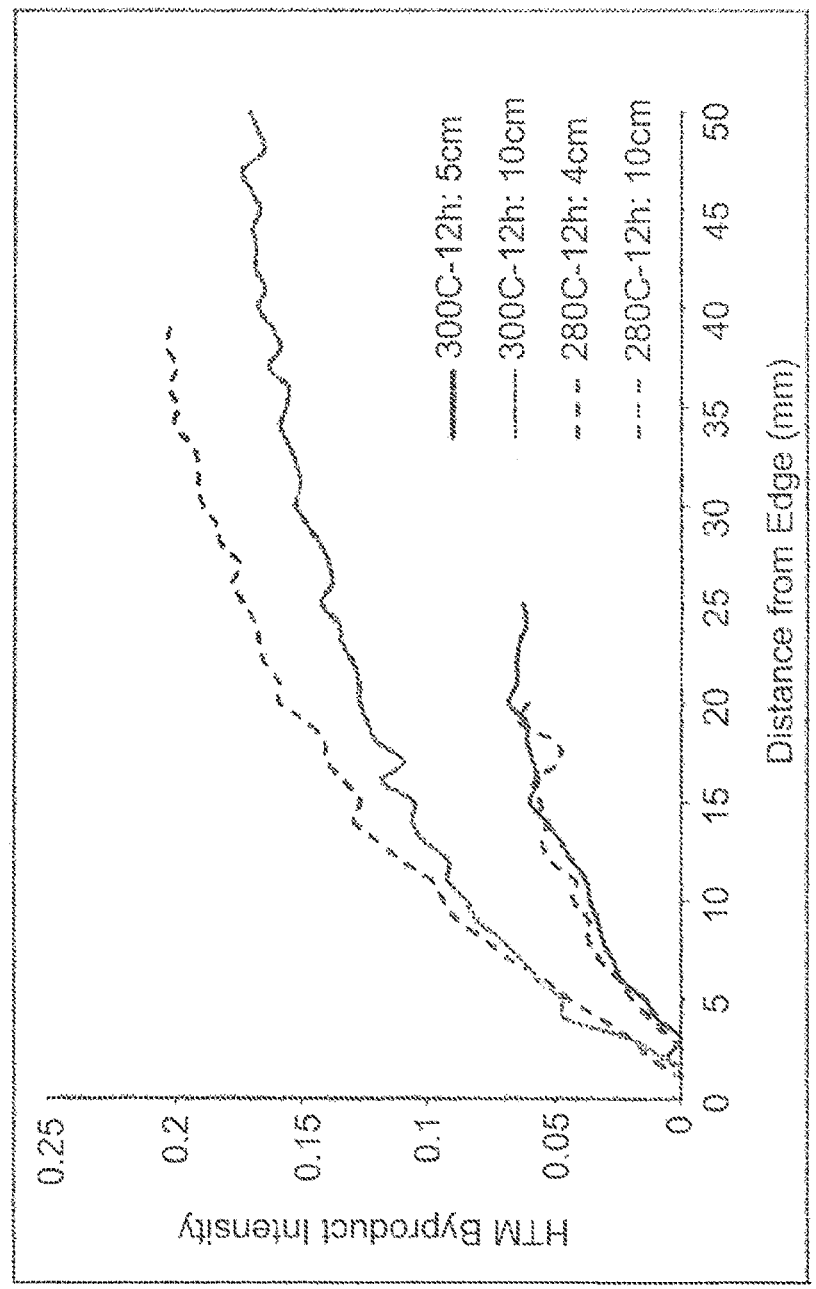
FIG. 11 shows the high temperature melting (HTM) by-product index as a function of depth into the UHMWPE for blocks of different thickness.

There were some byproduct detected by the FT IR. These byproducts or residuals were associated with the high temperature melting of peroxide cross-linked UHMWPE using P130. These residuals were quantified by calculating an HTM by-product index and measuring it across blocks of different thickness that underwent the HTM process as seen in FIG. 11.

The residuals were reduced greatly by using thinner blocks during HTM, presumably due to the more efficient diffusion of the residuals out of the blocks. Also, increasing HTM temperature from 280° C. to 300° C. decreased the residuals for 10 cm$^{-1}$ thick samples (FIG. 11). It is recommended to increase the temperature and/or duration during high temperature melting to minimize the concentration of the byproduct(s). However if the byproducts are tolerable by the patient then their removal from the polymeric material may not be necessary.

Example 34. Some Annealing Procedures to Reduce by-Products from Consolidation and High Temperature Melting GUR1050 UHMWPE was blended on a large scale (approximately 55 lbs of powder resin) with 0.2 wt % vitamin E and 0.875 wt % P130.

This vitamin E and peroxide blend of UHMWPE was ram extruded into 4" diameter cylindrical bars. High temperature melting (HTM) of the extruded bar (cut into roughly 25 cm-long sections) was performed in a nitrogen convection oven, whereby the bar was placed in a nitrogen convection oven and was subjected to a heating program which included a long duration soak at 320° C. for 7 hours. After this long duration soak, the oven was cooled to 40° C. in roughly 3 hours.

Thin sections (150 um) were cut using a manual microtome which were scanned using a FTIR. The scans were performed every 1 mm from a wave number of 400 to 4000 cm$^{-1}$ as an average of 32 scans. The amount of HTM by products was determined by normalizing the area under the absorbance at 1215 cm$^{-1}$ (1188-1222 cm$^{-1}$) against the absorbance at 1895 cm$^{-1}$ (1850-1985 cm$^{-1}$) after subtracting the respective baselines. The control sample before annealing was analyzed in the radial direction (10 cm) from the edge of the thin film that corresponded to the outside surface of the ram extruded rod to the center of the rod.

The roughly 25 cm bar that was processed by HTM was cut into 3 and 5 cm-thick sections and were placed in a convection oven in air at 130° C. One 3 cm-thick section was taken out at 5 days (~120 hours) and one 5 cm-thick section was taken out at 3 weeks (~504 hours). Thin sections (150 μm) were cut in the transverse direction for these 3 and 5 cm-thick samples. The FTIR analysis was performed as described above on thin films by scanning from the edge of the film that corresponded to the center of the cut surface of the ram extruded rod to the other edge of the film in the transverse direction (perpendicular to the radial direction).

Figure 12:
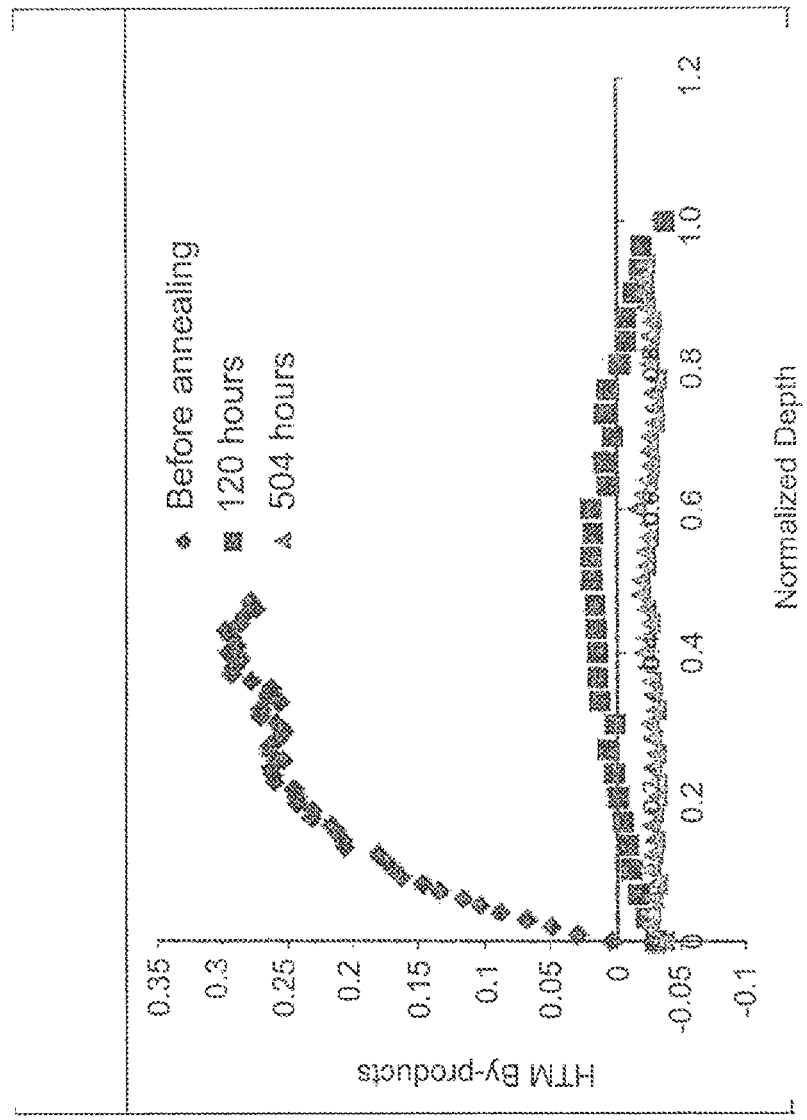
FIG. 12 shows the HTM by-products detected as a function of depth in ram extruded, vitamin E-blended, peroxide cross-linked UHMWPE before and after annealing at 130° C. in air for 120 hours or 504 hours.

There was an HTM byproduct infrared absorbance after HTM, which decreased after annealing at 130° C. (FIG. 12). After 3 weeks, there were no detectable peaks of the HTM byproducts.

After 3 weeks, the ultimate tensile strength was 48.1 MPa, the elongation-at-break was 301% and the IZOD impact strength was 78.4 kJ/m$^2$.

Example 35. Annealing of Vitamin E-Blended, Peroxide Crosslinked, High Temperature Melted UHMWPE in Water GUR1050 UHMWPE was blended on a large scale (approximately 55 lbs of powder resin) with 0.2 wt % vitamin E and 0.775 wt % P130. This vitamin E and peroxide blend of UHMWPE was ram extruded into 4" diameter cylindrical bars.

High temperature melting (HTM) of the extruded bar was performed in a nitrogen convection oven, the bar was placed in a nitrogen convection oven and was subjected to a heating program which included a long duration soak at 320° C. for 7 hours. After these steps, the oven was cooled to 40° C. in roughly 3 hours.

Thin sections (150 μm) were cut using a manual microtome. The thin sections were scanned using a FTIR. The amount of HTM by products was determined by normalizing the absorbance at 1215 cm$^{-1}$ (1188-1222 cm$^{-1}$) against the absorbance at 1895 cm$^{-1}$ (1850-1985 cm$^{-1}$) after subtracting the respective baselines.

The roughly 25 cm bar that was processed by HTM was cut into 1.8 cm$^{-1}$ thick sections and were placed in a convection oven in air or in water at 80° C. Sections were taken out at 18 hours and analyzed as described above.

Figure 13:
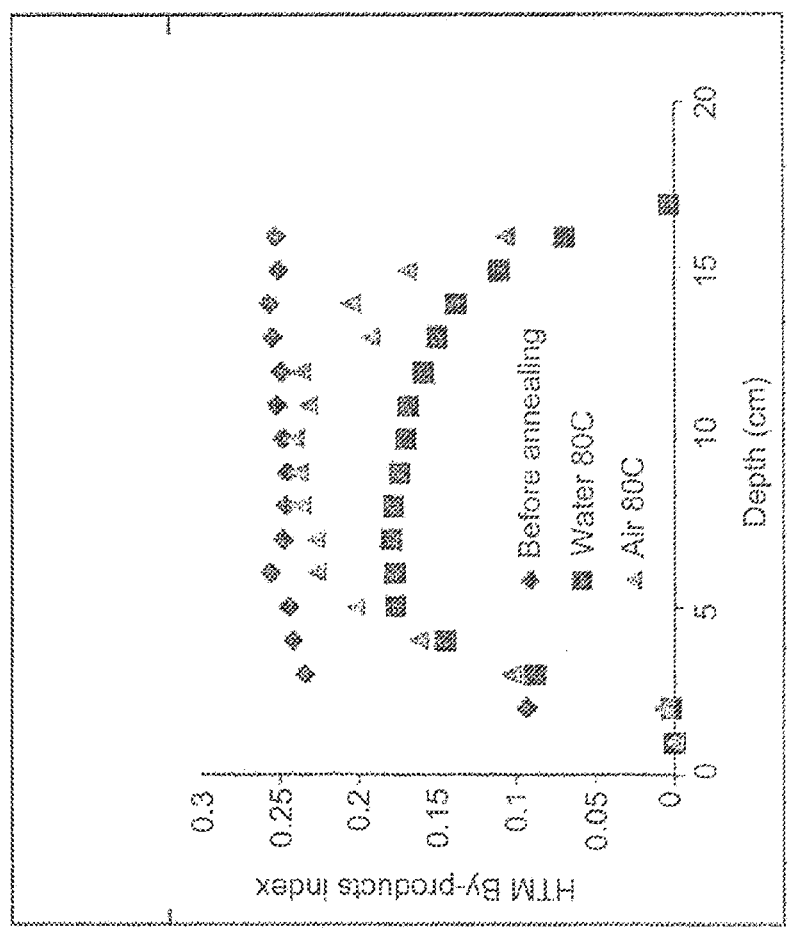
FIG. 13 shows the HTM by-products detected as a function of depth in ram extruded, vitamin E-blended, peroxide cross-linked UHMWPE before and after annealing at 80° C. in air or 80° C. in water for 18 hours.

The HTM by-products detected after high temperature melting and before annealing were decreased on the surface and in the bulk of the 1.8 cm-thick samples after annealing at 80° C. for 18 hours (FIG. 13). Annealing in water was more effective than annealing in air under these conditions.

Example 36. Diffusion of Antioxidant into High Temperature Melted and Irradiated UHMWPE Virgin UHMWPE blocks (7.3×4×3.1 cm) (GUR 1020) were machined from compression molded bar stock. These were subjected to high temperature melting at 320° C. for 6 hours in nitrogen, followed by irradiation to 175 kGy by gamma radiation, denoted as 'HTM'. The virgin UHMWPE irradiated to 100 kGy using gamma radiation served as a control. The irradiated blocks were machined into 1 cm cubes, which were doped in vitamin E with stirring under argon flow at 120° C. for 3 hours. The cubes were allowed to cool to room temperature and excess vitamin E was wiped off their surfaces.

After doping, one set of control cubes (n=2) was homogenized under argon, at ambient pressure, at 130° C. for 8 hours. Four sets (n=1, each) of the HTM doped cubes were homogenized at 150° C. for 1 or 2 hours and 180° C. for 30 mins or 1 hour, respectively. The wear and mechanical properties of both the HTM and control samples were measured prior to doping and homogenization.

Another set of controls were irradiated high temperature melted (HTM) blocks (n=1 each) that were melted at 180 and 220° C. for 6 hours to test the effect of high temperature melting on mechanical properties.

Thin sections (150 μm) were analyzed by Fourier Transform Infrared Spectroscopy (FTIR) and a vitamin E index was calculated by normalizing the absorbance at 1265 cm$^{-1}$ (1245-1275 cm$^{-1}$) by that at 1895 cm$^{-1}$ (1850-1985 cm$^{-1}$). The penetration depth of vitamin E was calculated as the depth up to which the vitamin E index of the sample was ≥0.02.

The penetration depth of vitamin E increased from 1.0±0.0 mm after doping to 3.8±0.3 mm for the 100 kGy irradiated control samples homogenized at 130° C. for 8 hours (p=0.003, FIG. 13), while for the HTM samples it increased from 0.9±0.0 mm after doping to 2.5±0.0, 3.5±0.0, 3.0±0.0 and 4.2±0.3 mm for samples homogenized at 150° C. for 1 hr, at 150° C. for 2 hours, at 180° C. for 30 minutes and at 180° C. for 1 hour, respectively.

The wear rate of the 100 kGy irradiated control prior to doping, (1.7±0.2 mg/MC) was comparable to that of 175 kGy irradiated HTMed sample (2.1±1.3 mg/MC). The elongation-at-break (EAB) and work to failure of the HTM sample prior to doping was higher than the control sample. The ultimate tensile strength (UTS) of the HTM sample prior to doping, was comparable to the control sample. The HTM samples melted at 180 and 220° C. for 6 hours showed significantly higher EAB as compared to the control sample. The UTS of the HTM samples after melting at 180 and 220° C. was slightly lower than the control sample while the work to failure was higher than the control sample.

Increasing the homogenization temperature to 180° C. for the HTMed, irradiated UHMWPE decreased the required homogenization time 8 fold while achieving similar penetration depths compared to the control sample homogenized below the melt. Despite melting at 180 and 220° C., the HTMed, irradiated samples showed improved toughness compared to irradiated control as measured by the tensile work-to-failure (WF) and EAB (Table 28-1). In addition, the wear resistance of the HTMed, irradiated UHMWPE was comparable to the irradiated control, suggesting that HTM before radiation cross-linking followed by doping with vitamin E and homogenization at above-the-melt temperatures may be a feasible alternative to fabricating total joint implants without sacrificing crucial properties.

TABLE 28-1

Elongation-at-break, UTS and yield strength values of all the test and control samples.

| Sample | EAB (%) | UTS (MPa) | WF (kJ/m$^2$) |
| --- | --- | --- | --- |
| 100 kGy - Control | 272 ± 14 | 46.4 ± 1.2 | 1557 ± 77 |
| 175 kGy - HTM | 318 ± 7 | 43.1 ± 0.8 | 1758 ± 48 |
| 175 kGy - HTM - Melted @ 180° C. - 6 h | 292 ± 4 | 40.1 ± 1.0 | 1684 ± 75 |
| 175 kGy - HTM - Melted @ 220° C. - 6 h | 301 ± 4 | 40.6 ± 0.5 | 1786 ± 38 |

Example 37. Two-Layer Direct Compression Molded UHMWPE

Medical grade GUR1050 UHMWPE was blended with 0.5 wt % vitamin E by diluting the 2 wt % vitamin E/GUR 1050 UHMWPE master batch of Example 9 with the addition of virgin GUR 1050 UHMWPE.

An approximately 100 g batch of each vitamin E/GUR 1050 UHMWPE blend was mixed with P130 in the amount of 0.9 wt % peroxide.

Figure 14:
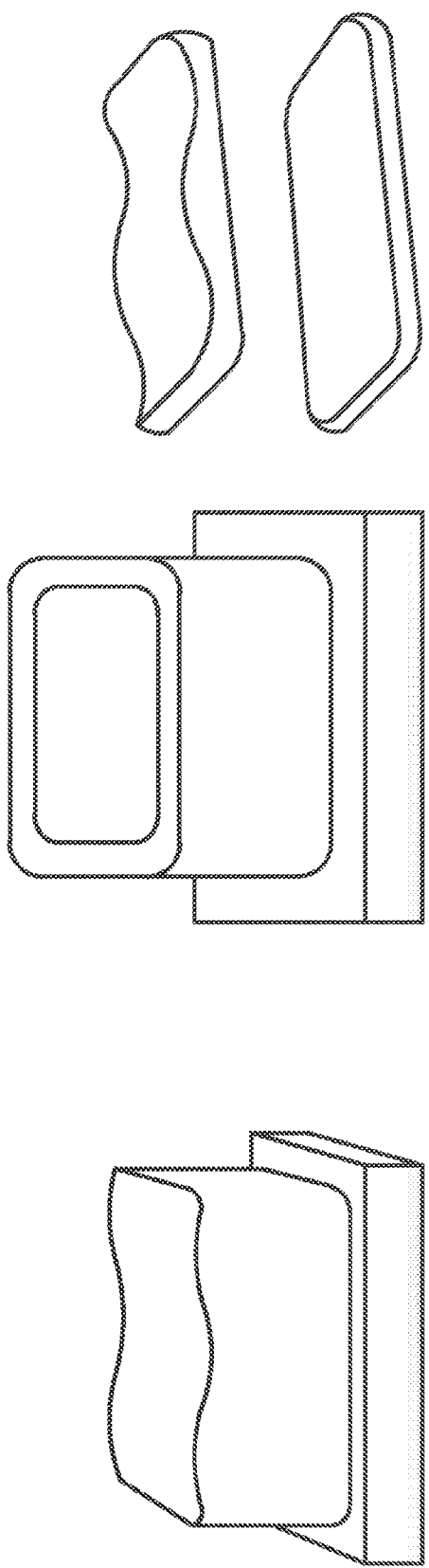
FIG. 14 shows a consolidation mold with curved surfaces.

About 50 grams of virgin UHMWPE powder was placed in the female mold (with push-out plate at the bottom). The contoured male component (FIG. 14) was placed on the powder and the assembled mold was placed in a consolidation press. The powder was pressed at 10 MPa for 3 minutes at ambient temperature. After this time, the mold was removed from the press and the contoured male component was removed. About 10 grams of the vitamin E and peroxide-blended UHMWPE was placed as a second layer on top of the partially consolidated first layer. The mold was closed again and placed between platens pre-heated to 190° C. The final consolidation of the two layers was then performed at 190° C. for 1 hour at 10-25 MPa. Then, the mold was cooled to about room temperature.

Example 38. Consolidation of Cross-Linking Agent Blended UHMWPE Using Different Consolidation Conditions Medical grade GUR1050 UHMWPE was blended with 0.5 wt % vitamin E by diluting the 2 wt % vitamin E/GUR 1050 UHMWPE master batch of Example 9 with the addition of virgin GUR 1050 UHMWPE.

An approximately 300 g batch of each vitamin E/GUR 1050 UHMWPE blend was mixed with P130 in the amount of 0.9 wt % peroxide.

About 100 g of the antioxidant and cross-linking agent-blended UHMWPE powder was placed in a cylindrical mold (diameter ~10.5 cm) and placed in between platens pre-heated to the initial molding temperature in a compression press. Pressure was applied at 15 MPa, which increased during molding up to 25 MPa. The platen temperature was changed after soaking at the initial temperature for a duration 1. The duration for each platen temperature is listed in Table 30-1.

TABLE 30-1

| Sample # | Initial temperature | Duration 1 (min) | Final temperature (° C.) | Duration 2 (min) |
|---|---|---|---|---|
| 69 | 160 | 15 | 190 | 15 |
| 71 | 160 | 10 | 190 | 20 |
| 72 | 160 | 20 | 190 | 10 |
| 74 | 140 | 90 | 190 | 30 |
| 76 | 160 | 15 | 230 | 15 |
| 77 | 140 | 10 | 230 | 15 |

The resulting cylindrical pucks (diameter ~10.5 cm, thickness ~1.1 cm) were machined and tested for cross-link density, wear and tensile mechanical properties as described in Examples 12, 13 and 14. The results are shown in Table 30-2. A 75 kGy irradiated and subsequently melted GUR1050 UHMWPE was also tested as control (CISM-75).

TABLE 30-2

Cross-link density (XLD), wear rate, ultimate tensile strength (UTS) and elongation-at-break (EAB) of 0.5 wt % vitamin E and 0.9 wt % P130-blended GUR1050 UHMWPE using different molding conditions as shown in Table 30-1.

| Cons. Temp (° C.) | XLD (mol/m$^3$) | Wear (mg/MC) | UTS (MPa) | EAB (%) |
|---|---|---|---|---|
| 0/120 min \| 160/190° C. (#44) | 247 ± 4 | 2.1 ± 0.2 | 39.9 ± 1.3 | 270 ± 8 |
| 120/0 min \| 160/190° C. (#45) | 218 ± 3 | 8.1 ± 1.2 | 51.5 ± 1.6 | 283 ± 7 |
| 15/15 min \| 160/190° C. (#69) | 227 ± 2 | Not-tested | 47.4 ± 1.6 | 326 ± 5 |
| 10/20 min \| 160/190° C. (#71) | 206 ± 6 | Not-tested | 42.1 ± 2.9 | 315 ± 5 |
| 20/10 min \| 160/190° C. (#72) | 186 ± 1 | Not-tested | 45.8 ± 6.4 | 326 ± 24 |
| 90/30 min \| 140/190° C. (#74) | 263 ± 1 | 2.0 ± 0.6 | 45.4 ± 3.5 | 252 ± 17 |
| 15/15 min \| 160/230° C. (#76) | 257 ± 4 | Not-tested | 41.5 ± 2.4 | 240 ± 8 |
| 10/15 min \| 140/230° C. (#77) | 249 ± 1 | Not-tested | 40.3 ± 2.4 | 245 ± 18 |
| CISM-75 (1050) | 247 ± 3 | 2.5 ± 0.1 | 45.3 ± 1.5 | 241 ± 9 |

Thus, the invention provides methods of manufacturing peroxide cross-linked and high temperature melted polymeric material.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

We claim:

1. A medical implant comprising a cross-linked polymeric material made by the method comprising the steps of:
    a. blending a polymeric material with at least one antioxidant at a concentration that is between 0.05 wt % and 66.0 wt % and at least one cross-linking agent at a concentration that is between 0.5 and 66.5 wt %;
    b. consolidating the blended polymeric material;
    c. heating the consolidated polymeric material to a temperature that is about 200° C. or more for a period of time, wherein the heating step comprises:
        i. heating the consolidated polymeric material to a temperature that is between about 200° C. and about 290° C.,
        ii. maintaining the consolidated blended polymeric material at a temperature that is between about 200° C. and about 290° C.,
        iii. heating the consolidated polymeric material to a temperature that is between about 290° C. and 350° C., and
        iv. maintaining the consolidated blended polymeric material at a temperature that is between about 290° C. and 350° C. for at least 5 hours but no more than 30 hours; and
    d. cooling the consolidated polymeric material, wherein the cooling step comprises:
        i. permitting the heated consolidated blended polymeric material to cool to a temperature that is between about 135° C. and about 180° C.,
        ii. maintaining the consolidated blended polymeric material at a temperature that is between about 135° C. and about 180° C., and
        iii. permitting the consolidated blended polymeric material to cool to a temperature that is between about room temperature and 60° C.

2. The medical implant according to claim 1, wherein at least one antioxidant is vitamin E or Tetrakis[methylene(3, 5-di-tertbutylhydroxyhydrocinnamate)] methane.

3. The medical implant according to claim 1, wherein at least one cross-linking agent is a peroxide, P130, a carbon-carbon initiator, 2,3-dimethyl-2,3-diphenylbutane, poly-1,4-diisopropylbenzene, or a mixture thereof.

4. The medical implant according to claim 1, wherein the heating after consolidation is done in inert gas.

5. The medical implant according to claim 1, wherein the heating after consolidation is done in air.

6. The medical implant according to claim 1, wherein the consolidation is carried out at a temperature that is between 150° C. and 210° C.

7. The medical implant according to claim 1, wherein the crosslinked polymeric material is further machined into a medical implant.

8. The medical implant according to claim 1, wherein the consolidation is done by ram extrusion.

9. The medical implant according to claim 1, wherein the antioxidant concentration is no more than 1.0 wt %.

10. The medical implant according to claim 1, wherein the crosslinking agent initiates cross-linking in the polymeric material.

11. An interlocked hybrid material made by the method comprising the steps of:
    a. blending a polymeric material with at least one antioxidant at a concentration that is between 0.05 wt % and 66.0 wt % and at least one cross-linking agent at a concentration that is between 0.5 and 66.5 wt %;
    b. layering the blended polymeric material and a second material;
    c. consolidating the layers, thereby forming an interlocked hybrid material;
    d. heating the interlocked hybrid material to a temperature that is above 200° C. for a period of time, wherein the heating step comprises:
        i. heating the interlocked hybrid material to a temperature that is between about 200° C. and about 290° C.,
        ii. maintaining the interlocked hybrid material at a temperature that is between about 200° C. and about 290° C.,
        iii. heating the interlocked hybrid material to a temperature that is between about 290° C. and 350° C. and iv. maintaining the interlocked hybrid material at a temperature that is between about 290° C. and 350° C. for at least 5 hours but no more than 30 hours; and e. cooling the interlocked hybrid material, wherein the cooling step comprises:
   i. permitting the heated interlocked hybrid material to cool to a temperature that is between about 135° C. and about 180° C.,
   ii. maintaining the interlocked hybrid material at a temperature that is between about 135° C. and about 180° C., and
   iii. permitting the interlocked hybrid material to cool to a temperature that is between about room temperature and 60° C.

12. The interlocked hybrid material according to claim 11, wherein the second material is a porous metal.

13. The interlocked hybrid material according to claim 11, wherein the interlocked hybrid material is consolidated in the form of a medical implant.

14. The interlocked hybrid material according to claim 11, wherein the interlocked hybrid material is machined into a medical implant.

15. The interlocked hybrid material according to claim 11, wherein the antioxidant concentration is no more than 1.0 wt %.

16. The interlocked hybrid material according to claim 11, wherein the crosslinking agent initiates cross-linking in the polymeric material.

17. The interlocked hybrid material according to claim 11, wherein the consolidation is carried out at a temperature that is between 150° C. and 210° C.

18. The interlocked hybrid material according to claim 11, wherein at least one antioxidant is vitamin E or Tetrakis [methylene(3,5-di-tertbutylhydroxyhydrocinnamate)] methane.

19. The interlocked hybrid material according to claim 11, wherein at least one cross-linking agent is a peroxide, P130, a carbon-carbon initiator, 2,3-dimethyl-2,3-diphenylbutane, poly-1,4-diisopropylbenzene, or a mixture thereof.

20. The interlocked hybrid material according to claim 11, wherein the heating after consolidation is done in inert gas.

21. The interlocked hybrid material according to claim 11, wherein the heating after consolidation is done in air.

22. The medical implant according to claim 3, wherein the peroxide is selected from the group consisting: diacyl peroxides, peroxyesters, peoxydicarbonates, dialkyl peroxides, ketone peroxides, peroxyketals, cyclic peroxides, peroxymonocarbonates, hydroperoxides, benzoyl peroxide, dicumyl peroxide, methyl ethyl ketone peroxide, acetone peroxide, 2,5-Di(tert-butylperoxy)-2,5-dimethyl-3-hexyne, 3,3,5,7,7-pentamethyl-1,2,4 trioxepane, dilauryl peroxide, methyl ether ketone peroxide, t-amyl peroxyacetate, t-butyl hydroperoxide, t-amyl peroxybenzoate, Di-t-amyl peroxide, 2,5-Dimethyl 2,5-Di(t-butylperoxy) hexane, t-butylperoxy isopropyl carbonate, succinic acid peroxide, cumene hydroperoxide, 2,4-pentanedione peroxide, t-butyl perbenzoate, diethyl ether peroxide, acetone peroxide, arachidonic acid 5-hydroperoxide, carbamide peroxide, tert-butyl hydroperoxide, t-butyl peroctoate, t-butyl cumyl peroxide, Di-sec-butylperoxydicarbonate, Di-2-ethyl hexyperoxydicarbonate, 1,1-Di(t-butylperoxy)cyclohexane, 1, 1-Di (tertbutyl peroxy)-3, 3, 5-trimethylcyclohexane, 2, 5-Dimethyl-2, 5-di(tert-butylperoxy)hexane, 3,3,5,7,7-Pentamethyl-1,2,4-trioxepane, Butyl 4,4-di(tert-butylperoxy)valerate, Di(2,4-dichlorobenzoyl) peroxide, Di(4-methylbenzoyl) peroxide, Di(tert-butylperoxyisopropyl) benzene, tert-Butyl cumyl peroxide, tert-Butyl peroxy-3,5,5-trimethylhexanoate, tert-Butyl peroxybenzoate, and tert-Butylperoxy 2-ethylhexyl carbonate, or mixtures thereof.

23. The interlocked hybrid material according to claim 19, wherein the peroxide is selected from the group consisting: diacyl peroxides, peroxyesters, peoxydicarbonates, dialkyl peroxides, ketone peroxides, peroxyketals, cyclic peroxides, peroxymonocarbonates, hydroperoxides, benzoyl peroxide, dicumyl peroxide, methyl ethyl ketone peroxide, acetone peroxide, 2,5-Di(tert-butylperoxy)-2,5-dimethyl-3-hexyne, 3,3,5,7,7-pentamethyl-1,2,4 trioxepane, dilauryl peroxide, methyl ether ketone peroxide, t-amyl peroxyacetate, t-butyl hydroperoxide, t-amyl peroxybenzoate, Di-t-amyl peroxide, 2,5-Dimethyl 2,5-Di(t-butylperoxy) hexane, t-butylperoxy isopropyl carbonate, succinic acid peroxide, cumene hydroperoxide, 2,4-pentanedione peroxide, t-butyl perbenzoate, diethyl ether peroxide, acetone peroxide, arachidonic acid 5-hydroperoxide, carbamide peroxide, tert-butyl hydroperoxide, t-butyl peroctoate, t-butyl cumyl peroxide, Di-sec-butylperoxydicarbonate, Di-2-ethyl hexyperoxydicarbonate, 1,1-Di(t-butylperoxy)cyclohexane, 1, 1-Di (tertbutyl peroxy)-3, 3, 5-trimethylcyclohexane, 2, 5-Dimethyl-2, 5-di(tert-butylperoxy)hexane, 3,3,5,7,7-Pentamethyl-1,2,4-trioxepane, Butyl 4,4-di(tert-butylperoxy)valerate, Di(2,4-dichlorobenzoyl) peroxide, Di(4-methylbenzoyl) peroxide, Di(tert-butylperoxyisopropyl) benzene, tert-Butyl cumyl peroxide, tert-Butyl peroxy-3,5,5-trimethylhexanoate, tert-Butyl peroxybenzoate, and tert-Butylperoxy 2-ethylhexyl carbonate, or mixtures thereof.

\* \* \* \* \*